(12) United States Patent
Masaki et al.

(10) Patent No.: US 12,357,252 B2
(45) Date of Patent: Jul. 15, 2025

(54) DEVICES, SYSTEMS, METHODS, AND STORAGE MEDIA FOR CONTROLLING A BENDABLE MEDICAL DEVICE

(71) Applicant: Canon U.S.A., Inc., Melville, NY (US)

(72) Inventors: Fumitaro Masaki, Brookline, MA (US); Brian Ninni, Woburn, MA (US); Takahisa Kato, Brookline, MA (US)

(73) Assignee: Canon U.S.A., Inc., Melville, NY (US)

( * ) Notice: Subject to any disclaimer, the term of this patent is extended or adjusted under 35 U.S.C. 154(b) by 141 days.

(21) Appl. No.: 18/198,141

(22) Filed: May 16, 2023

(65) Prior Publication Data

US 2024/0382168 A1 Nov. 21, 2024

(51) Int. Cl.
*A61B 6/00* (2006.01)
*A61B 90/00* (2016.01)

(52) U.S. Cl.
CPC ............ *A61B 6/487* (2013.01); *A61B 6/4441* (2013.01); *A61B 90/08* (2016.02); *A61B 90/39* (2016.02); *A61B 2090/0811* (2016.02); *A61B 2090/3966* (2016.02)

(58) Field of Classification Search
CPC ....... A61B 6/487; A61B 6/4441; A61B 90/08; A61B 90/39; A61B 2090/0811; A61B 2090/3966
See application file for complete search history.

(56) References Cited

U.S. PATENT DOCUMENTS

| | | | |
|---|---|---|---|
| 9,008,279 B2 | 4/2015 | Grzeda et al. | |
| 9,633,431 B2 | 4/2017 | Merlet | |
| 11,096,552 B2 | 8/2021 | Hata et al. | |
| 11,103,992 B2 | 8/2021 | Tanaka et al. | |
| 11,419,564 B2 | 8/2022 | Narabu | |
| 11,559,687 B2 * | 1/2023 | Goedeke | ............ A61N 1/36139 |

(Continued)

OTHER PUBLICATIONS

Verena Veulemans et al., Optimal C-arm angulation during transcatheter aortic valve replacement: Accuracy of a rotational C-arm computed tomography based three dimensional heart model, World Journal of Cardiology, Oct. 26, 2016; 8(10): 606-614.

(Continued)

*Primary Examiner* — Dixomara Vargas
(74) *Attorney, Agent, or Firm* — Canon U.S.A., Inc. IP Division

(57) ABSTRACT

Some devices, systems, and methods obtain a fluoroscopic image and corresponding C-arm positional information of the fluoroscopic image, wherein the fluoroscopic image depicts a distal end of a bendable medical device, and wherein the C-arm positional information indicates a rotation angle of a C-arm of a C-arm scanner; obtain an orientation of the distal end in an image plane of the fluoroscopic image, wherein the image plane is defined in a detector reference frame; obtain an instructed direction; determine, in the image plane, a movement direction of the distal end that corresponds to the instructed direction; map the movement direction from the image plane to a distal-end reference frame of the distal end, wherein the mapping is based on an orientation of the distal end in an intermediate reference frame and on the C-arm positional information; and control the distal end to move according to the mapped movement direction.

25 Claims, 28 Drawing Sheets

(56) References Cited

U.S. PATENT DOCUMENTS

| | | | |
|---|---|---|---|
| 2002/0055674 A1* | 5/2002 | Ben-Haim | A61B 5/6858 |
| | | | 600/374 |
| 2005/0027193 A1 | 2/2005 | Mitschke et al. | |
| 2012/0289825 A1* | 11/2012 | Rai | A61B 6/547 |
| | | | 600/425 |
| 2016/0157751 A1* | 6/2016 | Mahfouz | A61B 5/062 |
| | | | 600/409 |
| 2017/0143494 A1* | 5/2017 | Mahfouz | A61B 17/1703 |
| 2020/0245982 A1 | 8/2020 | Kopel et al. | |
| 2021/0121051 A1 | 4/2021 | Altshuler et al. | |
| 2022/0202500 A1 | 6/2022 | Ninni et al. | |
| 2022/0202501 A1 | 6/2022 | Zhang et al. | |
| 2022/0202502 A1 | 6/2022 | Zhang et al. | |
| 2022/0346885 A1 | 11/2022 | Kunio et al. | |
| 2023/0165482 A1* | 6/2023 | Mahfouz | A61B 5/1114 |
| | | | 703/2 |
| 2023/0233819 A1* | 7/2023 | Malek | A61M 27/006 |
| | | | 604/8 |

OTHER PUBLICATIONS

Abhishek Kumar et al., Robotic Bronchoscopy for Peripheral Pulmonary Lesion Biopsy: Evidence-Based Review of the Two Platforms, Diagnostics 2021, 11, 1479, Aug. 2021.

N. Simaan et al., A dexterous system for laryngeal surgery, IEEE International Conference on Robotics and Automation 2004, Proceedings ICRA 04, 2004 (vol. 1, pp. 351-357), Apr. 2004.

R. J. Webster et al., Design and kinematic modeling of constant curvature continuum robots: A review, International Journal of Robotics Research, 29(13), 1661-1683, Nov. 2010.

F. Masaki et al., Technical Validation of Multi-Section Robotic Bronchoscope with First Person View Control for Transbronchial Biopsies of Peripheral Lung, IEEE Transactions on Biomedical Engineering, 68(12), 3534-3542, Dec. 2021.

A. Bajo et al., Robotic-assisted micro-surgery of the throat: The trans-nasal approach, Proceedings of the 2013 IEEE International Conference on Robotics and Automation, pp. 232-238, May 2013.

* cited by examiner

DEVICES, SYSTEMS, METHODS, AND STORAGE MEDIA FOR CONTROLLING A BENDABLE MEDICAL DEVICE

BACKGROUND

Technical Field

This application generally concerns medical imaging; bendable medical devices; and devices, systems, and methods that perform medical procedures using bendable medical devices.

Background

Bendable medical devices can be used to perform medical procedures. For example, bendable optical-imaging devices (e.g., endoscopes, flexible borescopes) enable the imaging of internal tissues, organs, and structures. Also for example, a bendable medical device may be used to reach and biopsy or treat abnormalities in the lung. The bendable medical device, which may include a flexible body, a coil, and a tool (e.g., optical probe), may be navigated through a lumen (e.g., a vessel) or a cavity.

A bendable medical device may include an electromagnetic sensor that allows the location of the device's distal end to be tracked. This allows a physician to know where the distal end is in relationship to the patient's anatomy during a procedure. Also, a physician can use fluoroscopy to track the location of the device's distal end.

SUMMARY

Some embodiments of a device comprise one or more computer-readable media and one or more processors in communication with the one or more computer-readable media. The one or more processors and the one or more computer-readable media are configured to cooperate to perform operations that comprise obtaining a fluoroscopic image that was generated by a C-arm scanner and corresponding C-arm positional information for the fluoroscopic image, wherein the fluoroscopic image depicts a distal end of a bendable medical device, and wherein the C-arm positional information indicates a rotation angle of a C-arm of the C-arm scanner; determining an orientation of the distal end in an image plane of the fluoroscopic image, wherein the image plane is defined in a detector reference frame of the C-arm scanner; obtaining an instructed direction; determining, in the image plane, a movement direction of the distal end that corresponds to the instructed direction, wherein the determining is based on the orientation of the distal end in the image plane, and wherein the movement direction lies in the imaging plane; mapping the movement direction from the image plane, which is defined in the detector reference frame, to a distal-end reference frame of the distal end, thereby generating a mapped movement direction, wherein the mapping is based on an orientation of the distal end in an intermediate reference frame and on the corresponding C-arm positional information, and wherein the mapped movement direction in the distal-end reference frame lies in the image plane; and controlling the distal end to move according to the mapped movement direction.

Some embodiments of a method comprise the following: obtaining a fluoroscopic image that was generated by a C-arm scanner and corresponding C-arm positional information for the fluoroscopic image, wherein the fluoroscopic image depicts a distal end of a bendable medical device, and wherein the C-arm positional information indicates a rotation angle of a C-arm of the C-arm scanner; obtaining an orientation of the distal end in an image plane of the fluoroscopic image, wherein the image plane is defined in a detector reference frame of the C-arm scanner; obtaining an instructed direction; determining, in the image plane, a movement direction of the distal end that corresponds to the instructed direction, wherein the determining is based on the orientation of the distal end in the image plane, and wherein the movement direction lies in the imaging plane; mapping the movement direction from the image plane, which is defined in the detector reference frame, to a distal-end reference frame of the distal end, thereby generating a mapped movement direction, wherein the mapping is based on an orientation of the distal end in an intermediate reference frame and on the C-arm positional information; and controlling the distal end to move according to the mapped movement direction.

Some embodiments of a method for controlling a bendable medical device comprise the following: obtaining a fluoroscopic image that was generated by a C-arm scanner and corresponding C-arm positional information for the fluoroscopic image, wherein the fluoroscopic image depicts a distal end of a bendable medical device, and wherein the C-arm positional information indicates a rotation angle of a C-arm of the C-arm scanner; obtaining distal-end positional information, which indicates an orientation of the distal end; generating a reference-frame mapping between the detector reference frame and a distal-end reference frame of the distal end, wherein the reference-frame mapping is generated based on an orientation of the distal end in an intermediate reference frame and on the C-arm positional information; generating an inter-view-relationship indicator, which indicates a relationship between the detector reference frame and the distal-end reference frame, based on the reference-frame mapping; and displaying the fluoroscopic image and the inter-view-relationship indicator.

DESCRIPTION

Figure 1:
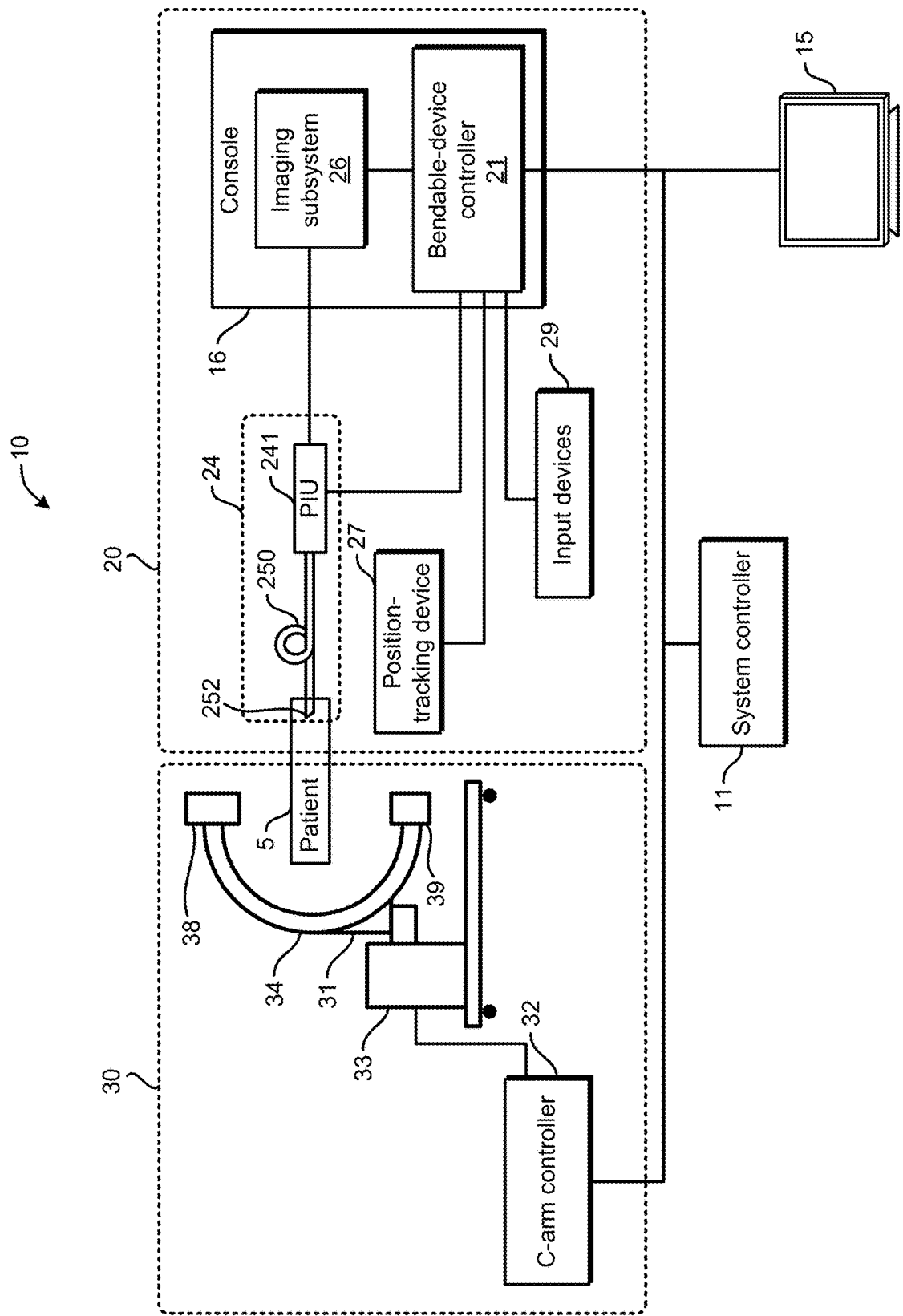
FIG. 1 illustrates an example embodiment of a medical system.

The following paragraphs describe certain explanatory embodiments. Other embodiments may include alternatives, equivalents, and modifications. Additionally, the explanatory embodiments may include several novel features, and a particular feature may not be essential to some embodiments of the devices, systems, and methods that are described herein. Furthermore, some embodiments include features from two or more of the following explanatory embodiments. Thus, features from various embodiments may be combined and substituted as appropriate.

Also, as used herein, the conjunction "or" generally refers to an inclusive "or," although "or" may refer to an exclusive "or" if expressly indicated or if the context indicates that the "or" must be an exclusive "or." Furthermore, as used herein, the terms "first," "second," and so on, do not necessarily denote any ordinal, sequential, or priority relation and may be used to more clearly distinguish one member, operation, element, group, collection, set, etc. from another without expressing any ordinal, sequential, or priority relation.

Additionally, in this description and the drawings, an alphabetic suffix on reference numerals may be used to indicate a specific instance of the feature identified by the reference numerals. For example, the wire-guiding members in a group of wire-guiding members may be identified with the reference numerals 258 when a particular wire-guiding member is not being distinguished. However, 258A may be used to identify a specific wire-guiding member when the specific wire-guiding member is being distinguished from the rest of the wire-guiding members 258.

FIG. 1 illustrates an example embodiment of a medical system. The medical system 10 includes at least one display device 15, a bendable medical system 20, and a C-arm system 30.

The C-arm system 30 includes a C-arm scanner 31, which can capture images (e.g., X-ray images, such as fluoroscopy images) of a patient 5, and a C-arm controller 32, which is a computer that is configured to control the C-arm scanner 31. The C-arm scanner 31 includes an X-ray source 38, an X-ray detector 39, a support frame 33, and a C-arm 34. The C-arm controller 32 can send the captured images to other devices, such as the system controller 11 and the bendable-device controller 21. Also, in some embodiments, the C-arm controller 32 is located in the housing of the C-arm scanner 31.

The bendable medical system 20 includes a bendable-device controller 21, a bendable medical device 24 that can capture images or perform medical operations inside of a patient 5, an imaging subsystem 26, a position-tracking device 27, and input devices 29 (e.g., a joystick, a control pad, a mouse, a keyboard, a touchscreen). The bendable medical device 24 includes a tubular flexible body 250 that interfaces with the bendable-device controller 21 and the imaging subsystem 26 through a patient-interface unit 241. The bendable-device controller 21 is a computer that is configured to control the bendable medical device 24, the imaging subsystem 26, and the position-tracking device 27. Also, the bendable-device controller 21 and the imaging subsystem 26 may be housed together in a console 16.

In some embodiments, the bendable medical device 24 is a steerable instrument, such a continuum robot. And the bendable medical device 24 can be configured for a number of medical applications or industrial applications. For medical applications, the bendable medical device 24 can be configured as a robotic endoscope, as a steerable catheter, or as a surgical introducer sheath or sleeve that uses principles of kinematic (robotic) navigation for guiding a medical tool through tortuous bodily lumens, for example. Robotic endoscopes can be used for a variety of different diagnostic and interventional procedures including, but not limited to, colonoscopy, bronchoscopy, laparoscopy, video endoscopy, etc. In the case of a video endoscope, the bendable medical device 24 would be configured with a miniature video camera, such as a CCD or CMOS camera, located at the distal end of the bendable medical device 24, as well as electronic cabling and illumination optics (an optical fiber) extending along a tool channel.

A physician can use the one or more input devices 29 to control the tubular flexible body 250. For example, in some embodiments, the one or more input devices 29 include a gamepad-like controller (a joystick or a control pad that is similar to a joystick or a control pad that is used for video games or computer games). And the cardinal direction of the joystick or control pad is mapped to an endoscopic viewpoint, which is a first-person view (first person point-of-view) at the distal end 252 of the tubular flexible body 250, so that the physician can operate the tubular flexible body 250 from the perspective of the endoscopic viewpoint.

Figure 2A:
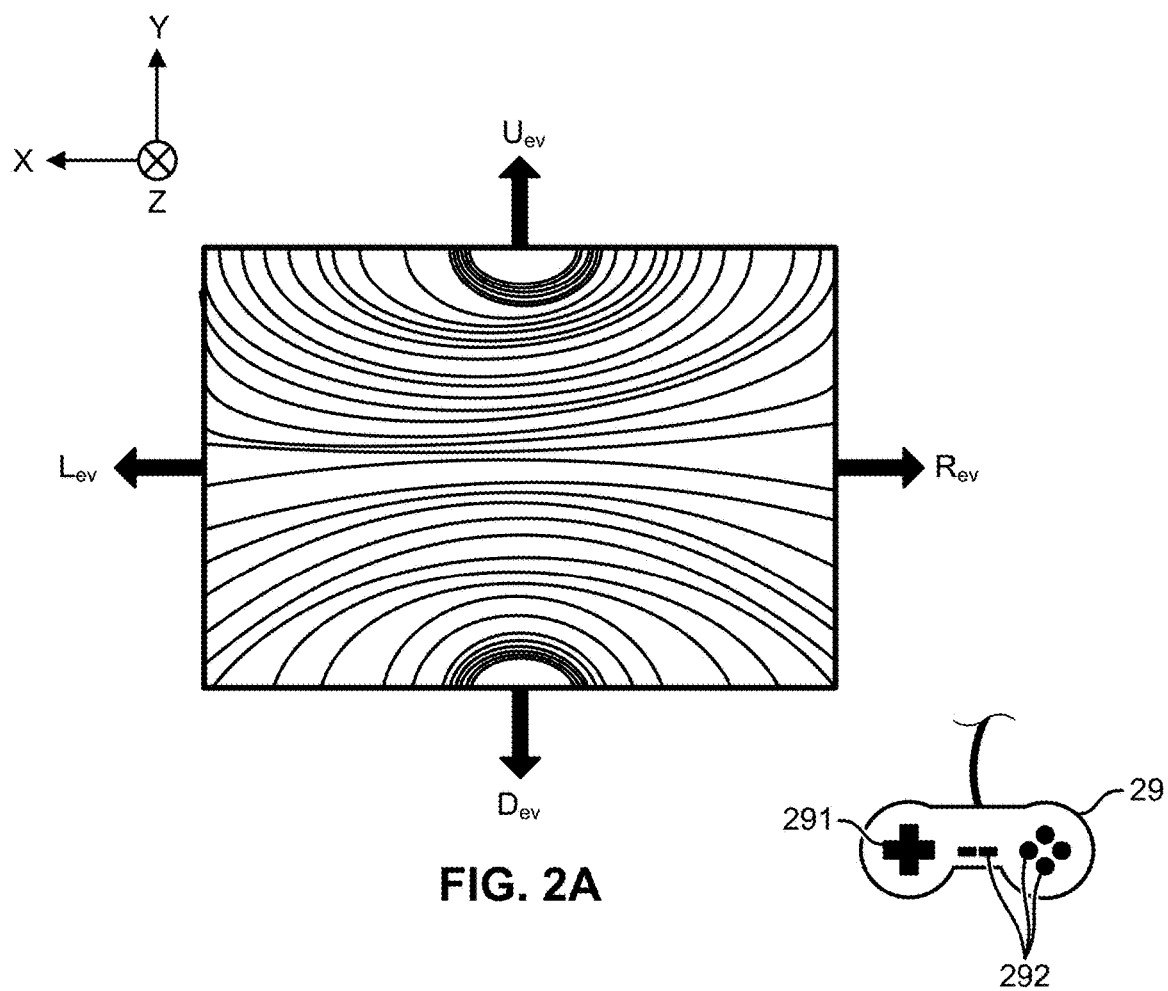
FIG. 2A illustrates an example of an endoscopic image and an input device.

For example, FIG. 2A illustrates an example of an endoscopic image and an input device, which is a control pad 29 in this example. The endoscopic image shows an endoscopic viewpoint (a first-person view) from the distal end 252.

The control pad 29 includes a directional pad 291 (or a joystick) and buttons 292. In some embodiments, the physician may be able to control the distal end 252 to move left (direction $L_{ev}$) by pressing the directional pad 291 to the left, to move right (direction $R_{ev}$) by pressing the directional pad 291 to the right, to move up (direction $U_{ev}$) by pressing the directional pad 291 up, and to move down (direction $D_{ev}$) by pressing the directional pad 291 down. Also, the up and down controls may be reversed. And the physician may be able to move the distal end 252 forward and backward by pressing respective buttons 292. Furthermore, the directional pad 291, one or more of the buttons 292, or some combination of the directional pad 291 and one or more of the buttons 292 may allow a physician to change the rotation angle (the roll angle) along the longitudinal axis of the distal end 252.

The medical system 10 is controlled by a system controller 11. In some embodiments, the system controller 11 also performs the functions of the bendable-device controller 21 or is housed in the console 16.

The bendable-device controller 21 (or, in some embodiments, the system controller 11) is configured to generate a navigation screen and display it on the at least one display device 15. For example, the bendable-device controller 21 may generate a three-dimensional (3D) model of a structure (e.g., a branching structure, such as the airway of the lungs of a patient 5) based on images (e.g., CT images, MRI images) of the structure. Also, the bendable-device controller 21 may acquire the 3D model from another device. And a two-dimensional (2D) model can be used instead of 3D model. The 2D or 3D model can be generated before navigation starts. Alternatively, the 2D or 3D model can be generated in real-time (in parallel with the navigation). As an example, this embodiment uses a model of a branching structure. However, the model is not limited to a model of a branching structure. For example, a model of a non-branching structure to a target can be used instead of a model of a branching structure. One such example is a model of a broad space, such as a model of a place or a space where an observation or a work is performed by using a bendable medical device 24.

The bendable-device controller 21 may acquire distal-end positional information of the tubular flexible body 250 using the position-tracking device 27, which is part of a position-tracking system. Positional information indicates positions, and, as used herein, a position includes one or both of a location and an orientation. In some embodiments, the position-tracking system includes one or more sensors that are located at a distal end 252 of the tubular flexible body (e.g., the position sensors 245 in FIG. 25B), and some embodiments of the position-tracking device 27 include sensors that detect the positions (locations and orientations) of the one or more sensors that are at the distal end 252 the tubular flexible body 250 and send corresponding distal-end positional information to the bendable-device controller 21. Also, some embodiments of the position-tracking device 27 generate an electromagnetic (EM) field that can be detected by the one or more sensors that are at the distal end 252 of the tubular flexible body 250, and the one or more sensors that are in the tubular flexible body 250 can generate the corresponding distal-end positional information based on the detected EM field. In the following description, distal-end positional information that is generated by a position-tracking system could include either positional information generated by sensors in the tubular flexible body 250 (e.g., the position sensors 245 in FIG. 25B) or positional information generated by the position-tracking device 27.

During a medical procedure, the distal end 252 of the tubular flexible body 250 can be navigated through a lumen to a target (e.g., a lesion). Once the distal end 252 has been navigated close to the target, the C-arm scanner 31 can capture fluoroscopic images of the distal end 252, which a physician (or other user) can use to confirm the position (the location and the orientation) of the distal end 252. For example, a physician can use the fluoroscopic images to determine the position of the distal end 252 relative to a target.

If the physician, while using the fluoroscopic images, confirms a suboptimal alignment between the distal end 252 and the target, then the physician needs to further adjust the orientation of the distal end 252. But each fluoroscopic image is captured from a respective point of view (a fluoroscopic viewpoint) that is different from the endoscopic viewpoints. Accordingly, when operating the distal end 252 based on a fluoroscopic image, the control mappings between the fluoroscopic viewpoint and the endoscopic viewpoint at the distal end 252 could be counterintuitive because the direction of a control in the endoscopic viewpoint may not match the direction of the control in the fluoroscopic viewpoint.

Figure 2B:
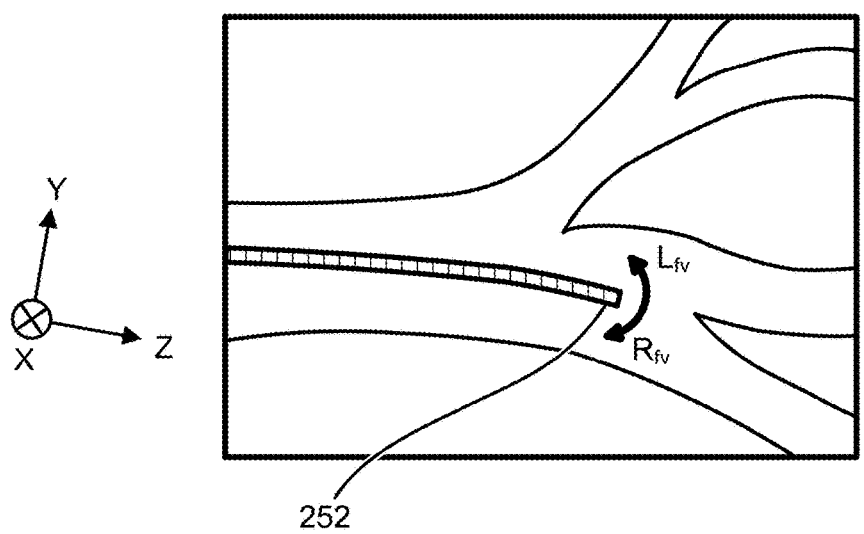
FIG. 2B illustrates an example of a fluoroscopic image.

For example, FIG. 2B illustrates an example of a fluoroscopic image, which was captured from a fluoroscopic viewpoint. Relative to the endoscopic viewpoint in the endoscopic image in FIG. 2A, the fluoroscopic viewpoint is rotated around the z axis by 90 degrees. Accordingly, in FIGS. 2A-B, a left direction in the endoscopic viewpoint (direction $L_{ev}$) does not correspond to the left direction in the fluoroscopic viewpoint (direction $L_{fv}$). If a physician wants to turn the distal end 252 to the left (direction $L_{fv}$) in the fluoroscopic image in FIG. 2B, the mapping between direction $L_{fv}$ in the fluoroscopic viewpoint and the corresponding direction in the endoscopic viewpoint (which is approximately direction $U_{ev}$ in this example) is not intuitive. Thus, the control mappings between directions in the endoscopic viewpoint and directions in the fluoroscopic viewpoint are not intuitive. This counterintuitive control mapping can prolong the procedure, cause a suboptimal alignment, and impose a mental burden on the physician.

After a trial-and-error process, the physician could find the control direction that moves the distal end 252 in the desired direction in the fluoroscopic image. However, the physician often needs to rotate the C-arm 34 and capture additional fluoroscopic images to confirm the alignment between the distal end 252 and the target. And the mappings between the directions in the endoscopic viewpoint and the fluoroscopic viewpoint change as the C-arm 34 is rotated. Consequently, the physician needs to redo the trial-and-error process to find the new control direction to move the distal end 252 in the desired direction in the new fluoroscopic viewpoint.

Thus, some embodiments of the medical system 10 automatically map control directions (instructed directions) from the fluoroscopic viewpoint to the endoscopic viewpoint. This allows a physician to input an instructed direction in the fluoroscopic viewpoint even if the corresponding movement direction in the endoscopic viewpoint is a different direction. For example, referring to FIGS. 2A-B, to make the distal end 252 turn to the left (direction $L_{fv}$) in the fluoroscopic image in FIG. 2B, the medical system 10 may allow a physician to input a "left" instructed direction using the control pad 29 and then map the "left" instructed direction to the corresponding movement direction (approximately direction $U_{ev}$) in the endoscopic viewpoint in FIG. 2A.

Figure 3:
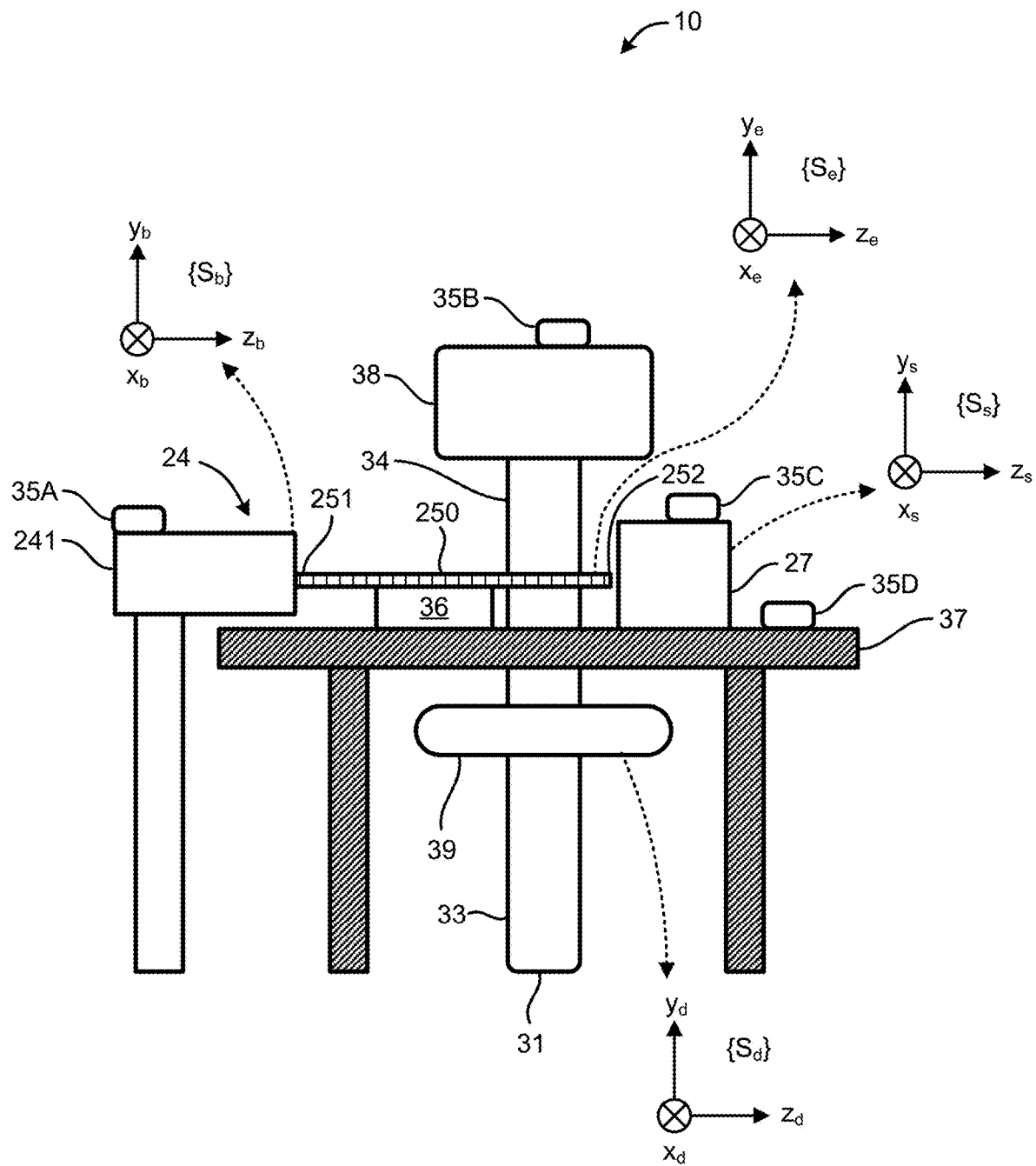
FIG. 3 illustrates another view of the medical system in FIG. 1.
Figure 4:
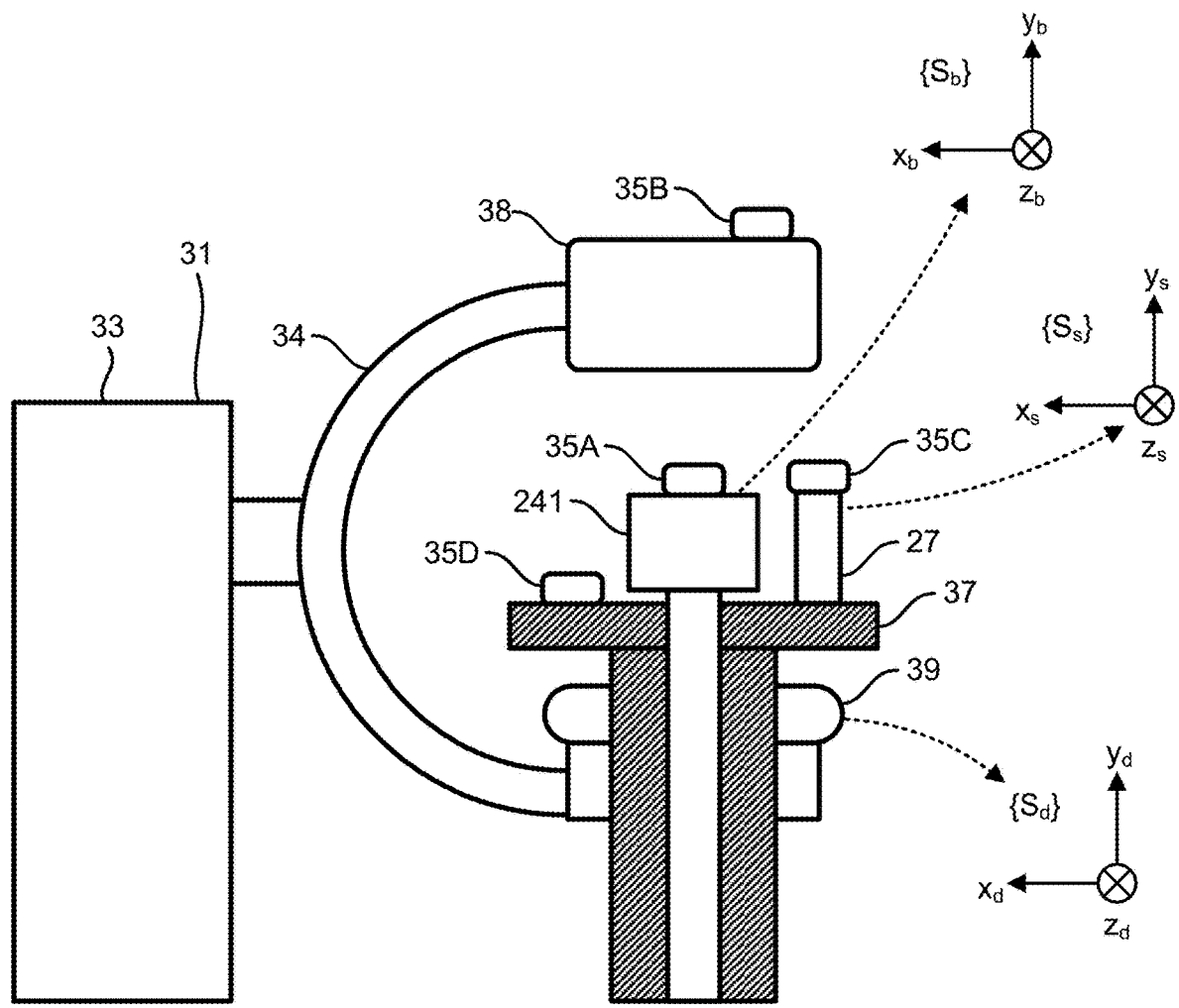
FIG. 4 illustrates another view of the medical system in FIG. 1.

FIGS. 3 and 4 illustrate other views of the medical system 10 in FIG. 1. Note that, to simplify FIGS. 3 and 4, some components of the medical system 10 are not illustrated. A patient bed 37 has been placed in the scanning range of the C-arm scanner 31. Also, the tubular flexible body 250 has been placed on a radiolucent holder 36. Additionally, four level gauges 35 have been placed on the members of the system. A first level gauge 35A has been placed on the PIU 241, a second level gauge 35B has been placed on the X-ray source 38, a third level gauge 35C has been placed on the position-tracking device 27, and a fourth level gauge 35D has been placed on the patient bed 37.

The medical system 10 is shown during calibration of the reference frame (frame of reference) $\{S_b\}$ of the proximal end 251 of the bendable medical device 24, of the reference frame $\{S_e\}$ of the distal end 252 of the bendable medical device 24, of the reference frame $\{S_s\}$ of the position-tracking device 27 (if the position-tracking device 27 is a member of a position-tracking system, the position-tracking system may have the same reference frame as the position-tracking device 27), and of the reference frame $\{S_d\}$ of the C-arm scanner 31. The reference frame $\{S_b\}$ of the proximal end 251 of the bendable medical device 24 is defined by the vectors $\{x_b, y_b, z_b\}$. The reference frame $\{S_e\}$ of the distal end 252 of the bendable medical device 24 is defined by the vectors $\{x_e, y_e, z_e\}$. The reference frame $\{S_s\}$ of the position-tracking device 27 is defined by the vectors $\{x_s, y_s, z_s\}$. And the reference frame $\{S_d\}$ of the C-arm scanner 31 is defined by the vectors $\{x_d, y_d, z_d\}$. Also, one or both of the reference frame $\{S_b\}$ of the proximal end 251 and the reference frame $\{S_s\}$ of the position-tracking device 27 may be intermediate reference frames. Examples of reference frames include coordinate systems. Also, the proximal end 251 of the bendable medical device 24, the position-tracking device 27, and the C-arm scanner 31 each generate positional information that is defined in their respective reference frame. For example, the position-tracking device 27 generates positional information that is defined in the reference frame $\{S_s\}$ of the position-tracking device 27.

In this example, the 0 degree rotation angle of the C-arm scanner 31 is defined as the direction of gravity (the gravitational axis), and, during calibration, the rotation angle of the C-arm scanner 31 is adjusted to 0 degrees using the second level gauge 35B. This aligns vector $y_d$ with the gravitational axis. Furthermore, the first level gauge 35A, the third level gauge 35C, and the fourth level gauge 35D are used to align vectors $y_b$, $y_e$, and $y_s$ with the gravitational axis.

The radiolucent holder 36 has a specified thickness (e.g., the thickness between a patient's back and trachea). And a level gauge can be used to confirm that the radiolucent holder 36 is level.

Figure 5:
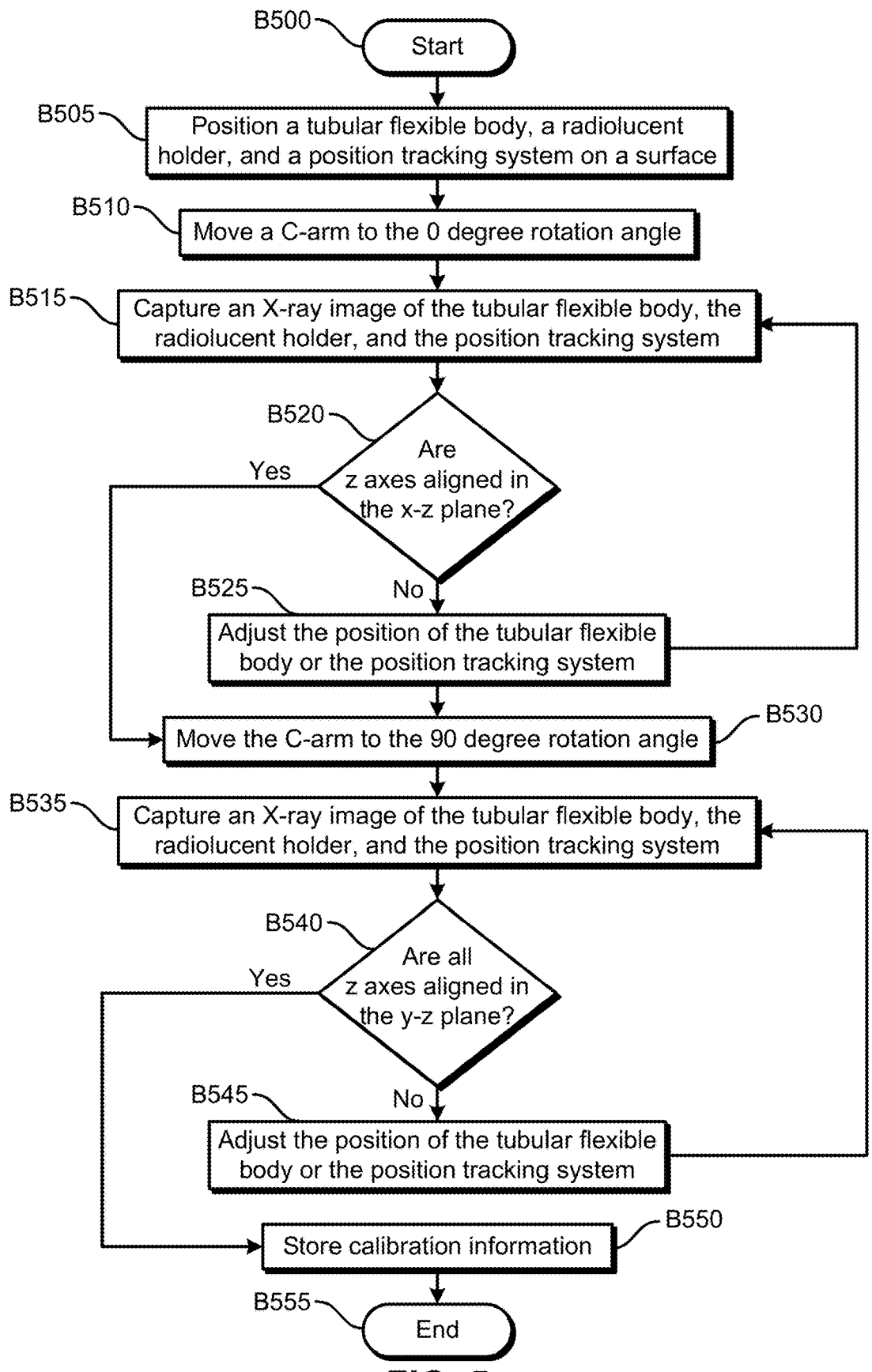
FIG. 5 illustrates an example embodiment of an operational flow for calibrating a medical system.

FIG. 5 illustrates an example embodiment of an operational flow for calibrating a medical system. Although this operational flow and the other operational flows that are described herein are each presented in a certain respective order, some embodiments of these operational flows perform at least some of the operations in different orders than the presented orders. Examples of different orders include concurrent, parallel, overlapping, reordered, simultaneous, incremental, and interleaved orders. Also, some embodiments of these operational flows include operations (e.g., blocks) from more than one of the operational flows that are described herein. Thus, some embodiments of the operational flows may omit blocks, add blocks (e.g., include blocks from other operational flows that are described herein), change the order of the blocks, combine blocks, or divide blocks into more blocks relative to the example embodiments of the operational flows that are described herein.

The flow starts in block B500 and then moves to block B505, where a bendable medical device 24, which includes a tubular flexible body 250; a radiolucent holder 36; and a position-tracking device 27 are placed on a support surface (e.g., a patient bed 37) in the scanning range of a C-arm scanner 31. The tubular flexible body 250 of the bendable medical device 24 is placed on the radiolucent holder 36 while the tubular flexible body 250 has a straight pose. Also, level gauges 35 can be used to confirm that a PIU 241 of the bendable medical device 24 (which holds a proximal end 251 of the tubular flexible body 250), the radiolucent holder 36, the position-tracking device 27, and the support surface are level (e.g., their y axes are aligned with the gravitational axis).

Next, in block B510, a system controller 11 controls the C-arm 34 of the C-arm scanner 31 to move to the 0 degree rotation angle. One or more level gauges can be used to confirm that the C-arm 34 of the C-arm scanner 31 is situated in the 0 degree rotation angle.

Figure 6A:
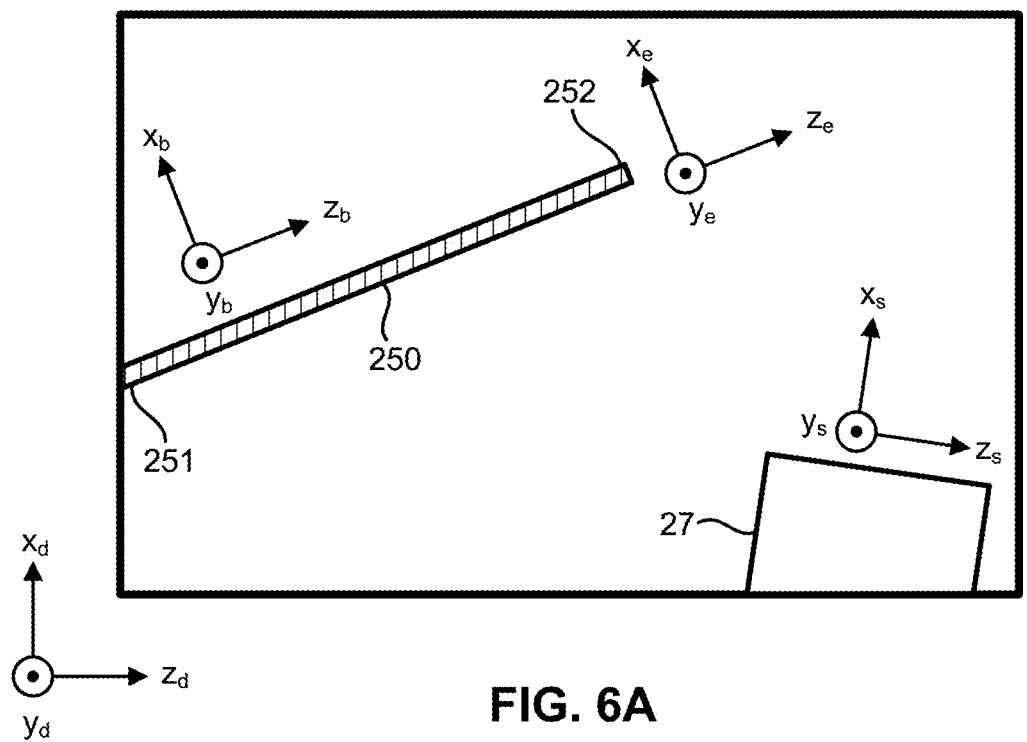
FIGS. 6A-B illustrate embodiments of X-ray images of a tubular flexible body, a radiolucent holder, and a position-tracking device.
Figure 6B:
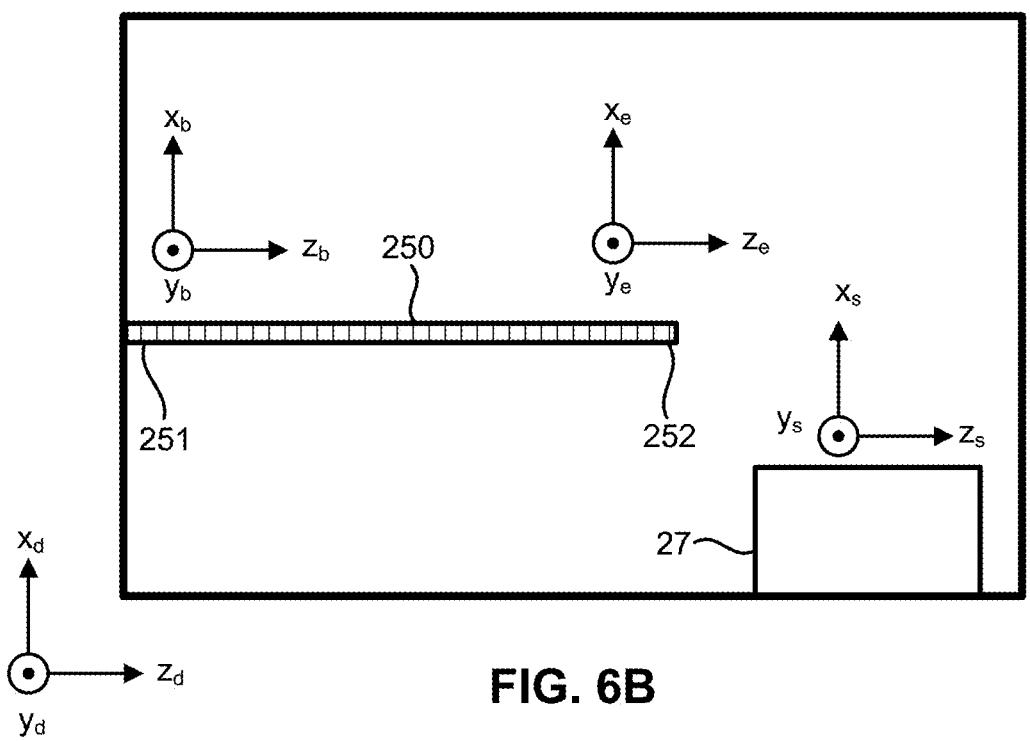

The flow then moves to block B515, where the system controller 11 controls the C-arm scanner 31 to capture an X-ray image (e.g., a fluoroscopic image) of the tubular flexible body 250, the radiolucent holder 36 (which is transparent to X-rays), and the position-tracking device 27. Then, in block B520, the X-ray image is used to determine whether, in the x-z plane, the z axes ($z_b$ and $z_e$) of the proximal end 251 of the tubular flexible body 250 and of the distal end 252 of the tubular flexible body 250 are aligned with the z axis (Z) of the C-arm scanner 31. Additionally, the X-ray image is used to determine whether, in the x-z plane, the z axis ($z_s$) of the position-tracking device 27 is aligned with the z axis ($z_d$) of the C-arm scanner 31. For example, FIGS. 6A-B illustrate embodiments of X-ray images of the tubular flexible body 250 and the position-tracking device 27. Because the radiolucent holder 36 is transparent to X-rays, the radiolucent holder 36 not visible. In FIG. 6A, the z axes ($z_b$ and $z_e$) of the proximal end 251 and the distal end 252 of the tubular flexible body 250 and the z axis(s) of the position-tracking device 27 are not aligned with the z axis ($z_d$) of the C-arm scanner 31.

If at least one of the z axes of the proximal end 251, the distal end 252, and the position-tracking device 27 is not aligned with the z axis ($z_d$) of the C-arm scanner 31 (B520=No), then the flow moves to block B525. In block B525, the position of the proximal end 251, the position of the distal end 252, or the position of the position-tracking device 27 is adjusted. For example, the position of any of these members (the proximal end 251, the distal end 252, or the position-tracking device 27) that is not aligned with the z axis of the C-arm scanner 31 may be adjusted. During the adjusting, one or more of the proximal end 251, the distal end 252, and the position-tracking device 27 may be rotated around the gravitational axis (the y axis) and in the plane defined by the x and z axes. And the flow then returns to block B515, where the C-arm scanner 31 captures another X-ray image of the tubular flexible body 250, the radiolucent holder 36, and the position-tracking device 27.

For example, after the capture of the X-ray image in FIG. 6A, and before the capture of the X-ray image in FIG. 6B, the tubular flexible body 250 and the position-tracking device 27 are rotated about the gravitational axis (the y axes) and in the plane defined by the x and z axes. Thus, in the X-ray image in FIG. 6B, the z axes ($z_b$ and $z_e$) of the proximal end 251 and the distal end 252 of the tubular flexible body 250 and the z axis ($z_s$) of the position-tracking device 27 are aligned with the z axis ($z_d$) of the C-arm scanner 31.

If in block B520 the z axes of the proximal end 251, the distal end 252, and the position-tracking device 27 are all aligned with the z axis of the C-arm scanner 31 (B520=Yes), then the flow proceeds to block B530.

Figure 7:
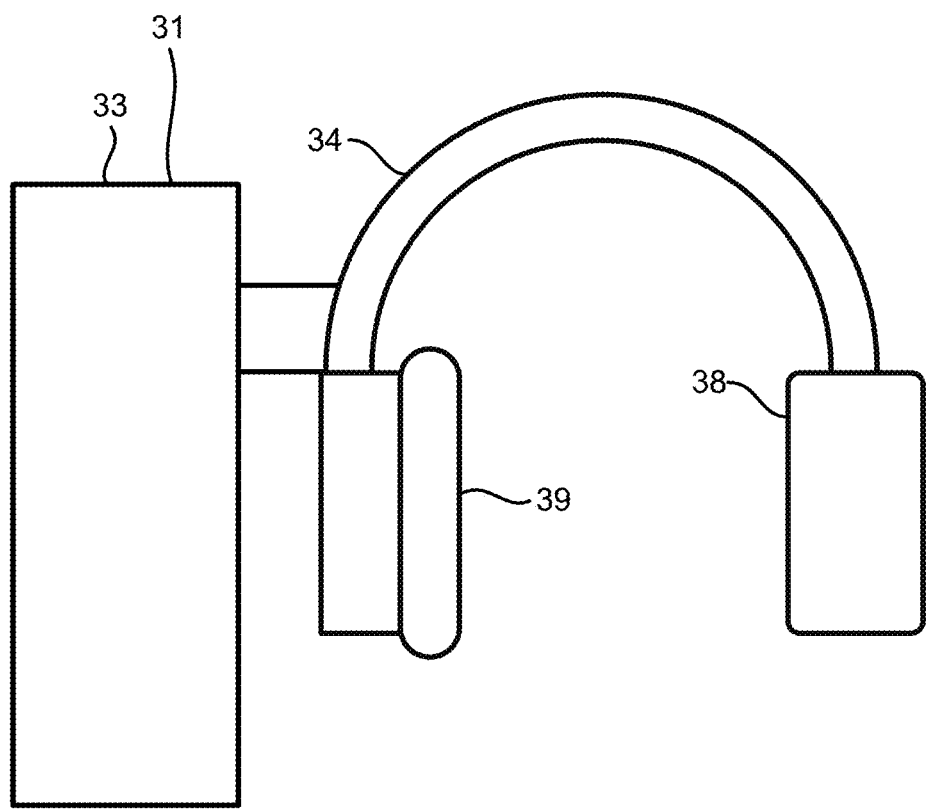
FIG. 7 illustrates an example embodiment of a C-arm scanner that has a C-arm in the 90 degree rotation angle.

In block B530, the system controller 11 controls the C-arm 34 of the C-arm scanner 31 to move to the 90 degree rotation angle. For example, FIG. 7 illustrates an example embodiment of a C-arm 34 that is in the 90 degree rotation angle. The C-arm 34 has been rotated by 90 degrees relative to the C-arm 34 in FIGS. 1 and 4.

The flow then advances to block B535, where the system controller 11 controls the C-arm scanner 31 to capture an X-ray image of the tubular flexible body 250, the radiolucent holder 36, and the position-tracking device 27. Then, in block B540, the X-ray image is used to determine whether, in the y-z plane, the z axes ($z_b$ and $z_e$) of the proximal end 251 of the tubular flexible body 250 and of the distal end 252 of the tubular flexible body 250 are aligned with the z axis ($z_d$) of the C-arm scanner 31. Additionally, the X-ray image is used to determine whether, in the y-z plane, the z axis ($z_s$) of the position-tracking device 27 is aligned with the z axis (Z) of the C-arm scanner 31.

If at least one of the z axes of the proximal end 251, the distal end 252, and the position-tracking device 27 is not aligned with the z axis ($z_d$) of the C-arm scanner 31 (B540=No), the flow moves to block B545. In block B545, the position of the proximal end 251, the position of the distal end 252, or the position of the position-tracking device 27 is adjusted. For example, the position of any of these members (the proximal end 251, the distal end 252, or the position-tracking device 27) that is not aligned with the z axis of the C-arm scanner 31 may be adjusted. During the adjusting, one or more of the proximal end 251, the distal end 252, and the position-tracking device 27 may be rotated around the x axis and in the plane defined by the y and z axes. And the flow then returns to block B535, where the C-arm scanner 31 captures another X-ray image of the tubular flexible body 250, the radiolucent holder 36, and the position-tracking device 27.

If in block B540 the z axes of the proximal end 251, the distal end 252, and the position-tracking device 27 are all aligned with the z axis of the C-arm scanner 31 (B540=Yes), then the flow proceeds to block B550.

Also, because the level gauges can be used to align the z axes of the proximal end 251, the distal end 252, and the position-tracking device 27 with the z axis of the C-arm scanner 31, some embodiments omit blocks B535-B545.

In block B550, calibration information is stored (e.g., stored by a system controller 11, stored by a bendable-device controller 21). The calibration information can be used if the z axes of the proximal end 251, the distal end 252, the position-tracking device 27, and the C-arm scanner 31 are not adequately aligned (e.g., the angle between two z axes is not less than a threshold). The calibration information indicates rotations between one or more of the reference frames of the proximal end 251, the distal end 252, the position-tracking device 27, and the C-arm scanner 31. Thus, a user or device (e.g., a system controller 11, a bendable-device controller 21) can use the calibration information to make minor adjustments to the mappings between reference frames. Also, some embodiments omit block B550.

Finally, the flow ends in block B555.

Figure 8:
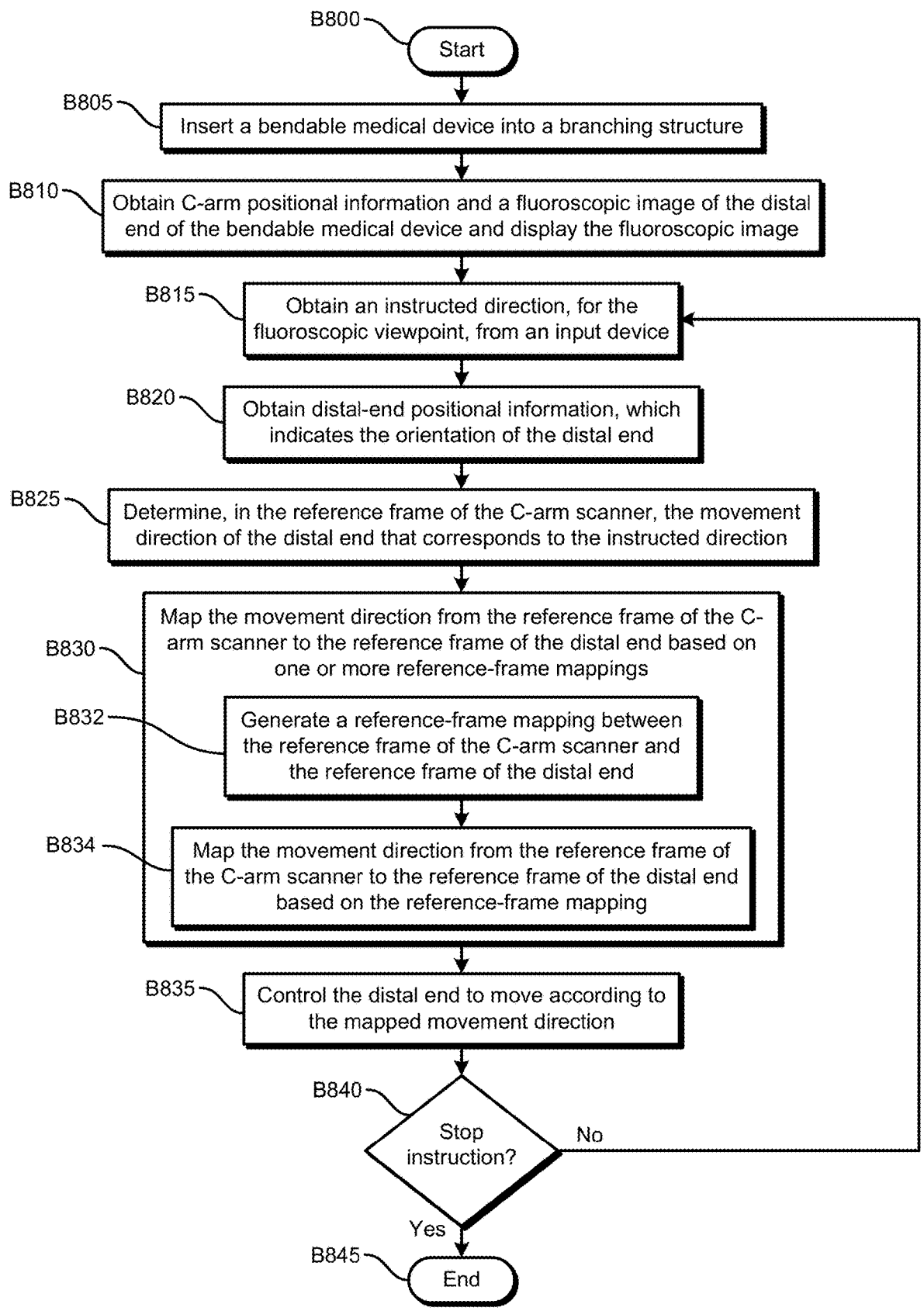
FIG. 8 illustrates an example embodiment of an operational flow for controlling a bendable medical device.

FIG. 8 illustrates an example embodiment of an operational flow for controlling a bendable medical device. Although this operational flow; the operational flows in FIGS. 11, 12, 14, 16, 18, 20, and 22; and some of the operations in FIG. 23 are performed by a system controller 11, some embodiments of these operational flows and operations are performed by two or more system controllers 11, by one or more bendable-device controllers 21, by one or more system controllers 11 and one or more bendable-device controllers 21 that operate together, or by one or more other specially-configured computing devices.

The flow starts in block B800 and then moves to block B805, where a system controller 11 controls the insertion of a bendable medical device 24 into a branching structure.

The flow then moves to block B810, where the system controller 11 obtains a fluoroscopic image of the distal end 252 of the bendable medical device 24 from a C-arm scanner 31 and displays the fluoroscopic image of the distal end 252. Also, the system controller 11 obtains C-arm positional information, which indicates the orientation (e.g., rotation angle) of the C-arm 34 when the fluoroscopic image was captured by the C-arm scanner 31.

Next, in block B815, the system controller 11 obtains an instructed direction (which may be included in a directional instruction), for the fluoroscopic viewpoint, from an input device. For example, in some embodiments the instructed direction may be left, right, up, or down. Also, the fluoroscopic viewpoint is defined in the reference frame $\{S_d\}$ of the C-arm scanner 31.

The flow then moves to block B820, where the system controller 11 obtains distal-end positional information, which indicates the orientation (and, in some embodiments, the location) of the distal end 252. The distal-end positional information may be obtained from the bendable medical device 24 (e.g., based on forward kinematics) or from a position-tracking system (which includes a position-tracking device 27 and position sensors 245). Also, the distal-end positional information may be defined in an intermediate reference frame, such as the reference frame $\{S_b\}$ of the proximal end 251 and the reference frame $\{S_s\}$ of the position-tracking system.

The flow then advances to block B825, where the system controller 11 determines, in the reference frame $\{S_d\}$ of the C-arm scanner 31, the movement direction of the distal end 252 that corresponds to the instructed direction. In some embodiments, the movement direction lies entirely in an image plane of the fluoroscopic image. The image plane is a subspace of the reference frame $\{S_d\}$ of the C-arm scanner 31, and, in some embodiments, the image plane may be defined by two axes of the reference frame $\{S_d\}$ of the C-arm scanner 31. For example, in FIGS. 3 and 4, the image plane is the subspace (plane) that is defined by the x axis ($x_d$) and the z axis ($z_d$) of the reference frame $\{S_d\}$ of the C-arm scanner 31. Also, if the movement direction lies entirely in the image plane (the $x_d$-$z_d$ plane), then the y-axis component (the component along ($y_d$)) of the movement direction would be zero in the reference frame $\{S_d\}$ of the C-arm scanner 31. Accordingly, in some embodiments, determining the movement direction in the reference frame $\{S_d\}$ of the C-arm scanner 31 requires only determining the movement direction in the image plane.

Figure 9A:
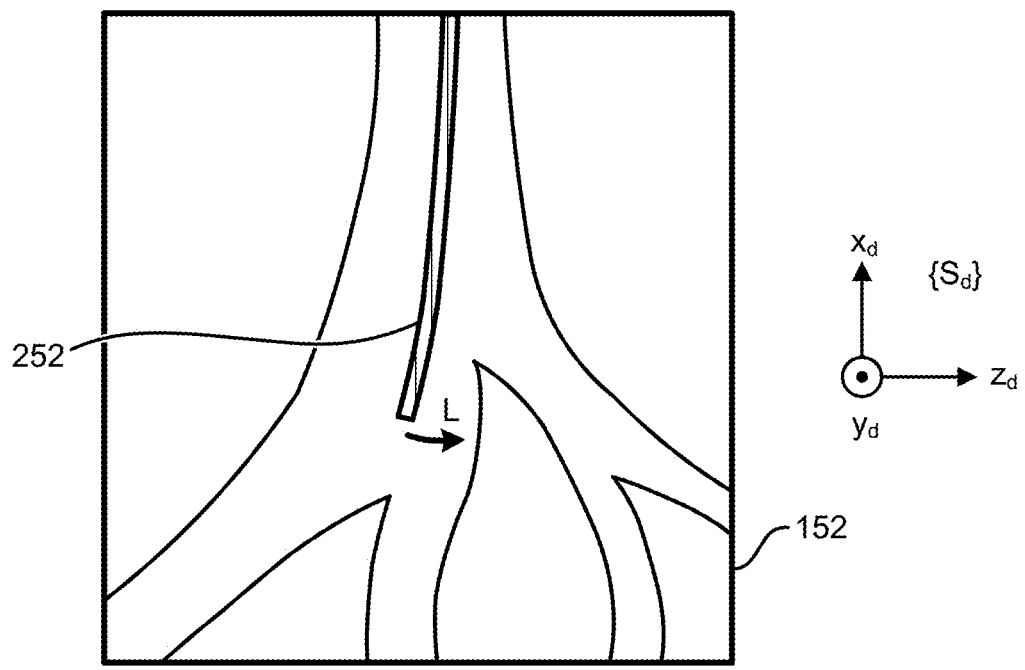
FIG. 9A illustrates an example embodiment of a fluoroscopic image.

The instructed direction may be defined relative to the orientation of the distal end 252 (e.g., defined in the endoscopic viewpoint). For example, if the instructed direction is left, left may be defined as left according to the orientation of the distal end 252. Thus, the system controller 11 may determine the orientation of the distal end 252 in the fluoroscopic image and then determine the corresponding direction of the instructed direction in the reference frame $\{S_d\}$ (e.g., in the image plane) of the C-arm scanner 31 (which is also the reference frame of the fluoroscopic viewpoint) based on the orientation of the distal end 252. The orientation of the distal end 252 may be determined based on computer-vision analysis of the fluoroscopic image or based on the distal-end positional information, which was obtained in block B820. For example, FIG. 9A illustrates an example embodiment of a fluoroscopic image 152. In this fluoroscopic image 152, the instructed direction is left. Also, left is based on the orientation of the distal end 252. Thus, in this example, the movement direction in the image plane (which is in the reference frame $\{S_d\}$ of the C-arm scanner 31) is approximately the $+z_d$ direction.

Also, the instructed direction may be defined relative to a viewer's perspective of the fluoroscopic image. Thus, if the instructed direction is "right," right may be defined as movement in the direction that appears to be right to a viewer (viewer's right) of the fluoroscopic image. For example, if the instructed direction is defined relative to a viewer's perspective, then in FIG. 9A, if the instructed direction was "right," the movement direction in the image plane would also be approximately the $+z_d$ direction.

Next, in block B830, the system controller 11 maps the movement direction from the reference frame $\{S_d\}$ of the C-arm scanner 31 to the reference frame $\{S_e\}$ of the distal end 252 based on one or more reference-frame mappings. In this embodiment, block B830 includes blocks B832 and B834.

In block B832, the system controller 11 generates a reference-frame mapping (frame mapping) between the reference frame $\{S_d\}$ of the C-arm scanner 31 and the reference frame $\{S_e\}$ of the distal end 252 based on one or more intermediate reference frames (the reference frame $\{S_b\}$ of the proximal end 251, the reference frame $\{S_s\}$ of the position-tracking system). For example, a reference-frame mapping may be a transformation that maps orientations between reference frames, such as a rotation matrix that describes the orientations of a reference frame relative to another reference frame. In the following description, $^AR_B$ is a rotation matrix (which is a reference-frame mapping) that describes the orientation of reference frame $\{S_B\}$ relative to reference frame $\{S_A\}$, which also describes the orientation of reference frame $\{S_A\}$ relative to reference frame $\{S_B\}$. Thus, rotation matrix $^AR_B$ can be used to map the orientation of reference frame $\{S_B\}$ to reference frame $\{S_A\}$ and vice versa.

When the C-arm 34 is rotated on the z-axis of the C-arm scanner 31, rotation matrix $^bR_d$, which is a rotation matrix that describes the orientation of the reference frame $\{S_d\}$ of the C-arm scanner 31 relative to the reference frame $\{S_b\}$ of the proximal end 251 (which is an intermediate reference frame in this example), can be calculated based on the rotation angle of the C-arm 34.

Figure 10A:
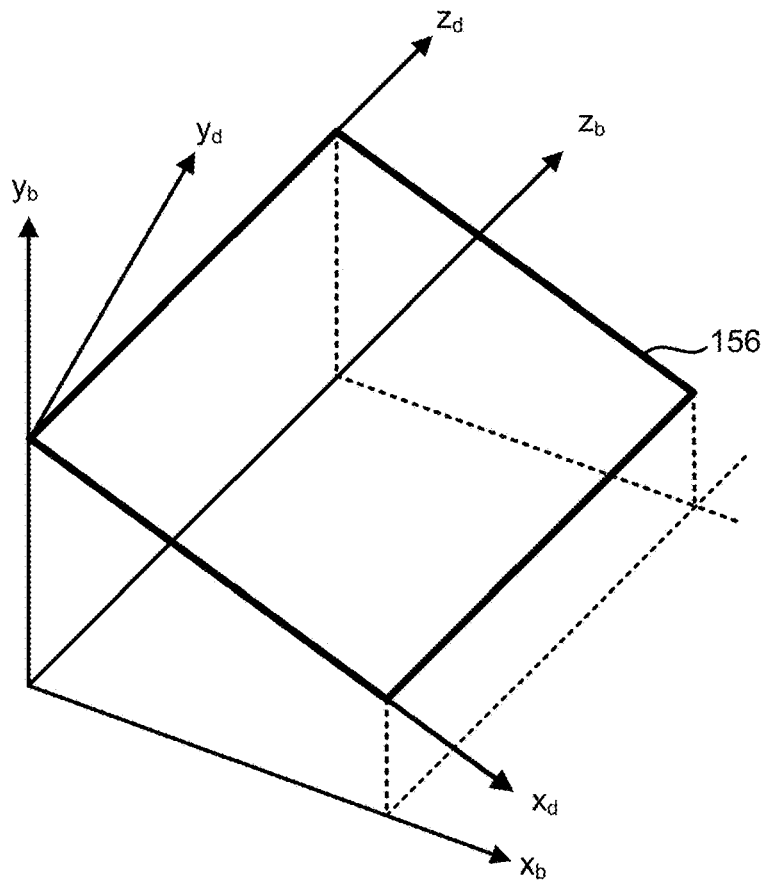
FIG. 10A illustrates an example of an image plane and the rotation of the reference frame of a C-arm scanner relative to an intermediate reference frame.

For example, FIG. 10A illustrates an example of an image plane 156 and the rotation of the reference frame $\{S_d\}$ of a C-arm scanner 31 relative to an intermediate reference frame (which is a reference frame $\{S_b\}$ of a proximal end 251 in this example). Note that, to simplify the illustrations in FIGS. 10A and 10B, the −x axes and +x axes have been reversed relative to FIGS. 3, 4, 6A, and 6B. As shown in FIG. 10A, if the z-axes, x-axes, and y-axes of the reference frame $\{S_d\}$ of the C-arm scanner 31 and the reference frame $\{S_b\}$ of the proximal end 251 are aligned during calibration, then the reference frame $\{S_d\}$ of the C-arm scanner 31 may be rotated, relative to the reference frame $\{S_b\}$ of the proximal end 251, around only the z axes. Accordingly, based on the rotation angle of the C-arm 34, the system controller 11 can calculate rotation matrix $^bR_d$. Also, relative to the reference frame $\{S_b\}$ of the proximal end 251, the image plane 156 is rotated around only the z axis (i.e., there is no rotation around either of the x and y axes).

Figure 10B:
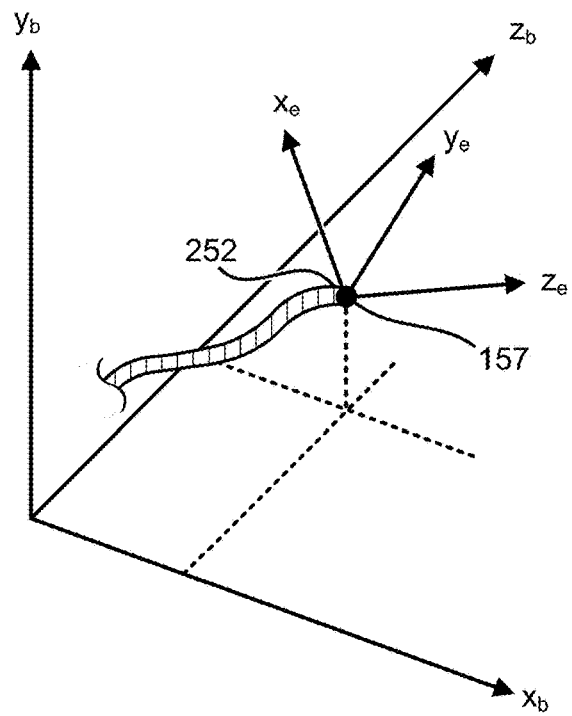
FIG. 10B illustrates an example of a location and an orientation of a distal end of a bendable medical device relative to an intermediate reference frame.

Additionally, when the tubular flexible body 250 is bent, rotation matrix $^eR_b$, which is a rotation matrix that describes the orientation of the reference frame $\{S_b\}$ of the proximal end 251 relative to the reference frame $\{S_e\}$ of the distal end 252, may be calculated. For example, FIG. 10B illustrates an example of a location 157 and orientation (which includes rotations about the $x_b$, $y_b$, and $z_b$ axes) of a distal end 252 in an intermediate reference frame (which is a reference frame $\{S_b\}$ of a proximal end 251 in this example). Because of the flexibility of the tubular flexible body 250, the distal end 252 may be capable of moving into almost any orientation in the reference frame $\{S_b\}$ of the proximal end 251. Thus, relative to the reference frame $\{S_b\}$ of the proximal end 251, the reference frame $\{S_e\}$ of the distal end 252 in FIG. 10B can be rotated around multiple axes. And, if the bendable medical device 24 generates positional information that indicates the location 157 and the orientation of the distal end 252 (e.g., based on forward kinematics), then the location 157 and the orientation can be defined in the reference frame $\{S_b\}$ of the proximal end 251. Because the orientation of the reference frame $\{S_e\}$ of the distal end 252 matches the orientation of the distal end 252, the orientation of both the reference frame $\{S_e\}$ of the distal end 252 and the reference frame $\{S_b\}$ of the proximal end 251 are known (and defined in the reference frame $\{S_b\}$ of the proximal end 251) and can be used to generate the rotation matrix $^eR_b$.

The rotation matrix $^eR_d$, which a rotation matrix that describes the orientation of the reference frame $\{S_d\}$ of the C-arm scanner 31 relative to the reference frame $\{S_e\}$ of the distal end 252, may be calculated as a product of the rotation matrix $^eR_b$ and the rotation matrix $^bR_d$. And, using the rotation matrix $^eR_d$, a movement direction of the distal end 251 in the reference frame $\{S_d\}$ of the C-arm scanner 31 can be mapped to a movement direction of the distal end 251 in the reference frame $\{S_e\}$ of the distal end 252, and vice versa.

Also, the one or more intermediate reference frames may include the reference frame $\{S_s\}$ of the position-tracking system. In such embodiments, rotation matrix $^eR_s$, which is a rotation matrix that describes the orientation of the reference frame $\{S_s\}$ of the position-tracking system relative to the reference frame $\{S_e\}$ of the distal end 252, can be obtained through the use of one or more sensors (e.g., positions sensors 245 in FIG. 25B) located at the distal end 252. Then rotation matrix $^{e}R_{d}$ may be obtained based on (e.g., as a product of) rotation matrix $^{e}R_{s}$, rotation matrix $^{s}R_{b}$, and rotation matrix $^{b}R_{d}$. And, in some embodiments, rotation matrix $^{e}R_{a}$ may be obtained based on (e.g., as a product of) rotation matrix $^{e}R_{s}$ and rotation matrix $^{s}R_{d}$.

The flow then moves to block B834, where the system controller 31 maps the movement direction from the reference frame $\{S_{d}\}$ of the C-arm scanner 31 to the reference frame $\{S_{e}\}$ of the distal end 252 based on the reference-frame mapping, which is rotation matrix $^{e}R_{d}$ (a rotation matrix that describes the orientation of the reference frame $\{S_{d}\}$ of the C-arm scanner 31 relative to the reference frame $\{S_{e}\}$ of the distal end 252) in the foregoing example.

Figure 9B:
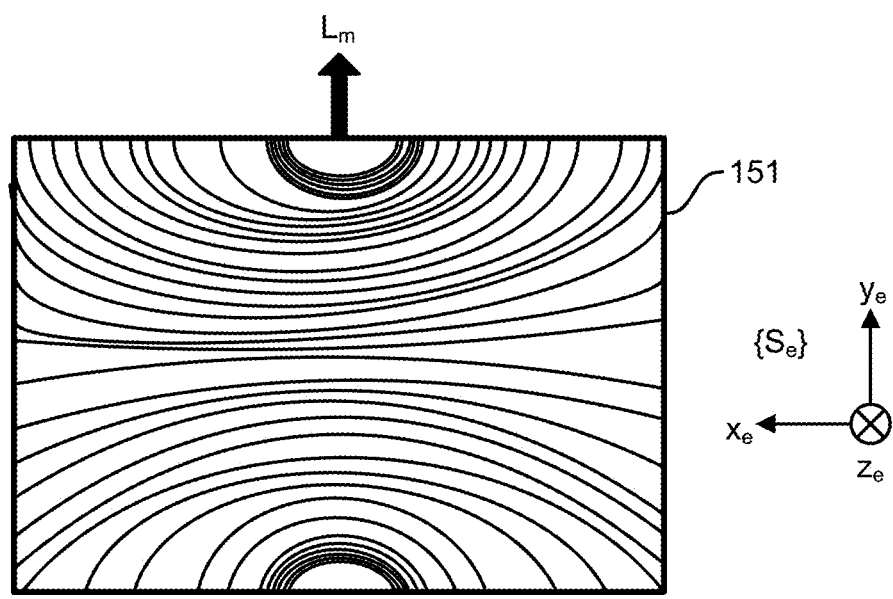
FIG. 9B illustrates an example embodiment of an endoscopic image.

For example, FIG. 9B illustrates an example embodiment of an endoscopic image 151. In this example, an instructed direction "left" is obtained, and the instructed direction is based on the orientation of the distal end 252 in the fluoroscopic image 152. Accordingly, the system controller 11 may use the generated reference-frame mapping (e.g., rotation matrix $^{d}R_{e}$) to map the movement direction from the reference frame $\{S_{d}\}$ of the C-arm scanner 31 to the reference frame $\{S_{e}\}$ of the distal end 252. In FIG. 9A, the distal end 252 is oriented in approximately the $-x_{d}$ direction in the reference frame $\{S_{d}\}$ of the C-arm scanner 31, and thus the movement direction in the reference frame $\{S_{d}\}$ of the C-arm scanner 31 is approximately the $+z_{d}$ direction. In the endoscopic image 151 in FIG. 9B, the mapped movement direction for "left" is indicated by Lm, which is upward. Thus, although the mapped "left" movement direction may not be "left" in the reference frame $\{S_{e}\}$ of the distal end 252 (the reference frame of the endoscopic viewpoint), the mapped "left" movement direction is the direction that the distal end 252 moves to move (e.g., turn) left in the fluoroscopic image 152 in FIG. 9A, which is defined in the reference frame $\{S_{d}\}$ of the C-arm scanner 31 (the reference frame of the fluoroscopic viewpoint).

Also, in block B830, instead of generating the reference-frame mapping (frame mapping) between the reference frame $\{S_{d}\}$ of the C-arm scanner 31 and the reference frame $\{S_{e}\}$ of the distal end 252 and mapping the movement direction from the reference frame $\{S_{d}\}$ of the C-arm scanner 31 to the reference frame $\{S_{e}\}$ of the distal end 252 based on the reference-frame mapping, some embodiments of the system controller 11 generate reference-frame mappings between the reference frame $\{S_{d}\}$ of the C-arm scanner 31 and an intermediate reference frame and between the intermediate reference frame and the reference frame $\{S_{e}\}$ of the distal end 252. This may also include generating one or more mappings between intermediate reference frames. Then these embodiments of the system controller 11 map the movement direction from the reference frame $\{S_{d}\}$ of the C-arm scanner 31 to an intermediate reference frame and then map the movement direction from the intermediate reference frame to the reference frame $\{S_{e}\}$ of the distal end 252. This may also include at least one mapping of the movement direction from one intermediate reference frame to another intermediate reference frame.

Next, in block B835, the system controller 11 controls the distal end 252 to move according to the mapped movement direction.

The flow then moves to block B840, where the system controller 11 determines whether a stop instruction has been obtained. If a stop instruction has not been obtained (B840=No), then the flow returns to block B815, where the system controller 11 obtains another instructed direction. If a stop instruction has been obtained (B840=Yes), then the flow ends in block B845.

Figure 11:
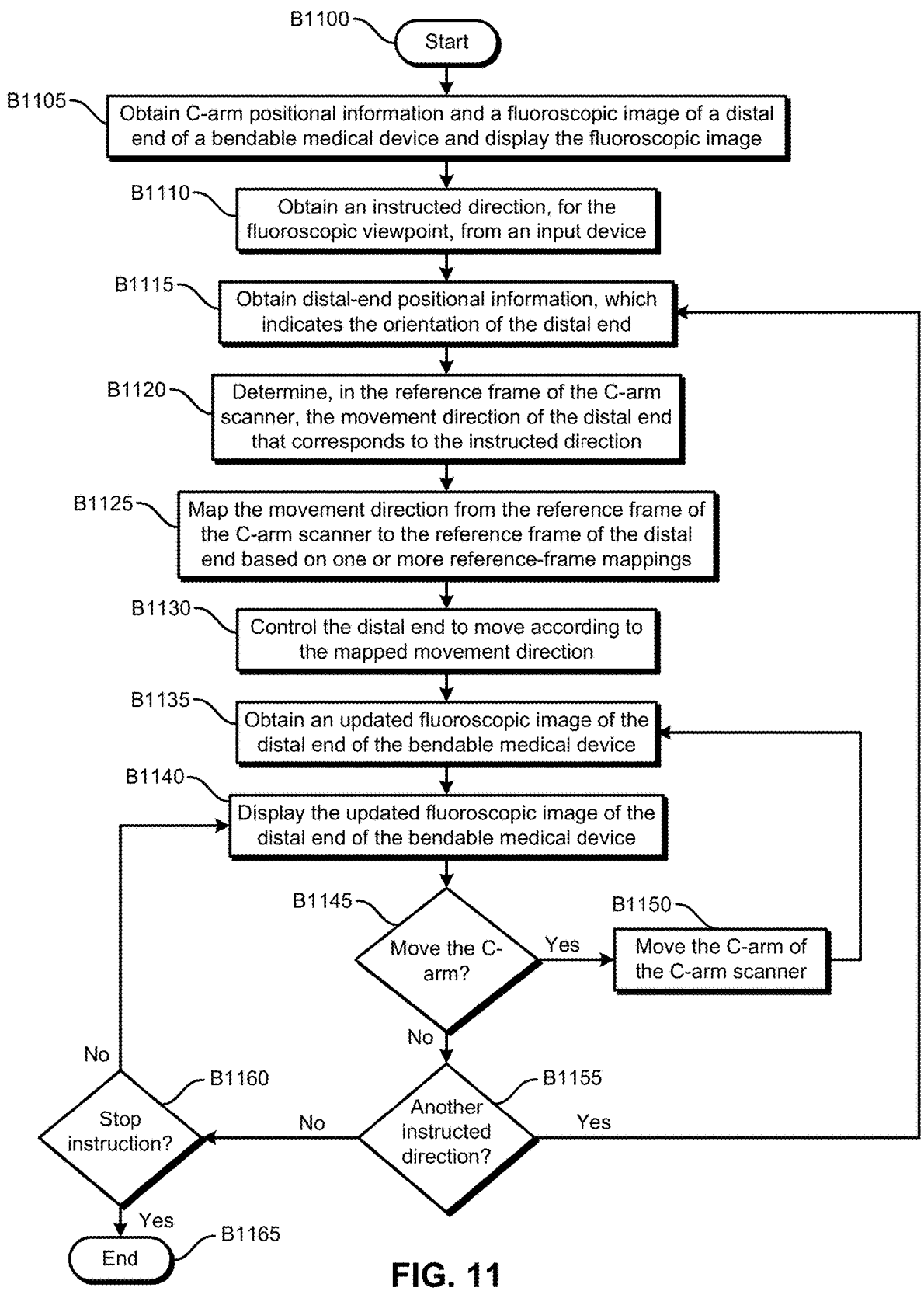
FIG. 11 illustrates an example embodiment of an operational flow for controlling a bendable medical device.

FIG. 11 illustrates an example embodiment of an operational flow for controlling a bendable medical device.

The flow starts in block B1100 and then moves to block B1105, where a system controller 11 obtains a fluoroscopic image of a distal end 252 of a bendable medical device 24 from a C-arm scanner 31 and controls the display of the fluoroscopic image. Also, system controller 11 obtains C-arm positional information that indicates the rotation angle of the C-arm 34 when the fluoroscopic image was captured by the C-arm scanner 31.

Next, in block B1110, the system controller 11 obtains an instructed direction, for the fluoroscopic viewpoint, from an input device.

The flow then advances to block B1115, where the system controller 11 obtains distal-end positional information, which indicates the orientation (and, in some embodiments, the location) of the distal end 252.

The flow then advances to block B1120, where the system controller 11 determines, in the reference frame $\{S_{d}\}$ of the C-arm scanner 31, the movement direction of the distal end 252 that corresponds to the instructed direction.

Next, in block B1125, the system controller 11 maps the movement direction from the reference frame $\{S_{d}\}$ of the C-arm scanner 31 to the reference frame $\{S_{e}\}$ of the distal end 252 based on one or more reference-frame mappings (e.g., as described in block B830 (including blocks B832 and B834) in FIG. 8).

The flow then moves to block B1130, where the system controller 11 controls the distal end 252 to move according to the mapped movement direction.

Then the flow advances to block B1135, where the system controller 11 obtains an updated fluoroscopic image of the distal end 252 of the bendable medical device 24 from the C-arm scanner 31. The updated fluoroscopic image is a fluoroscopic image that is captured by the C-arm scanner 31 after the distal end 252 is moved in block B1130 or after the C-arm 34 is moved in block B1150 (described below). And the system controller 11 obtains C-arm positional information that indicates the rotation angle of the C-arm 34 when the updated fluoroscopic image was captured by the C-arm scanner 31. In block B1140, the system controller 11 controls the display of the updated fluoroscopic image of the distal end 252.

The flow then proceeds to block B1145, where the system controller 11 determines whether an instruction to move the C-arm 34 has been obtained. If an instruction to move the C-arm 34 has been obtained (B1145=Yes), then the flow moves to block B1150. In block B1150, the system controller 11 controls the C-arm 34 of the C-arm scanner 31 to move. And the flow then returns to block B1135.

If an instruction to move the C-arm 34 has not been obtained (B1145=No), then the flow moves to block B1155.

In block B1155, the system controller 11 determines whether another instructed direction for the fluoroscopic viewpoint has been obtained. If the system controller 11 determines that another instructed direction has been obtained (B1155=Yes), then the flow returns to block B1115. If the system controller 11 determines that another instructed direction has not been obtained (B1155=No), then the flow moves to block B1160.

In block B1160, the system controller 11 determines whether a stop instruction has been obtained. If a stop instruction has not been obtained (B1160=No), then the flow returns to block B1140, where the system controller 11 continues to control the display of the updated fluoroscopic image of the distal end 252. If a stop instruction has been obtained (B1160=Yes), then the flow ends in block B1165.

Figure 12:
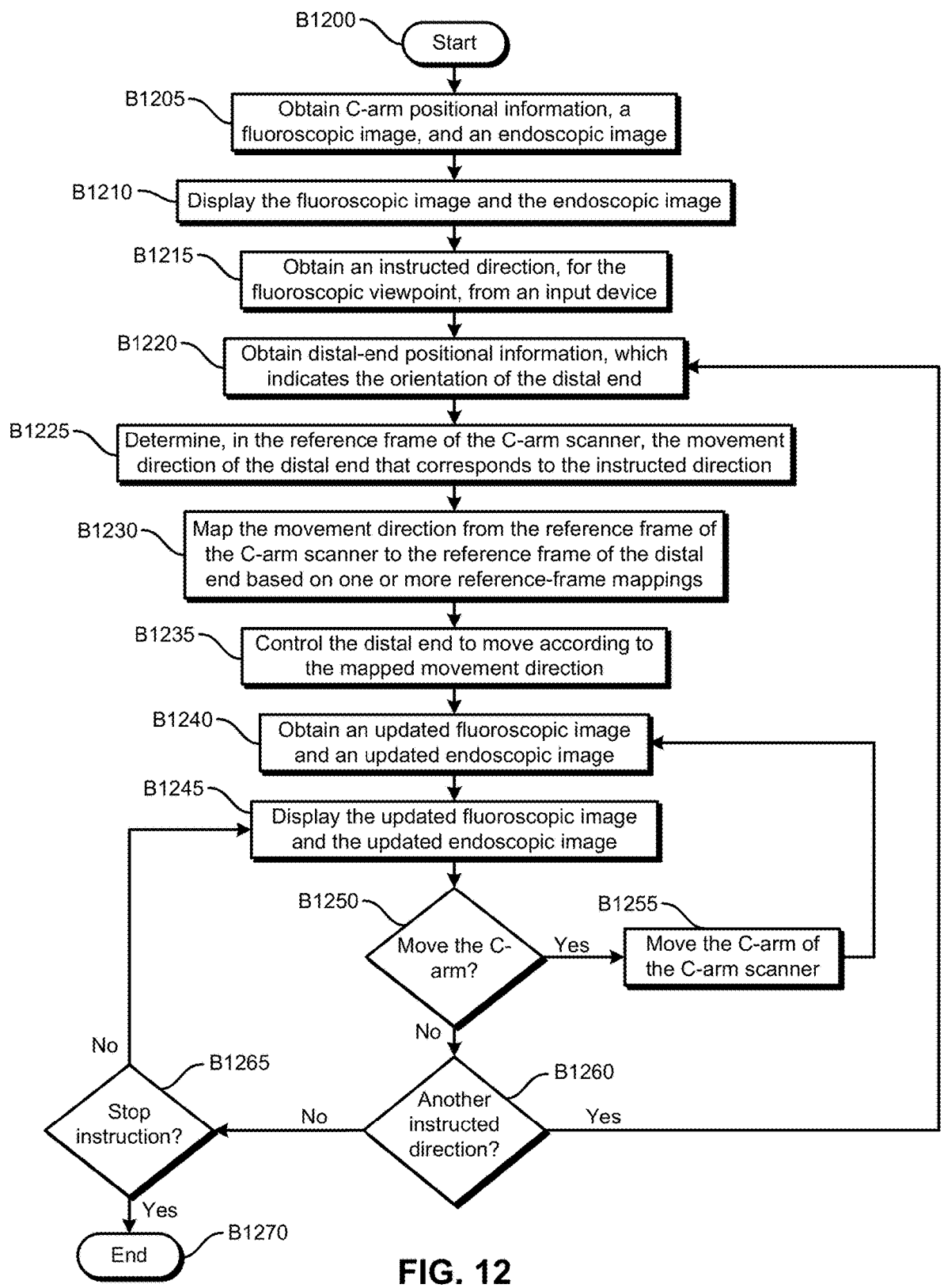
FIG. 12 illustrates an example embodiment of an operational flow for controlling a bendable medical device.

FIG. 12 illustrates an example embodiment of an operational flow for controlling a bendable medical device. The flow starts in block B1200 and then moves to block B1205, where a system controller 11 obtains a fluoroscopic image of a distal end 252 of a bendable medical device 24 that was generated by a C-arm scanner 31 and obtains an endoscopic image that was captured from the distal end 252 of the bendable medical device 24. Also, along with the first fluoroscopic image, the system controller 11 obtains C-arm positional information.

The flow then moves to block B1210, where the system controller 11 controls the display of the fluoroscopic image and the endoscopic image. For example, FIG. 13 illustrates an example embodiment of a display device 15 that is displaying an endoscopic image 151 and a fluoroscopic image 152.

Next, in block B1215, the system controller 11 obtains an instructed direction, for the fluoroscopic viewpoint, from an input device 29. Some embodiments of medical systems include two or more input devices 29, of which one input device 29 may provide instructed directions for the endoscopic viewpoint and another input device 29 may provide instructed directions for the fluoroscopic viewpoint.

Figure 13:
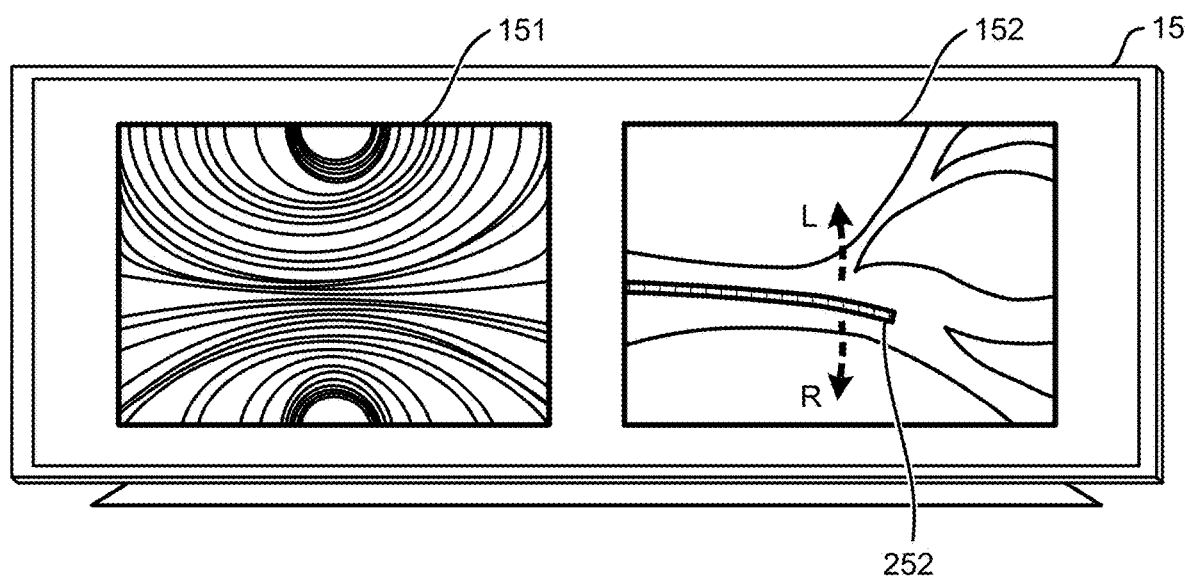
FIG. 13 illustrates an example embodiment of a display device that is displaying a fluoroscopic image and an endoscopic image.
Figure 13:
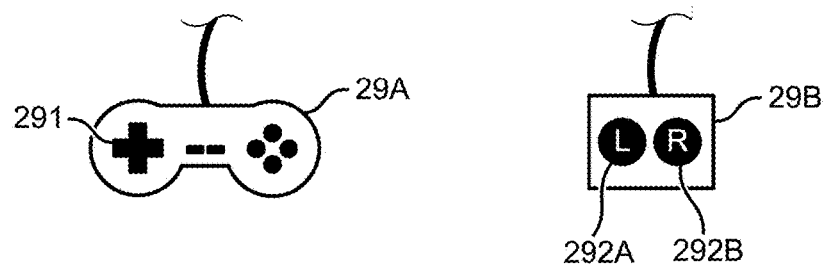

For example, FIG. 13 also illustrates two input devices 29. A first input device 29A is a control pad, and the directional pad 291 on the first input device 29A generates instructed directions for the endoscopic viewpoint. Thus, the system controller 11 interprets the instructed directions from the first input device 29A in the reference frame of the endoscopic viewpoint (the reference frame of the distal end 252). A second input device 29B generates instructed directions for the fluoroscopic viewpoint. The second input device 29B is a pad that includes two buttons: a "left" button 292A that issues a "left" instructed direction and a "right" button 292B that issues a "right" instructed direction. Accordingly, the system controller 11 interprets the instructed directions from the second input device 29B based on the reference frame of the fluoroscopic viewpoint (which is defined in the reference frame $\{S_d\}$ of the C-arm scanner). For example, the system controller 11 may interpret a "right" instructed direction from the second input device 29B to be an instruction to move the distal end 252 to the right relative to the orientation of the distal end 252 in the image plane of the fluoroscopic image 152. Although the display device 15 may not display any direction indicators (e.g., a left indicator, a right indicator) in the fluoroscopic image 152, FIG. 13 includes a left indicator L and a right indicator R. Additionally, in embodiments such as the embodiment that is illustrated in FIG. 13, the second input device 29B generates the instructed direction in block B1215.

The flow then advances to block B1220, where the system controller 11 obtains distal-end positional information, which indicates the orientation (and, in some embodiments, the location) of the distal end 252. The distal-end positional information may be obtained from the bendable medical device 24 or from a position-tracking system.

The flow then advances to block B1225, where the system controller 11 determines, in the reference frame $\{S_d\}$ of the C-arm scanner 31, the movement direction of the distal end 252 that corresponds to the instructed direction.

Next, in block B1230, the system controller 11 maps the movement direction from the reference frame $\{S_d\}$ of the C-arm scanner 31 to the reference frame $\{S_e\}$ of the distal end 252 based on one or more reference-frame mappings (e.g., as described in block B830 (including blocks B832 and B834) in FIG. 8).

Then, in block B1235, the system controller 11 controls the distal end 252 to move according to the mapped movement direction.

Then the flow advances to block B1240, where the system controller 11 obtains an updated fluoroscopic image of the distal end 252 that was generated by the C-arm scanner 31 and obtains an updated endoscopic image that was generated by the bendable medical device 24. Following, in block B1245, the system controller 11 controls the display of the updated fluoroscopic image and the display of the updated endoscopic image on a display device 15.

The flow then proceeds to block B1250, where the system controller 11 determines whether an instruction to move the C-arm 34 has been obtained. If an instruction to move the C-arm 34 has been obtained (B1250=Yes), then the flow moves to block B1255. In block B1255, the system controller 11 controls the C-arm 34 of the C-arm scanner 31 to move. And the flow then returns to block B1240.

If an instruction to move the C-arm 34 has not been obtained (B1250=No), then the flow moves to block B1260.

In block B1260, the system controller 11 determines whether another instructed direction for the fluoroscopic viewpoint has been obtained from the input device. If the system controller 11 determines that another instructed direction has been obtained (B1260=Yes), then the flow returns to block B1220. If the system controller 11 determines that another instructed direction has not been obtained (B1260=No), then the flow moves to block B1265.

In block B1265, the system controller 11 determines whether a stop instruction has been obtained. If a stop instruction has not been obtained (B1265=No), then the flow returns to block B1245, where the system controller 11 continues to control the display of the updated fluoroscopic image and the updated endoscopic image. If a stop instruction has been obtained (B1265=Yes), then the flow ends in block B1270.

Figure 14:
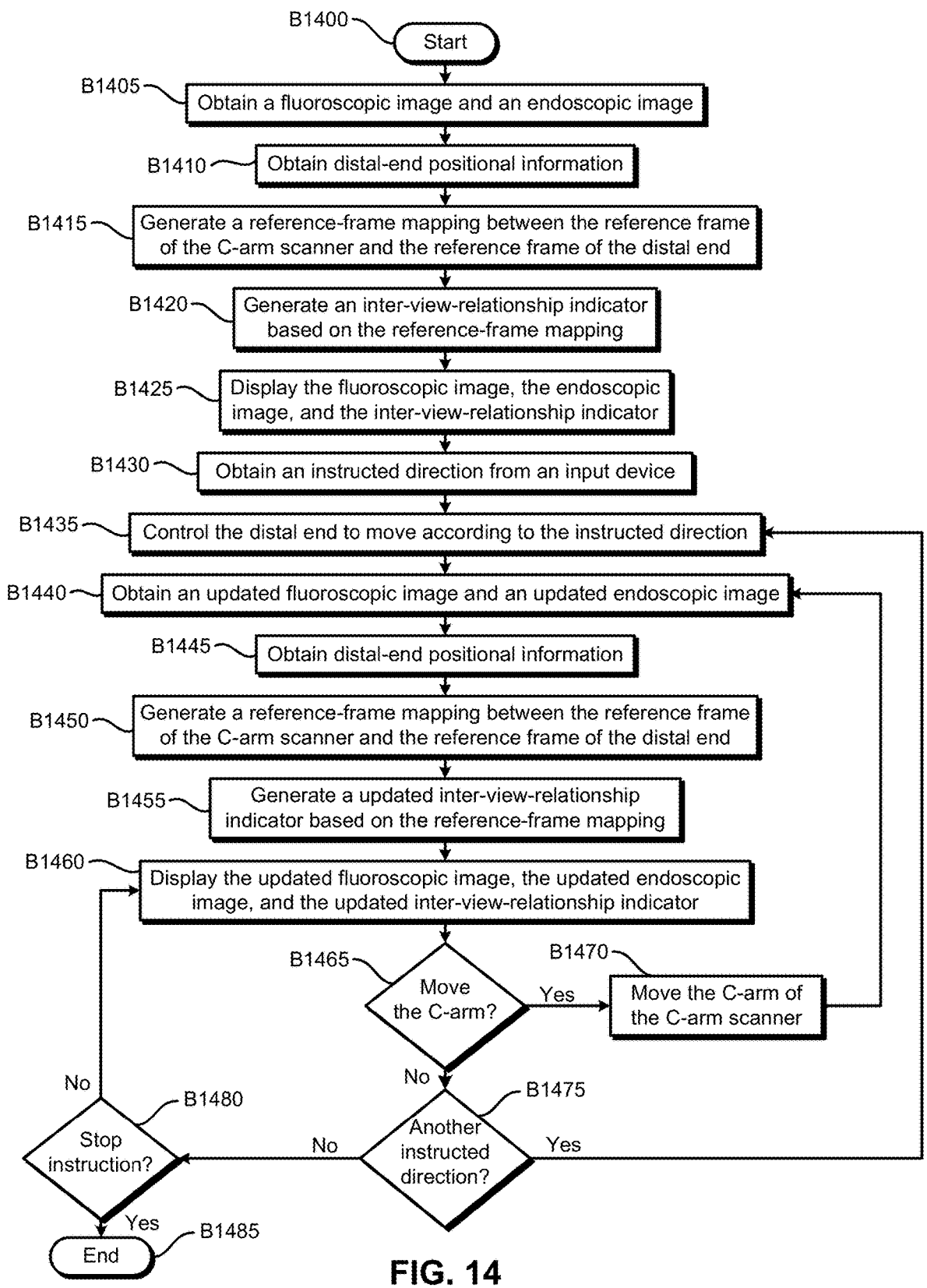
FIG. 14 illustrates an example embodiment of an operational flow for controlling a bendable medical device.

FIG. 14 illustrates an example embodiment of an operational flow for controlling a bendable medical device. The flow starts in block B1400 and then moves to block B1405, where a system controller 11 obtains a fluoroscopic image of a distal end 252 of a bendable medical device 24 and obtains an endoscopic image that was captured from the distal end 252. Also, the system controller 11 obtains C-arm positional information, which indicates the rotation angle of the C-arm 34 when the fluoroscopic image was captured by the C-arm scanner 31.

The flow then advances to block B1410, where the system controller 11 obtains distal-end positional information, which indicates the orientation (and, in some embodiments, the location) of the distal end 252. The distal-end positional information may be obtained from the bendable medical device 24 or from a position-tracking system (which may include a position-tracking device 27 and one or more position sensors 245).

The flow then moves to block B1415, where the system controller 11 generates a reference-frame mapping (frame mapping) between the reference frame $\{S_d\}$ of the C-arm scanner 31 and the reference frame $\{S_e\}$ of the distal end 252 based on one or more intermediate reference frames (e.g., the reference frame $\{S_b\}$ of the proximal end 251, the reference frame $\{S_s\}$ of the position-tracking system), on the C-arm positional information, and on the distal-end positional information (e.g., as described in block B832 in FIG. 8).

Next, in block B1420, the system controller 11 generate an inter-view-relationship indicator, which indicates the relationship between the endoscopic viewpoint and the fluoroscopic viewpoint, based on the reference-frame mapping. For example, the inter-view-relationship indicator may be an icon or arrow that indicates the orientation of the image plane of the fluoroscopic image relative to the image plane of the endoscopic image. And, in block B1425, the system controller 11 controls the display of the fluoroscopic image, the endoscopic image, and the inter-view-relationship indicator on a display device 15.

Figure 15A:
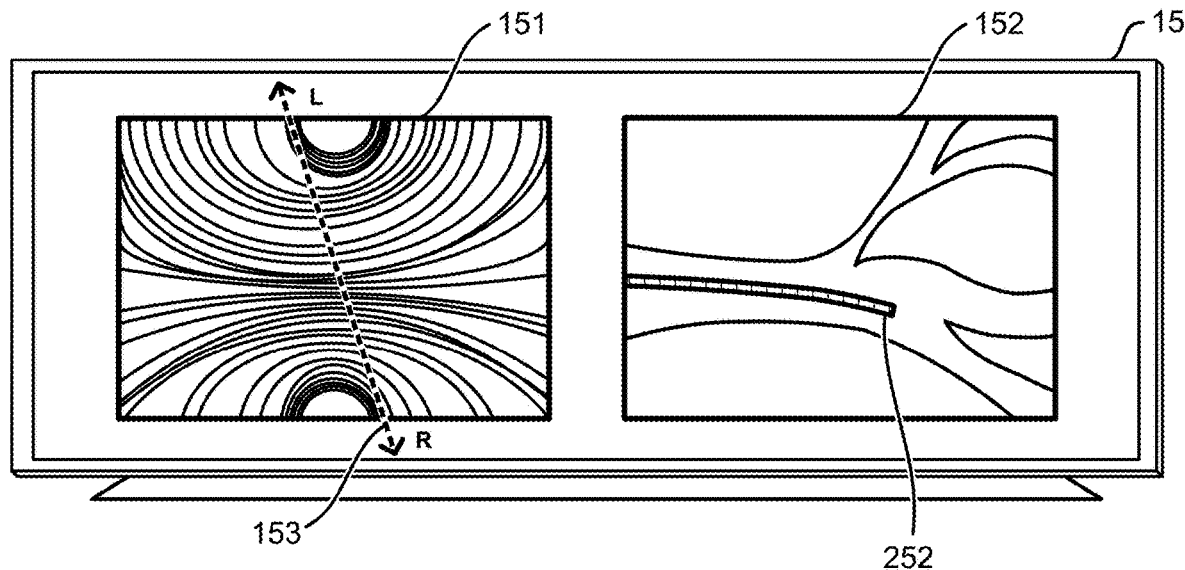
FIG. 15A illustrates an example embodiment of a display device that is displaying an endoscopic image, a fluoroscopic image, and an inter-view-relationship indicator.

For example, FIG. 15A illustrates an example embodiment of a display device 15 that is displaying an endoscopic image 151, a fluoroscopic image 152, and an inter-view-relationship indicator 153. In this embodiment, the inter-view-relationship indicator 153 is an arrow that is overlaid on the endoscopic image 151 and that indicates the relative orientation of the plane of the fluoroscopic image 152. Furthermore, the inter-view-relationship indicator 153 includes the character "L" and the character "R", which respectively indicate which directions are, in this embodiment, "left" and "right" in the fluoroscopic viewpoint. In this embodiment, "left" and "right" are based on the orientation of the distal end 252 in the image plane of the fluoroscopic image 152.

Figure 15B:
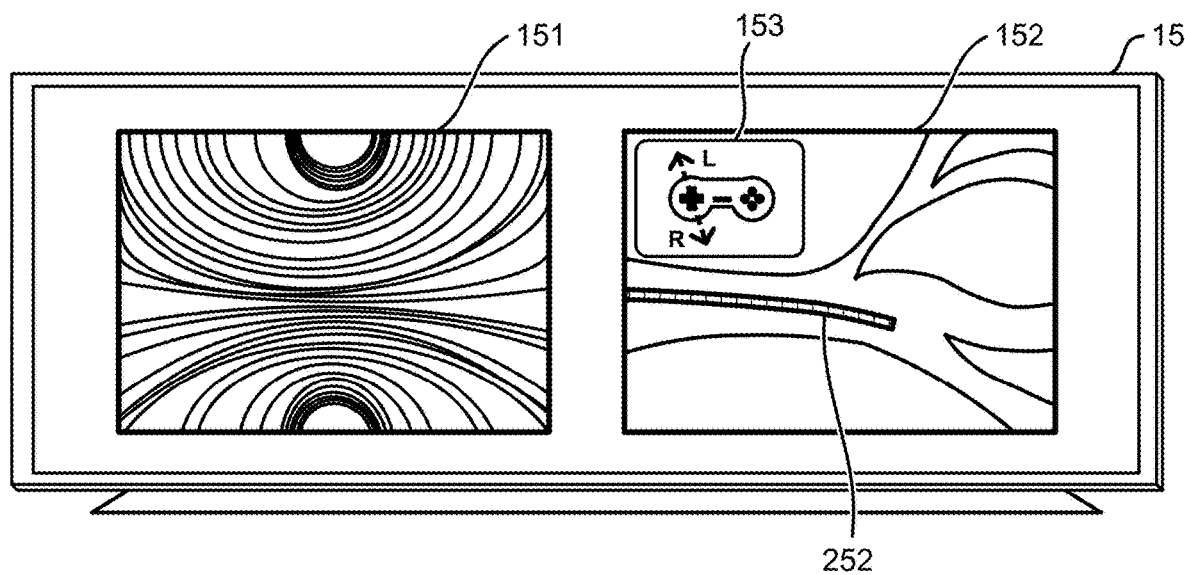
FIG. 15B illustrates an example embodiment of a display device that is displaying an endoscopic image, a fluoroscopic image, and an inter-view-relationship indicator.

Also for example, FIG. 15B illustrates an example embodiment of a display device 15 that is displaying an endoscopic image 151, a fluoroscopic image 152, and an inter-view-relationship indicator 153. In this embodiment, the inter-view-relationship indicator 153 includes an icon that has the appearance of a control pad. And the inter-view-relationship indicator 153 includes an arrow, the character "L", and the character "R", which indicate which directions on the control pad are, in this embodiment, "left" and "right" in the fluoroscopic image 152. Like the embodiment in FIG. 15A, in this embodiment, "left" and "right" are based on the orientation of the distal end 252 in the image plane of the fluoroscopic image 152. Thus, to move the distal end 252 to its left (in the orientation of the distal end 252) in the fluoroscopic image 152, a user can press the directional pad 291 of an input device 29 in the direction that is indicated as being "left" by the inter-view-relationship indicator 153.

Next, in block B1430, the system controller 11 obtains an instructed direction from an input device 29. And, in block B1435, the system controller 11 controls the distal end 252 to move according to the instructed direction. In this embodiment, block B1435 does not include a mapping of the instructed direction from one reference frame to another.

Then the flow advances to block B1440, where the system controller 11 obtains an updated fluoroscopic image of the distal end 252 of the bendable medical device 24 from the C-arm scanner 31 and obtains an updated endoscopic image from the bendable medical device 24. Also, the system controller 11 obtains C-arm positional information.

The flow then advances to block B1445, where the system controller 11 obtains distal-end positional information, which indicates the orientation (and, in some embodiments, the location) of the distal end 252.

The flow then moves to block B1450, where the system controller 11 generates a reference-frame mapping between the reference frame $\{S_d\}$ of the C-arm scanner 31 and the reference frame $\{S_e\}$ of the distal end 252 based on one or more intermediate reference frames (e.g., the reference frame $\{S_b\}$ of the proximal end 251, the reference frame $\{S_s\}$ of the position-tracking system), on the C-arm positional information, and on the distal-end positional information (for example, as described in block B832 in FIG. 8).

Next, in block B1455, the system controller 11 generate an updated inter-view-relationship indicator, which indicates the relationship between the endoscopic viewpoint of the updated endoscopic image and the fluoroscopic viewpoint of the updated fluoroscopic image, based on the reference-frame mapping that was generated in block B1450.

Then, in block B1460, the system controller 11 controls the display of the updated fluoroscopic image, the updated endoscopic image, and the updated inter-view-relationship indicator.

The flow then proceeds to block B1465, where the system controller 11 determines whether an instruction to move the C-arm 34 has been obtained. If an instruction to move the C-arm 34 has been obtained (B1465=Yes), then the flow moves to block B1470. In block B1470, the system controller 11 controls the C-arm 34 of the C-arm scanner 31 to move. And the flow then returns to block B1440.

If an instruction to move the C-arm 34 has not been obtained (B1465=No), then the flow moves to block B1475.

In block B1475, the system controller 11 determines whether another instructed direction has been obtained. If the system controller 11 determines that another instructed direction has been obtained (B1475=Yes), then the flow returns to block B1435. If the system controller 11 determines that another instructed direction has not been obtained (B1475=No), then the flow moves to block B1480.

In block B1480, the system controller 11 determines whether a stop instruction has been obtained. If a stop instruction has not been obtained (B1480=No), then the flow returns to block B1460, where the system controller 11 continues to control the display of the updated fluoroscopic image, the updated endoscopic image, and the updated inter-view-relationship indicator. If a stop instruction has been obtained (B1480=Yes), then the flow ends in block B1485.

Figure 16:
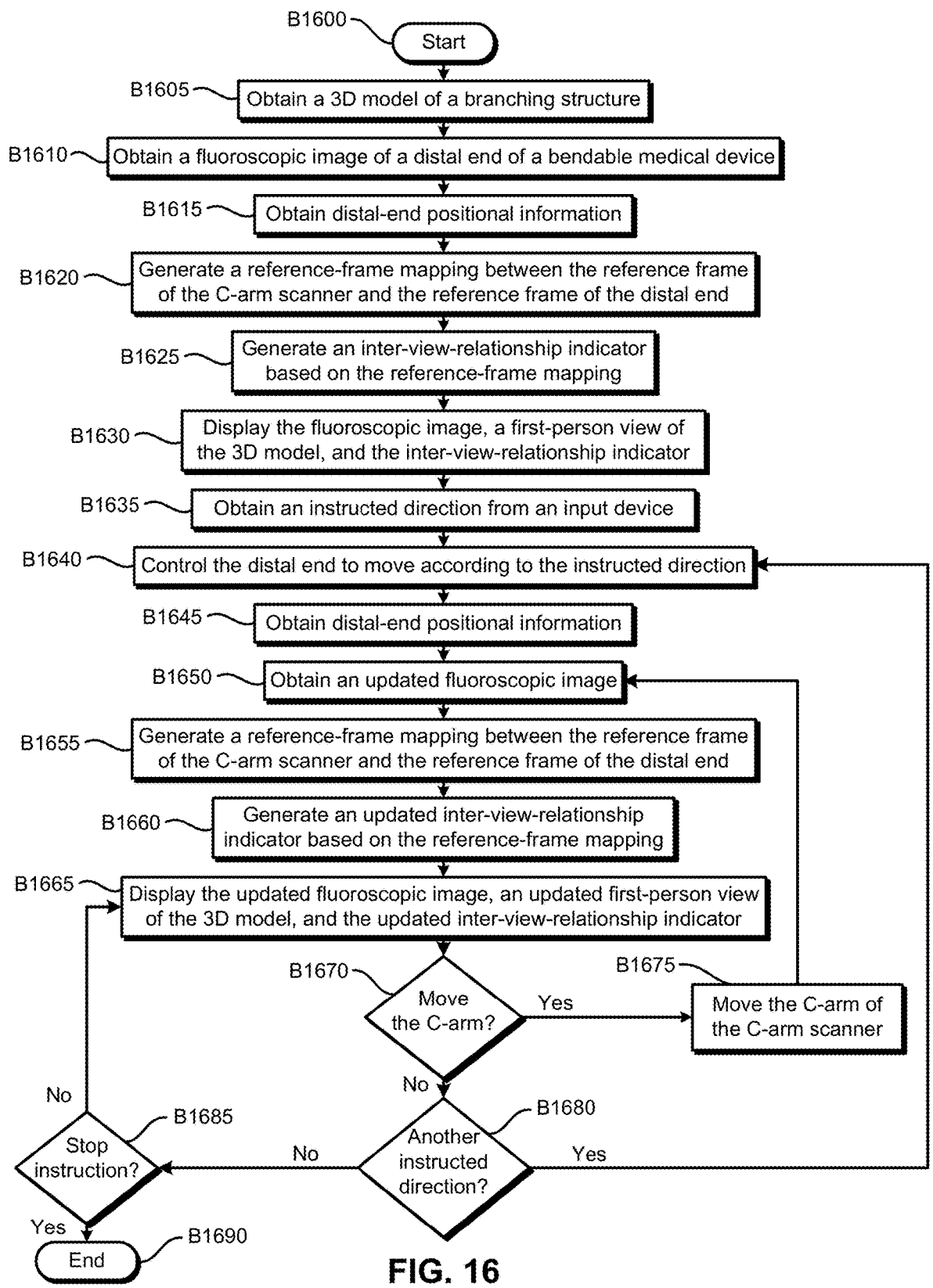
FIG. 16 illustrates an example embodiment of an operational flow for controlling a bendable medical device.

FIG. 16 illustrates an example embodiment of an operational flow for controlling a bendable medical device. The flow begins in block B1600 and then advances to block B1605, where a system controller 11 obtains (e.g., generates, retrieves, receives, acquires) a 3D model of a branching structure. The 3D model is a virtual model of the branching structure and may be generated from computed-tomography (CT) images of the branching structure.

Next, in block B1610, the system controller 11 obtains a fluoroscopic image of a distal end 252 of a bendable medical device 24, that has been inserted into the branching structure, from a C-arm scanner 31. Also, the system controller 11 obtains C-arm positional information.

The flow then advances to block B1615, where the system controller 11 obtains distal-end positional information, which indicates the orientation and the location of the distal end 252. The distal-end positional information may be obtained from the bendable medical device 24 or from a position-tracking system.

The flow then moves to block B1620, where the system controller 11 generates a reference-frame mapping between the reference frame $\{S_d\}$ of the C-arm scanner 31 and the reference frame $\{S_e\}$ of the distal end 252 based on one or more intermediate reference frames (e.g., the reference frame $\{S_b\}$ of the proximal end 251, the reference frame $\{S_s\}$ of the position-tracking system), on the C-arm positional information, and on the distal-end positional information. Additionally, the reference frame of the distal end 252 may be used as the reference frame of a first-person view of the 3D model, which shows the 3D model from the viewpoint of the distal end's location and orientation and which may simulate an endoscopic image.

Next, in block B1625, the system controller 11 generate an inter-view-relationship indicator, which indicates the relationship between the first-person view of the 3D model and the fluoroscopic image, based on the reference-frame mapping.

The flow then proceeds to block B1630, where the system controller 11 controls the display of the fluoroscopic image, the first-person view of the 3D model, and the inter-view-relationship indicator.

Figure 17:
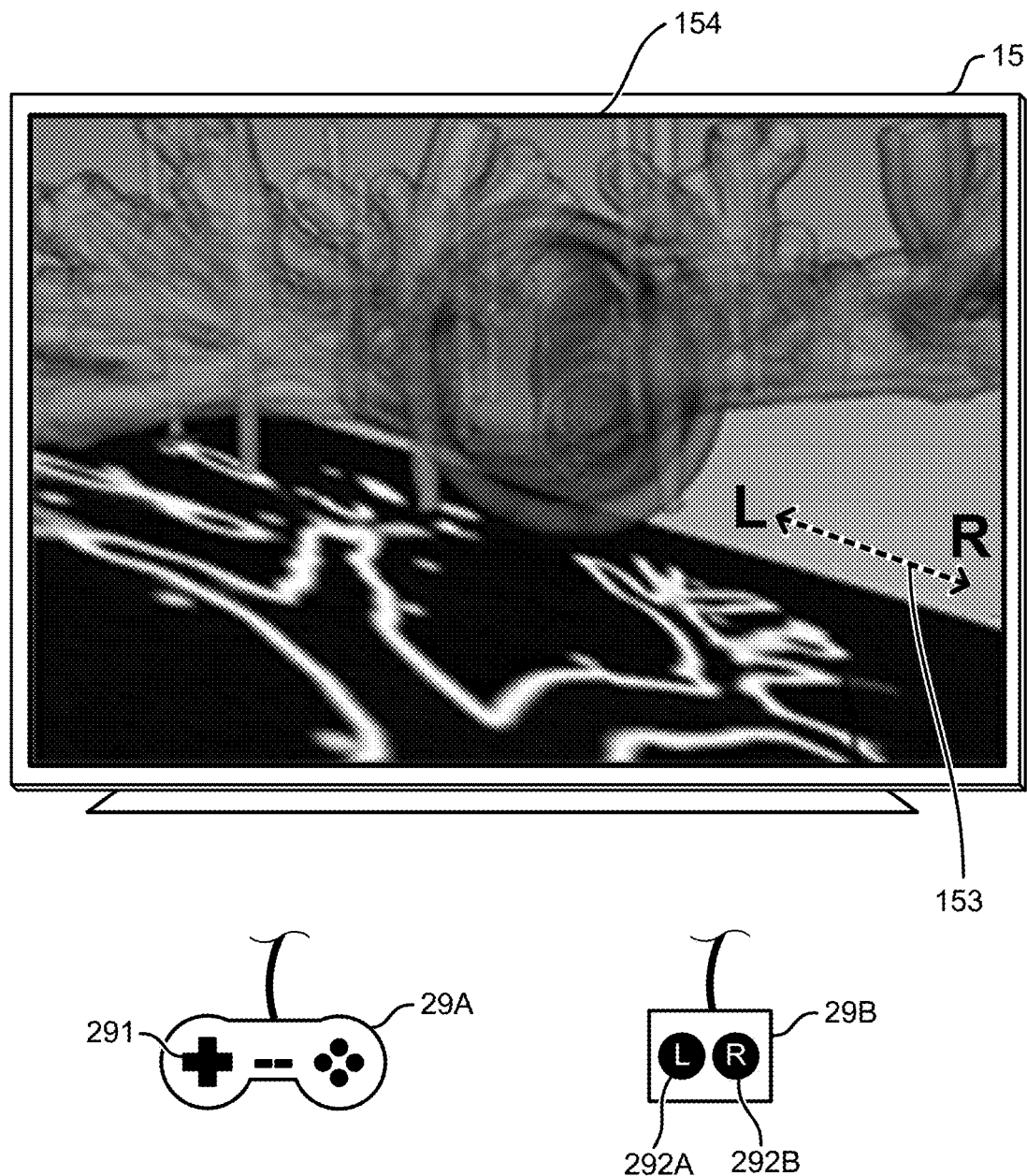
FIG. 17 illustrates an example embodiment of a display device that is displaying a fluoroscopic image and a first-person view of a three-dimensional (3D) model of a branching structure.

For example, FIG. 17 illustrates an example embodiment of a display device 15 that is displaying a fluoroscopic image and a first-person view of a 3D model of a branching structure. The fluoroscopic image and the first-person view of the 3D model are shown together in a combined image 154, and the displayed fluoroscopic image is a projection of the obtained fluoroscopic image onto a plane below the 3D model. The fluoroscopic image that is shown in the combined image 154 also indicates where both the location and the orientation of the viewpoint of the first-person view of the 3D model are in the fluoroscopic image. Additionally, the combined image 154 includes an inter-view-relationship indicator 153. Furthermore, the projection of the obtained fluoroscopic image onto the plane below the 3D model may be an inter-view-relationship indicator.

The flow then moves to block B1635, where the system controller 11 obtains an instructed direction from an input device 29. Then the flow moves to block B1640, where the system controller 11 controls the distal end 252 to move according to the instructed direction. Also, if the instructed direction was not obtained in the reference frame of the distal end 252 (which is also the reference frame of the first-person view of the 3D model), then the system controller 11 uses the reference-frame mapping to map the instructed direction to a movement direction in the reference frame of the distal end 252 and controls the distal end 252 to move according to the mapped movement direction.

For example, in FIG. 17, the medical system also includes two input devices 29. A first input device 29A is a control pad, and a second input device 29B has two buttons 292A-B. In some embodiments, a physician can use the first input device 29A to control the distal end 252 based on the reference frame of the first-person view of the 3D model. Also, a physician can use the second input device 29B to control the distal end 252 to move left or right in the reference frame of the fluoroscopic image by using the two buttons 292A-B. Thus, each input device 29 may control the movement of the distal end 252 in a respective reference frame. Also, if an instructed direction is obtained from the second input device 29B, then the system controller 11 maps the instructed direction to a movement direction in the reference frame of the distal end 252.

Next, in block B1645, the system controller 11 obtains distal-end positional information, which indicates the orientation and the location of the distal end 252.

Then the flow advances to block B1650, where the system controller 11 obtains an updated fluoroscopic image of the distal end 252 of the bendable medical device 24 from a C-arm scanner 31. Also, the system controller 11 obtains C-arm positional information.

The flow then proceeds to block B1655, where the system controller 11 generates a reference-frame mapping between the reference frame $\{S_d\}$ of the C-arm scanner 31 and the reference frame $\{S_e\}$ of the distal end 252 based on one or more intermediate reference frames (e.g., the reference frame $\{S_b\}$ of the proximal end 251, the reference frame $\{S_s\}$ of the position-tracking system), on the C-arm positional information, and on the distal-end positional information (e.g., as described in block B832 in FIG. 8).

Next, in block B1660, the system controller 11 generates an updated inter-view-relationship indicator, which indicates the relationship between an updated first-person view of the 3D model and the updated fluoroscopic image, based on the reference-frame mapping.

The flow then proceeds to block B1665, where the system controller 11 controls the display of the updated fluoroscopic image, the updated first-person view of the 3D model, and the updated inter-view-relationship indicator.

The flow then advances to block B1670, where the system controller 11 determines whether an instruction to move the C-arm 34 has been obtained. If an instruction to move the C-arm 34 has been obtained (B1670=Yes), then the flow moves to block B1675. In block B1675, the system controller 11 controls the C-arm 34 of the C-arm scanner 31 to move. And the flow then returns to block B1650.

If an instruction to move the C-arm 34 has not been obtained (B1670=No), then the flow moves to block B1680.

In block B1680, the system controller 11 determines whether another instructed direction has been obtained. If the system controller 11 determines that another instructed direction has been obtained (B1680=Yes), then the flow returns to block B1640. If the system controller 11 determines that another instructed direction has not been obtained (B1680=No), then the flow moves to block B1685.

In block B1685, the system controller 11 determines whether a stop instruction has been obtained. If a stop instruction has not been obtained (B1685=No), then the flow returns to block B1665, where the system controller 11 continues to control the display of the updated fluoroscopic image, the updated first-person view of the 3D model, and the updated inter-view-relationship indicator. If a stop instruction has been obtained (B1685=Yes), then the flow ends in block B1690.

Figure 18:
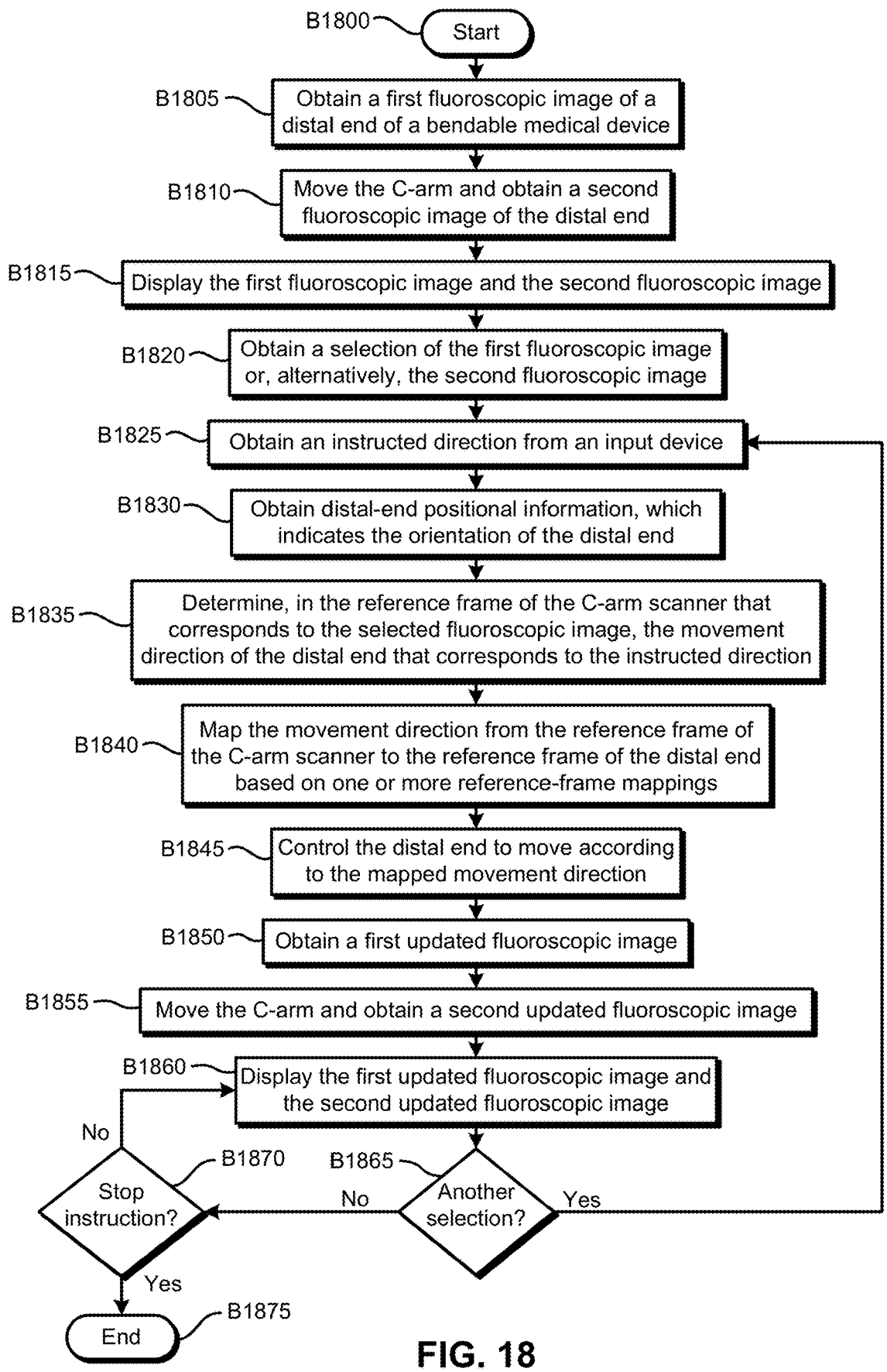
FIG. 18 illustrates an example embodiment of an operational flow for controlling a bendable medical device.

FIG. 18 illustrates an example embodiment of an operational flow for controlling a bendable medical device. The flow starts in block B1800 and then moves to block B1805, where the system controller 11 obtains a first fluoroscopic image of a distal end 252 of a bendable medical device 24. Also, along with the first fluoroscopic image, the system controller 11 obtains C-arm positional information. And, in some embodiments of block B1805, the system controller 11 also obtains an endoscopic image.

The flow then proceeds to block B1810, where the system controller 11 controls the C-arm scanner 31 to move the C-arm 34 to a new rotation angle and obtains a second fluoroscopic image of the distal end 252, which is acquired while the C-arm 34 is situated in the new rotation angle. Additionally, along with the second fluoroscopic image, the system controller 11 obtains C-arm positional information.

Figure 19:
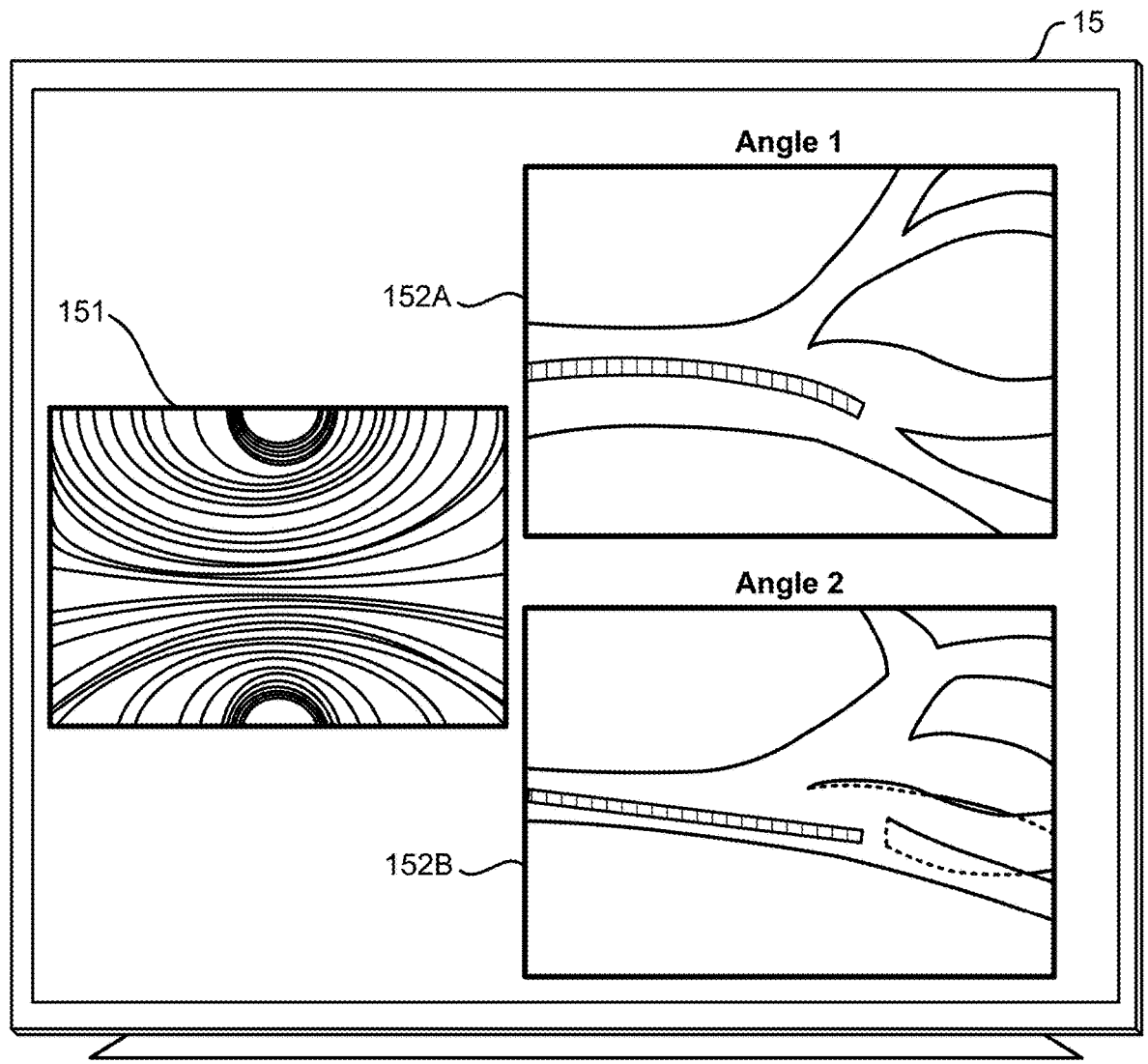
FIG. 19 illustrates an example embodiment of a display device that is displaying an endoscopic image, a first fluoroscopic image, and a second fluoroscopic image.

Following, in block B1815, the system controller 11 controls the display of the first fluoroscopic image and the second fluoroscopic image on a display device 15. Also, the system controller 11 may control the display of an endoscopic image. For example, FIG. 19 illustrates an example embodiment of a display device 15 that is displaying an endoscopic image 151, a first fluoroscopic image 152A, and a second fluoroscopic image 152B. In this example, after the first fluoroscopic image 152A was captured, the C-arm 34 was rotated by approximately 90 degrees before the second fluoroscopic image 152B was captured. Thus, the reference frame of the first fluoroscopic image 152A is rotated by 90 degrees relative to the reference frame of the second fluoroscopic image 152B.

The flow then advances to block B1820, where the system controller 11 obtains, from an input device 29, a selection of the first fluoroscopic image or, alternatively, the second fluoroscopic image. For example, the instruction may be obtained from a touchscreen, a mouse, a keyboard, or a button on a control pad.

Next, in block B1825, the system controller 11 obtains an instructed direction from an input device 29, which may be a different input device than the input device 29 that provides the selection in block B1820, or may be the same input device.

The flow then proceeds to block B1830, where the system controller 11 obtains distal-end positional information, which indicates the orientation (and, in some embodiments, the location) of the distal end 252.

The flow then advances to block B1835, where the system controller 11 determines, in the reference frame $\{S_d\}$ of the C-arm scanner 31 that corresponds to the selected fluoroscopic image (which is the fluoroscopic viewpoint of the selected fluoroscopic image), the movement direction of the distal end 252 that corresponds to the instructed direction.

Next, in block B1840, the system controller 11 maps the movement direction from the reference frame $\{S_d\}$ of the C-arm scanner 31 that corresponds to the selected fluoroscopic image to the reference frame $\{S_e\}$ of the distal end 252 based on one or more reference-frame mappings (e.g., as described in block B830 (including blocks B832 and B834) in FIG. 8).

Then, in block B1845, the system controller 11 controls the distal end 252 to move according to the mapped movement direction.

For example, if a selection of the second fluoroscopic image 152B in FIG. 19 is acquired, and then an instructed direction for "right" is acquired, the system controller 11 determines which movement direction, in the reference frame of the C-arm scanner when the second fluoroscopic image 152B (in the viewpoint of the second fluoroscopic image 152B) was acquired, corresponds to "right." Then the system controller 11 maps the movement direction from the reference frame of the C-arm scanner (when the second fluoroscopic image 152B was acquired) to the reference frame of the distal end 252 based on one or more reference-frame mappings, and the system controller 11 controls the distal end 252 to move according to the mapped movement direction.

Then the flow advances to block B1850, where the system controller 11 obtains a first updated fluoroscopic image of the distal end 252 of the bendable medical device 24 from the C-arm scanner 31. The first updated fluoroscopic image may be obtained while the C-arm 34 is in one of the following positions: a position that is the same as the position used to capture the previous first fluoroscopic image (or the previous first updated fluoroscopic image), a position that is the same as the position used to capture the previous second fluoroscopic image (or the previous second updated fluoroscopic image), and a position that is different from both the position used to capture the previous first fluoroscopic image (or the previous first updated fluoroscopic image) and the position used to capture the previous second fluoroscopic image (or the previous second updated fluoroscopic image). Accordingly, in block B1850, the system controller 11 may also control the C-arm 34 to move to a new position. Also, along with the first updated fluoroscopic image, the system controller 11 obtains corresponding C-arm positional information.

Then, in block B1855, the system controller 11 controls the C-arm 34 to move to a new position and controls the C-arm scanner 31 to obtain a second updated fluoroscopic image. The second updated fluoroscopic image may be obtained while the C-arm 34 is in one of the following positions: a position that is the same as the position used to capture the previous first fluoroscopic image (or the previous first updated fluoroscopic image), a position that is the same as the position used to capture the previous second fluoroscopic image (or the previous second updated fluoroscopic image), and a position that is different from both the position used to capture the previous first fluoroscopic image (or the previous first updated fluoroscopic image) and the position used to capture the previous second fluoroscopic image (or the previous second updated fluoroscopic image). And, along with the second updated fluoroscopic image, the system controller 11 obtains corresponding C-arm positional information.

Additionally, in block B1850 or B1855, the system controller 11 may obtain an updated endoscopic image.

The flow then proceeds to block B1860, where the system controller 11 controls the display of the first updated fluoroscopic image and the display of the second updated fluoroscopic image. Also, the system controller 11 may control the display of an updated endoscopic image.

The flow then proceeds to block B1865, where the system controller 11 determines whether a selection of the first updated fluoroscopic image or a selection of the second updated fluoroscopic image has been obtained. If a selection of the first updated fluoroscopic image or a selection of the second updated fluoroscopic image has been obtained has been obtained (B1865=Yes), then the flow returns to block B1825.

If neither a selection of the first updated fluoroscopic image nor a selection of the second updated fluoroscopic image has been obtained (B1865=No), then the flow moves to block B1870.

In block B1870, the system controller 11 determines whether a stop instruction has been obtained. If a stop instruction has not been obtained (B1870=No), then the flow returns to block B1860, where the system controller 11 continues to control the display of the first updated fluoroscopic image and the second updated fluoroscopic image. If a stop instruction has been obtained (B1870=Yes), then the flow ends in block B1875.

Figure 20:
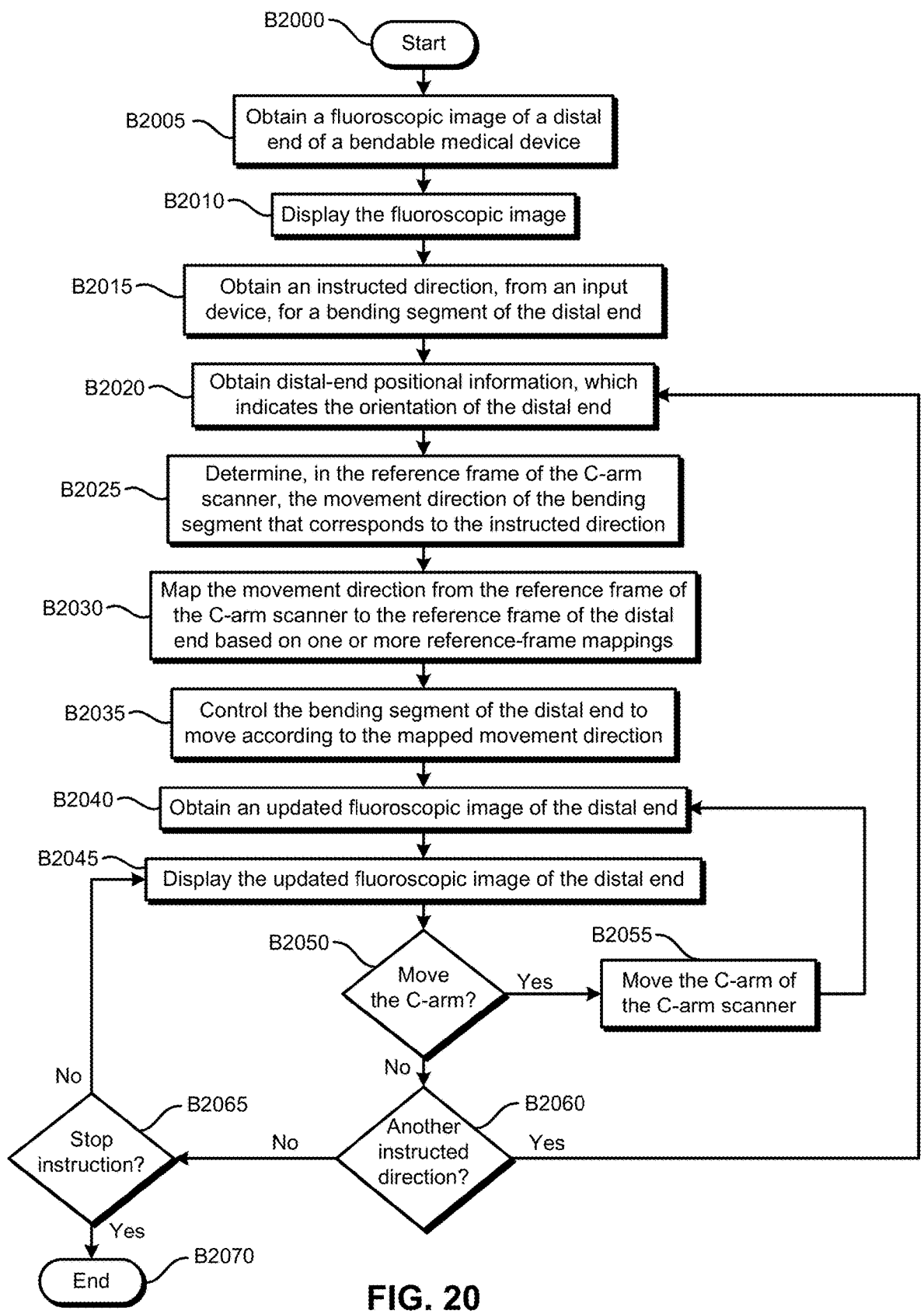
FIG. 20 illustrates an example embodiment of an operational flow for controlling a bendable medical device.

FIG. 20 illustrates an example embodiment of an operational flow for controlling a bendable medical device. The flow starts in block B2000 and then moves to block B2005, where the system controller 11 obtains a fluoroscopic image of a distal end 252 of a bendable medical device 24 from a C-arm scanner 31. And, along with the fluoroscopic image, the system controller 11 obtains C-arm positional information. Then, in block B2010, the system controller 11 controls the display of the fluoroscopic image of the distal end 252 of the bendable medical device 24. Also, in blocks B2005 and B2010, the system controller 11 may obtain and control the display of an endoscopic image.

Next, in block B2015, the system controller 11 obtains an instructed direction, from an input device 29, for a bending segment of the distal end 252. In some embodiments (e.g., the embodiments in FIGS. 24, 25A, 25B, 26A, and 26B), the distal end 252 includes two or more bending segments.

Figure 21:
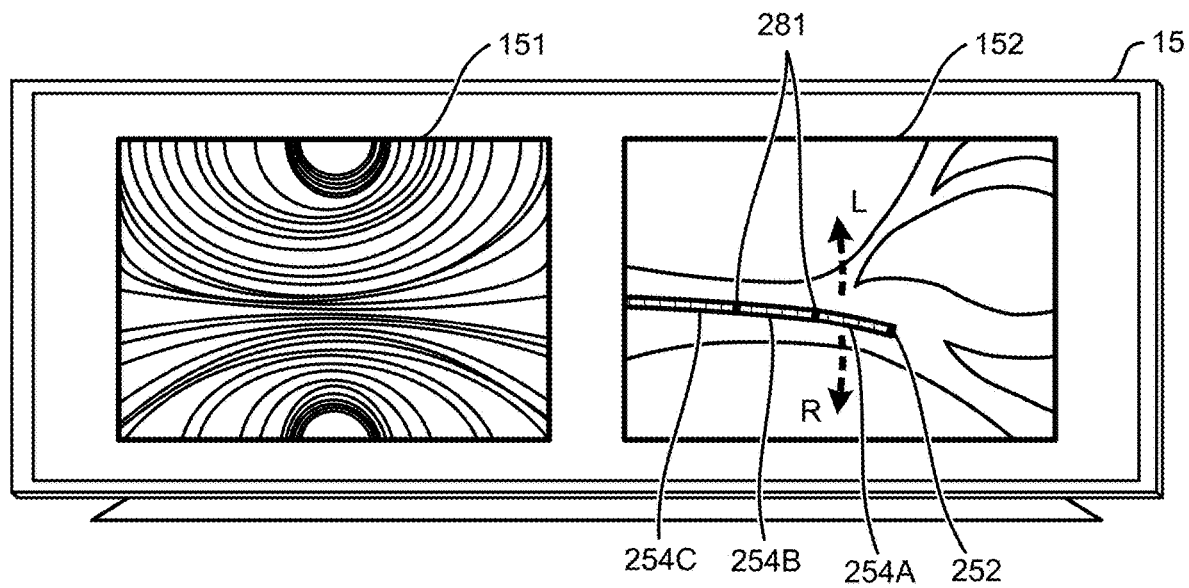
FIG. 21 illustrates an example embodiment of a display device that is displaying a fluoroscopic image and an endoscopic image.
Figure 21:
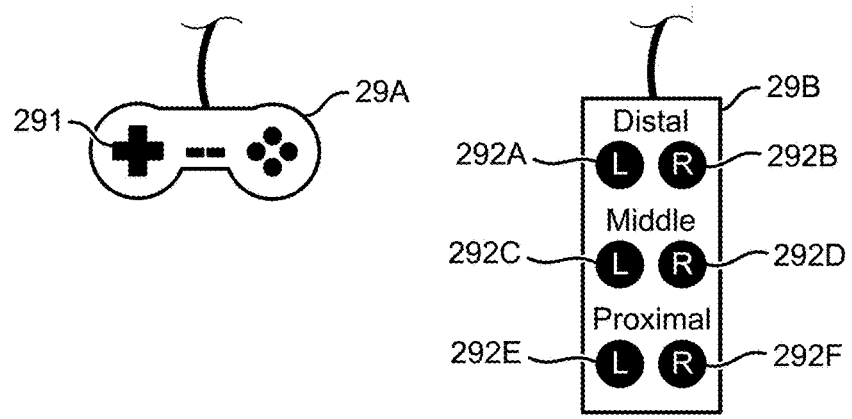
Figure 26A:
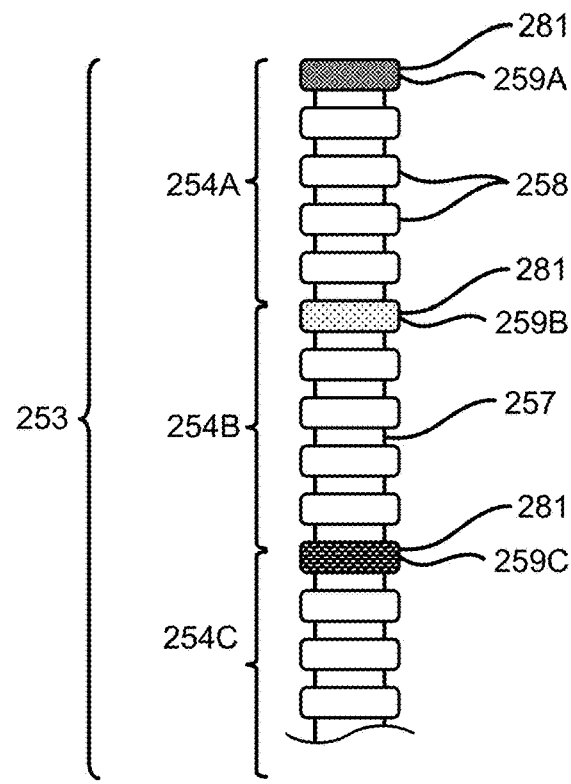
FIG. 26A illustrates an example embodiment of a steerable section of a bendable medical device.
Figure 26B:
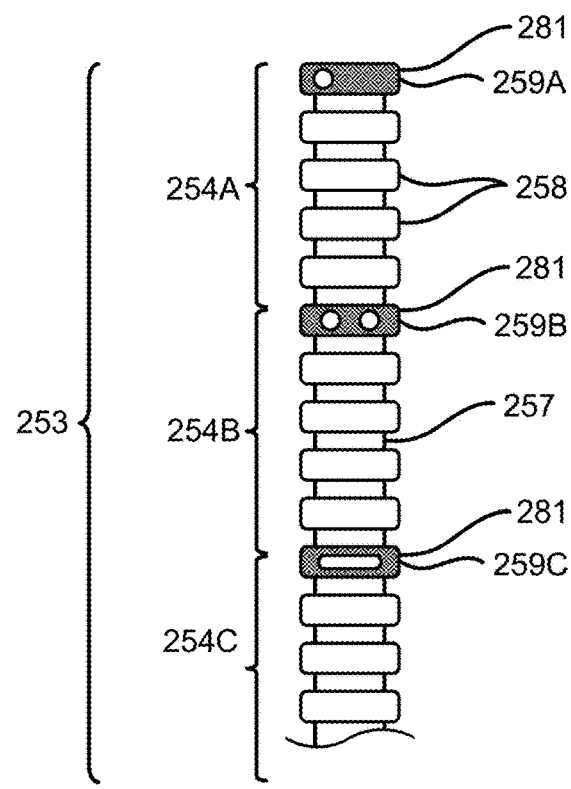
FIG. 26B illustrates an example embodiment of a steerable section of a bendable medical device.

Also, the bending segments may be delineated by radiopaque markers, such as radiopaque wire-guiding members or anchor rings that are made of different materials or that have different markings (e.g., holes). Example embodiments of radiopaque markers are shown in FIGS. 26A-B. The radiopaque markers make the boundaries of the bending segments more visible in fluoroscopic images. For example, FIG. 21 illustrates an example embodiment of a display device that is displaying a fluoroscopic image 152 and an endoscopic image 151. The distal end 252 is visible in the fluoroscopic image 152. Also, the distal end 252 includes three bending segments 254: a tip segment 254A, a middle segment 254B, and a proximal segment 254C. Radiopaque markers 281 are visible in the fluoroscopic image 152, and the radiopaque markers 281 are located at the boundary between the tip segment 254A and the middle segment 254B and at the boundary between the middle segment 254B and the proximal segment 254C. Furthermore, the distal tip of the tip segment 254A may also include a radiopaque marker. And although the display device 15 may not display any direction indicators (e.g., a left indicator, a right indicator) in the fluoroscopic image 152, FIG. 21 includes a left indicator L and a right indicator R.

Additionally, in FIG. 21, the medical system includes two input devices 29. A first input device 29A is a control pad, and a second input device 29B has six buttons 292A-F. In some embodiments, a physician can use the first input device 29A to control the distal end 252 based on the reference frame $\{S_e\}$ of the distal end 252 (the endoscopic viewpoint). Also, a physician can use the second input device 29B to control the bending segments 254 of the distal end 252 to move left or right in the reference frame $\{S_d\}$ of the fluoroscopic image (the fluoroscopic viewpoint) by using the six buttons 292A-F. When activated, button 292A generates an instructed direction to move the tip segment 254A to the left, button 292B generates an instructed direction to move the tip segment 254A to the right, button 292C generates an instructed direction to move the middle segment 254B to the left, button 292D generates an instructed direction to move the middle segment 254B to the right, button 292E generates an instructed direction to move the proximal segment 254C to the left, and button 292F generates an instructed direction to move the proximal segment 254C to the right. Thus, each input device 29 may control the movement of the distal end 252 in a respective reference frame (i.e., in a respective viewpoint). Also, if an instructed direction is obtained from the second input device 29B, then, as explained below, the system controller 11 maps the instructed direction to the reference frame $\{S_e\}$ of the distal end 252 (i.e., maps the instructed direction to a movement direction in the reference frame $\{S_e\}$ of the distal end 252).

The flow then proceeds to block B2020, where the system controller 11 obtains distal-end positional information, which indicates the orientation (and, in some embodiments, the location) of the distal end 252. The flow then advances to block B2025, where the system controller 11 determines, in the reference frame $\{S_d\}$ of the C-arm scanner 31, the movement direction of the bending segment that corresponds to the instructed direction. Next, in block B2030, the system controller 11 maps the movement direction from the reference frame $\{S_d\}$ of the C-arm scanner 31 to the reference frame $\{S_e\}$ of the distal end 252 based on one or more reference-frame mappings (e.g., as described in block B830 (including blocks B832 and B834) in FIG. 8). Then, in block B2035, the system controller 11 controls the corresponding bending segment of the distal end 252 to move according to the mapped movement direction.

Then the flow advances to block B2040, where the system controller 11 obtains an updated fluoroscopic image of the distal end 252 and C-arm positional information from the C-arm scanner 31. In block B2045, the system controller 11 controls the display of the updated fluoroscopic image of the distal end 252 of the bendable medical device 24. Also, in blocks B2040 and B2045, the system controller 11 may obtain and control the display of an updated endoscopic image.

The flow then proceeds to block B2050, where the system controller 11 determines whether an instruction to move the C-arm 34 has been obtained. If an instruction to move the C-arm 34 has been obtained (B2050=Yes), then the flow moves to block B2055. In block B2055, the system controller 11 controls the C-arm 34 of the C-arm scanner 31 to move. And the flow then returns to block B2040.

If an instruction to move the C-arm 34 has not been obtained (B2050=No), then the flow moves to block B2060.

In block B2060, the system controller 11 determines whether another instructed direction for a bending segment of the distal end 252 has been obtained. If the system controller 11 has obtained another instructed direction for a bending segment of the distal end 252 (B2060=Yes), then the flow returns to block B2020. If the system controller 11 has not obtained another instructed direction (B2060=No), then the flow moves to block B2065.

In block B2065, the system controller 11 determines whether a stop instruction has been obtained. If a stop instruction has not been obtained (B2065=No), then the flow returns to block B2045, where the system controller 11 continues to control the display of the updated fluoroscopic image of the distal end 252. If a stop instruction has been obtained (B2065=Yes), then the flow ends in block B2070.

Figure 22:
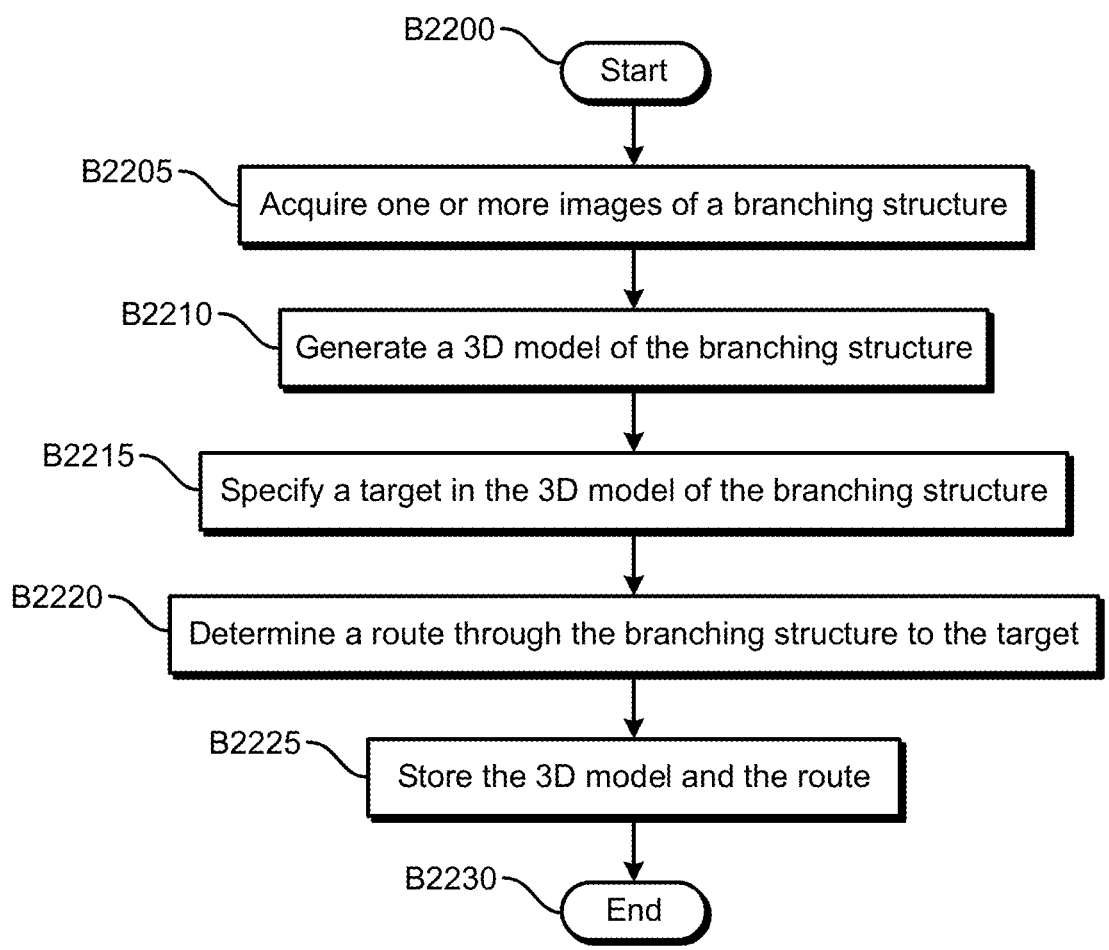
FIG. 22 illustrates an example embodiment of an operational flow for planning the navigation of a bendable medical device.
Figure 23:
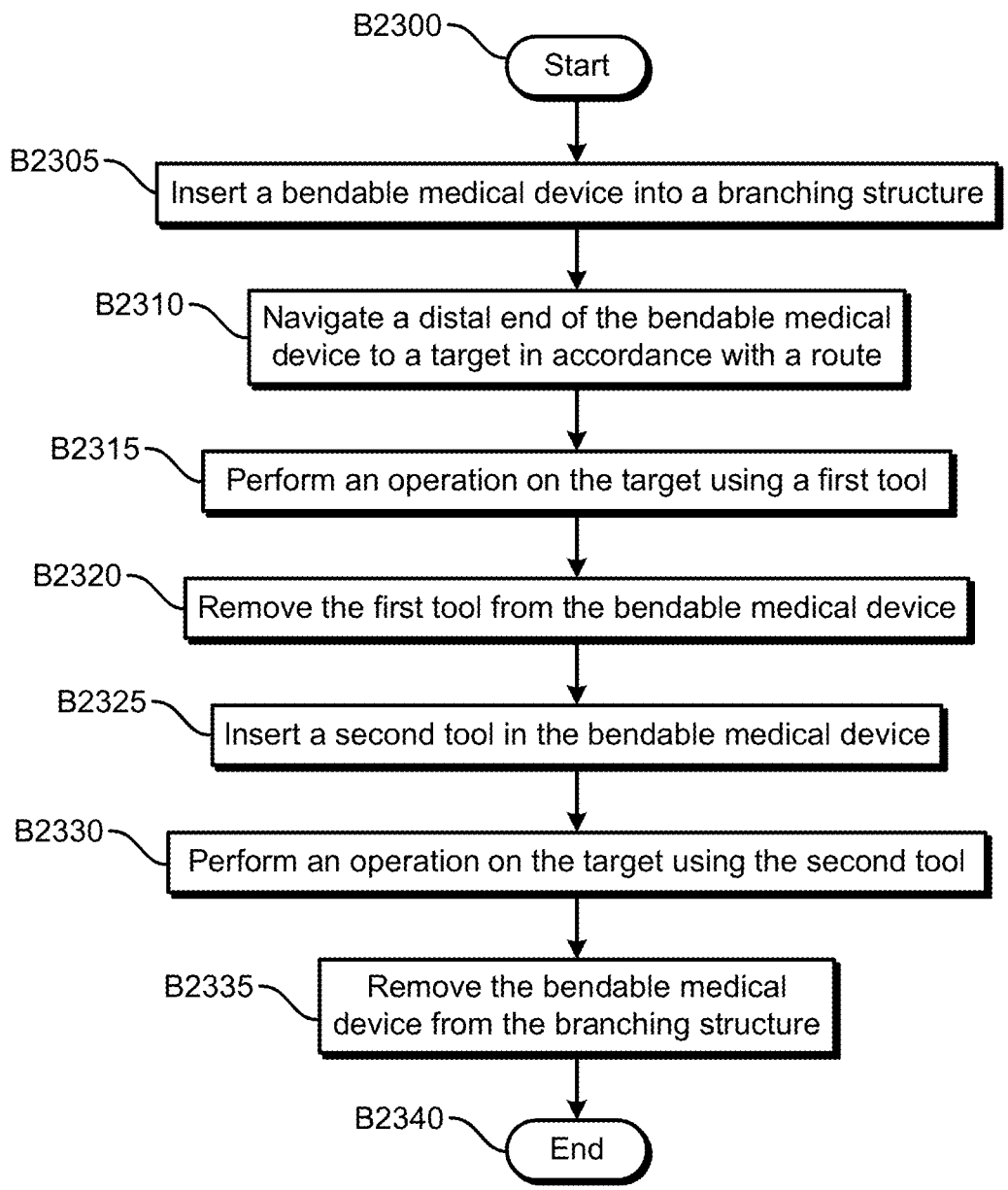
FIG. 23 illustrates an example embodiment of an operational flow for performing an operation on a target using a bendable medical device.

FIG. 22 illustrates an example embodiment of an operational flow for planning the navigation of a bendable medical device 24. The flow begins in block B2200 and then moves to B2205, where a system controller 11 obtains one or more images (e.g., X-ray images, computed-tomography (CT) images, magnetic-resonance images (MRI images)) of a branching structure (e.g., a branching structure, such as an airway or blood vessel).

Then, in block B2210, the system controller 11 generates a 3D model of the branching structure based on the one or more images. Next, in block B2215, the system controller 11 specifies a target in the 3D model of the branching structure. The target may be specified based on user input.

The flow then moves to block B2220, where the system controller 11 determines a route through the branching structure to the target based on the 3D model and on the specified target. Also, the system controller 11 may determine the route based on user input. The flow then proceeds to block B2225, where the system controller 11 stores or outputs the 3D model and the route. Finally, the flow ends in block B2230.

FIG. 23 illustrates an example embodiment of an operational flow for performing an operation on a target using a bendable medical device. The flow begins in block B2300 and then moves to block B2305, where a system controller 11 controls the insertion of a bendable medical device 24 into a branching structure. Next, in block B2310, the system controller 11 controls the navigation of a distal end 252 of the bendable medical device 24 to a target according to a previously generated route (e.g., a route generated according to FIG. 22).

Figure 25A:
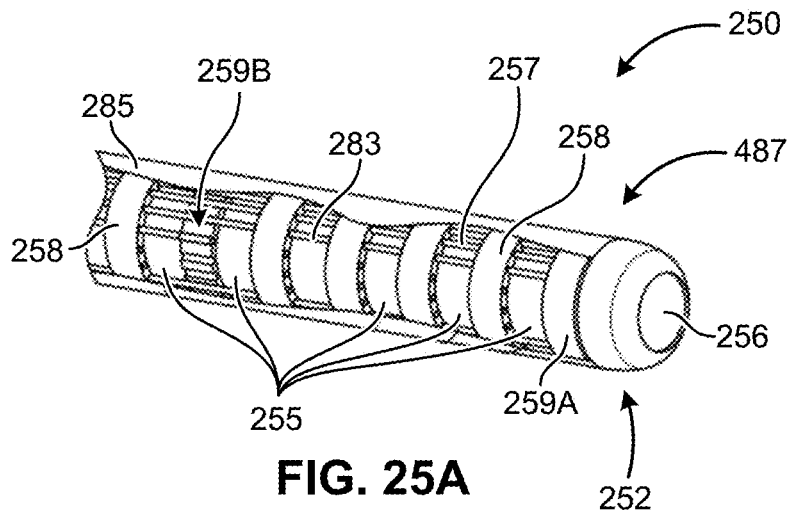
FIGS. 25A-B illustrate additional details of an example embodiment of a tubular flexible body.
Figure 25B:
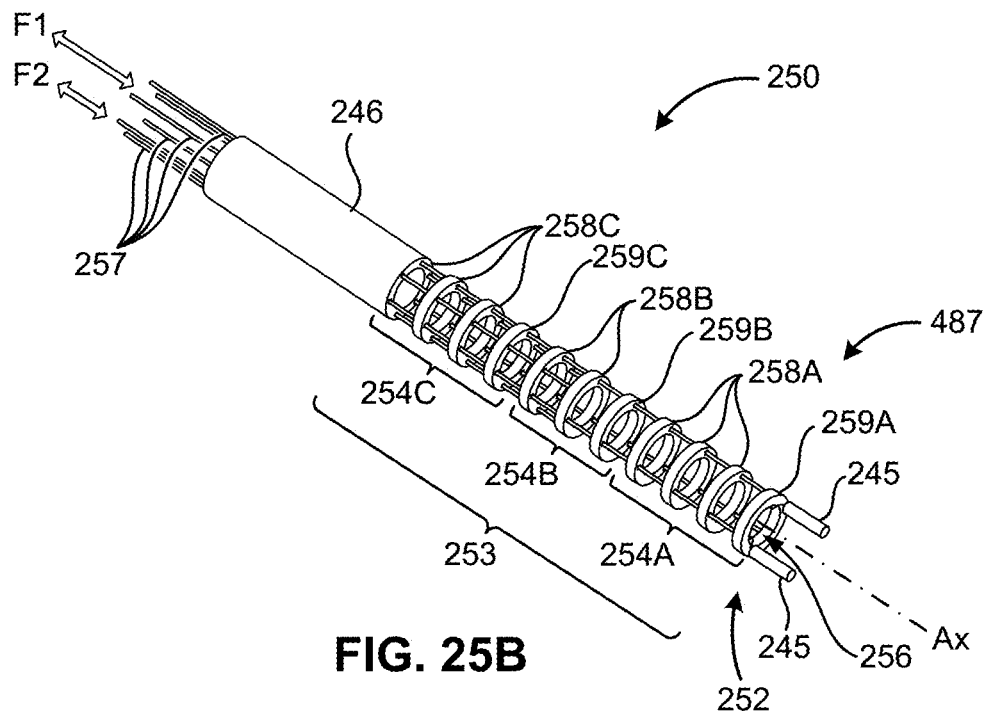

The flow then moves to block B2315, where the system controller 11 controls a first tool to perform an operation on the target. The first tool is located at the distal end 252 and is inserted into a central lumen or tool channel 256 of the tubular flexible body 250 of the bendable medical device 24. Examples of the central lumen or tool channel 256 are illustrated in FIGS. 25A-B.

The flow then proceeds to block B2320, where the first tool is removed from the bendable medical device 24. And, in block B2325, a second tool is inserted into the central lumen or tool channel 256 of the bendable medical device.

Next, in block B2330, the system controller 11 controls the second tool to perform an operation on the target.

Following, in block B2335, the system controller 11 controls the removal of the bendable medical device 24 from the branching structure. Finally, the flow ends in block B2340.

Figure 24:
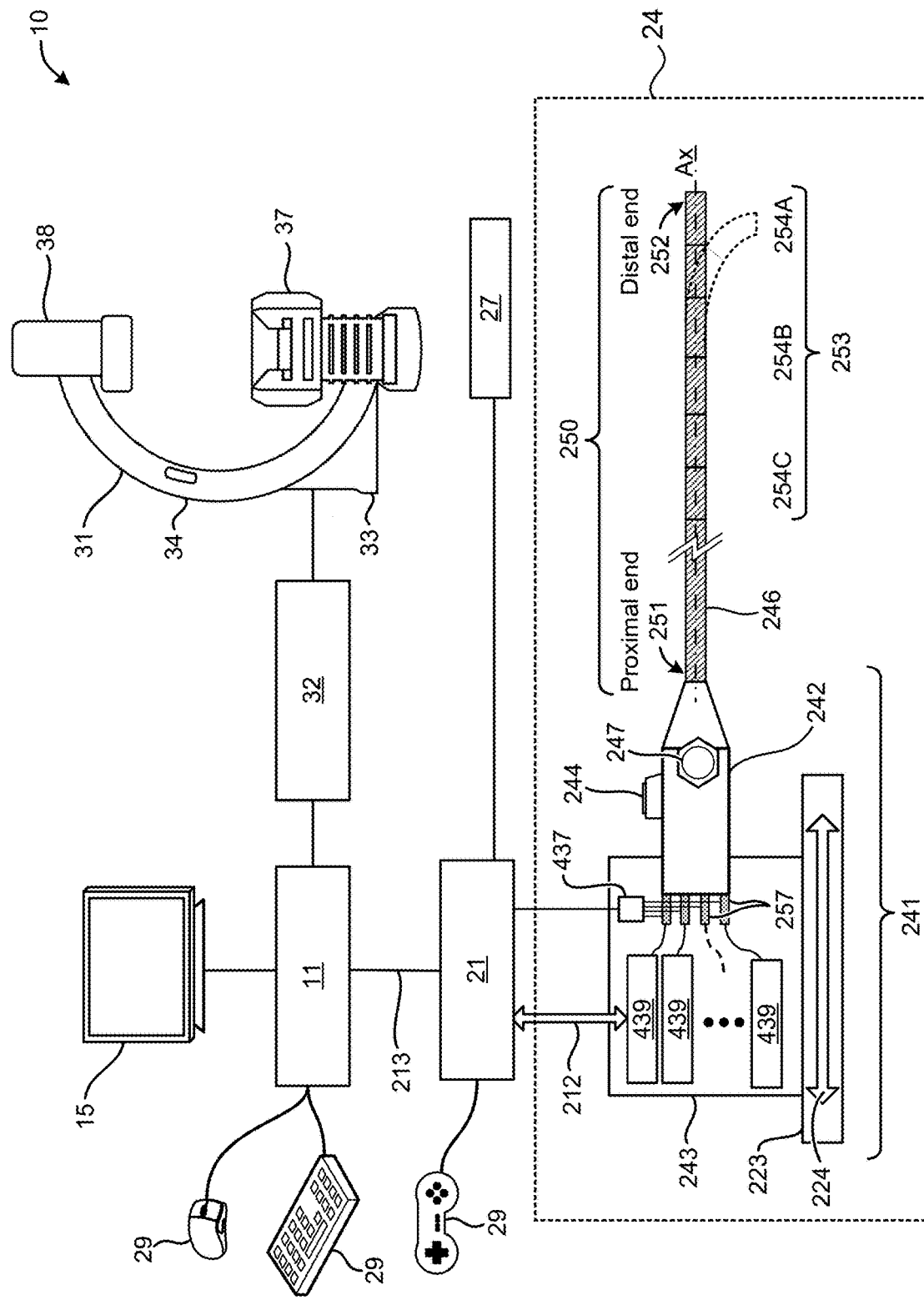
FIG. 24 illustrates an example embodiment of a medical system.

FIG. 24 illustrates an example embodiment of a medical system 10 (e.g., a robotic medical system). The medical system 10 includes a system controller 11, a bendable-device controller 21, a bendable medical device 24, a position-tracking device 27, a C-arm scanner 31, a C-arm controller 32, and a display device 15.

The bendable medical device 24 of the medical system 10 can include a continuum or multi-segment robot that is configured to form a continuously curved geometry by actuating one or more bending segments 254 of a steerable section 253 of the bendable medical device 24. The medical system 10 makes use of the bendable medical device 24 to treat a patient under interactive commands of a user (e.g., a physician). The bendable medical device 24 includes a connector assembly 242, an actuation unit 243, and a tubular flexible body 250 (e.g., a catheter sheath). The tubular flexible body 250 includes a multi-segment distal steerable section 253 and a single-segment proximal-end section 246. The proximal-end section 246 is connected to the actuation unit 243 via the connector assembly 242. The actuation unit 243 may be configured to be detachably mounted to a support platform 223.

The bendable medical device 24 in this embodiment is a steerable instrument. Thus, while the following description refers to a steerable instrument 24, other embodiments include a different bendable medical device.

The steerable instrument 24 can be configured for a number of medical applications or industrial applications. Under medical applications, the steerable instrument 24 can be configured as a robotic endoscope, as a steerable catheter, or as a surgical introducer sheath or sleeve that uses principles of kinematic (robotic) navigation for guiding a medical tool through tortuous bodily lumens, for example.

The tubular flexible body 250 has a non-steerable proximal-end section 246 and a distal steerable section 253 that is composed of multiple bending segments 254, which are arranged lengthwise along a longitudinal axis (Ax). At least one central lumen or tool channel extends 256 along the length of the tubular flexible body 250 and through part of the connector assembly 242. In some embodiments, the steerable instrument 24 is controlled by the bendable-device controller 21 via the actuation unit 243. Also, the actuation unit 243 may be a handheld controller (handle) connected to the proximal-end section 246 of the tubular flexible body 250 by the connector assembly 242, and the actuation unit 243 may be connected to another input device (e.g., a joystick, a control pad, a keyboard, a mouse). The actuation unit 243 can include any applicable force-generating device and a mechanical element that can, respectively, generate and transmit sufficient actuating force for bending at least one bending segment 254 of the steerable section 253. In that regard, the actuation unit 243 may include any device capable of generating and transmitting an actuating force including, for example, a mechanical force, a hydraulic force, a magnetic force, or a pneumatic force. The support platform 223 may include, for example, a robotic arm and a linear stage 224, which serves to guide the steerable instrument 24 (the actuation unit 243, the connector assembly 242, and the tubular flexible body 250) in a moving direction (typically linear movement) for insertion or retraction of the tubular flexible body 250 relative to a patient (e.g., a branching structure of a patient).

The bendable-device controller 21 generally includes electronic components, such as processors, memories, a proportional integral derivative (PID) controller, and a digital signal processor (DSP) device, along with suitable software, firmware and peripheral hardware. The bendable-device controller 21 can be part of, or be connected to the system controller 11 (e.g., a computer or system console). The bendable-device controller 21 includes the necessary software (computer-executable code, programs, and applications) executable by one or more processors, according to a user's interactions with the bendable-device controller 21 via a one or more input devices 29, to control the steerable instrument 24. The operations of the one or more processors may be implemented by loading and executing a program or may be implemented by a dedicated circuit (e.g., FPGA, ASIC).

The system controller 11, the bendable-device controller 21, and the actuation unit 243 are operably connected to each other by a network connection or a cable bundle 213 and a data bus 212. Among other functions, the system controller 11 can provide a physician or other user with a GUI and other information that are displayed on the display device 15, so that the user can interact with and remotely operate the steerable instrument 24. For example, the system controller 11 can display information that indicates the position (the orientation and the location) of the distal end 252 of the tubular flexible body 250 on the display device 15, and the information may be presented in the form of images, graphics, or text.

The bendable-device controller 21 is configured to control the actuation unit 243, which includes a plurality of actuating motors 439 (or actuators). The number of actuating motors 439 (or actuators) will depend on the design of the actuation unit 243, and it can include a single (one) actuating motor 439 (or actuator) that can actuate all driving wires 257 independently, or it could include a number of actuating motors 439 (or actuators), for example a number equal to the number of driving wires 257 so that each actuating motor 439 (or actuator) can individually actuate a respective driving wire 257.

The bendable-device controller 21 may also include or be connected to one or more actuation-control sensors 437. The actuation-control sensors 437 can include one or more strain sensors or one or more position sensors that are configured to detect or measure compressive or tensile forces (actuating forces) exerted on the driving wires 257 to bend one or more of the bending segments 254. The actuation-control sensors 437 may output a signal corresponding to an amount of compressive or tensile force (an amount of strain) being applied to a driving wire 257 at any given point in time. The signals from the actuation-control sensors 437 (e.g., strain sensor, position sensor) for each driving wire 257 are supplied to the bendable-device controller 21 and allow the bendable-device controller 21 to control each actuating motor 439 (or driving wire 257) individually. In this manner, each driving wire 257 can be actively controlled, by a feedback loop, to implement appropriate guidance for navigating the steerable section 253 through intraluminal, tortuous paths of a branching structure.

FIGS. 25A-B illustrate additional details of an example embodiment of the tubular flexible body 250. FIG. 25A is a three-dimensional partially cutaway view and FIG. 25B is a perspective view of the tubular flexible body 250, which is composed of a non-steerable proximal-end section 246 and a distal steerable section 253.

The non-steerable proximal-end section 246 is a single-piece elongated tubular component. Here, the non-steerable tubular-shaped proximal-end section 246 and a central lumen extrusion 255 (which is described further below) can be made of similar biocompatible polymer materials, such as polyether block amide copolymer (e.g., Pebax® brand produced by Arkema), which is a well-known polymer used in the fabrication of catheter shafts. Other medical-grade thermoplastic polyurethane (TPU) and thermoplastic elastomer (TPE) materials can also be used as tubing-extrusion materials for medical catheter and endoscope devices that demand precision and consistency. Furthermore, other commonly known catheter-tubing materials may be used, including PVC, HDPE, Polyurethane, Nylon, FEP, PFA, ETFE, PTFE (liners), PEEK, TPE, Grilamid® lubricious films, and many others.

As shown in FIG. 25A, the tubular structure also includes an outer jacket 285 and a central lumen extrusion 255. The central lumen extrusion 255 includes an inner liner reinforced by a reinforcing structure. The inner liner has an inner surface which defines a central lumen or tool channel 256 and has an outer surface onto which a plurality of wire-guiding members 258 are arranged. To improve the navigation process, it can be advantageous to reinforce the inner liner of the central lumen or tool channel 256.

The steerable section 253 incudes a plurality of bending segments 254, including a proximal bending segment 254C, a middle bending segment 254B, and a distal bending segment 254A. As shown in FIG. 25B, each bending segment 254 is formed of two or more wire-guiding members 258 (e.g., wire-guiding rings) cooperatively arranged in a lengthwise direction to form a tubular structure. The distal bending segment 254A includes a plurality of wire-guiding members 258A; the middle bending segment 254B includes a plurality of wire-guiding members 258B; and the proximal bending segment 254C includes a plurality of wire-guiding members 258C. The distal bending segment 254A is joined to the middle bending segment 254B by an anchor ring 259B, and the middle bending segment 254B is connected to the proximal bending segment 254C by an anchor ring 259C. Each wire-guiding member 258 has a plurality of wire conduits 484 (e.g., thru-holes 484) in the wall of the wire-guiding member 258. The wire conduits 484 serve as conduits through which wires (driving wires 257, support wires 283) are guided along the wall of the tubular shaft. Also, the wire conduits 484 may be formed on the outer surface or the inner surface of each wire-guiding member 258. Moreover, at least some wire-guiding members 258 can be formed without wire conduits 484. And the number of wire conduits 484 in each wire-guiding member 258 may depend on the bending segment 254 in which the wire-guiding member 258 is arranged.

The wire-guiding members 258 include a plurality of wire conduits 484 (secondary lumens) through which driving wires 257 or support wires 283 are passed. The driving wires 257 are moved by an actuating force to bend one or more of the bending segments 254 of the steerable section 253; the support wires 283 are not actuated.

FIG. 25B illustrates an example of the tubular flexible body 250 without the central lumen extrusion 255 and without the outer jacket 285. As shown in FIG. 25B, the plurality of driving wires 257 pass through the proximal-end section 246, advance through wire conduits 484 of wire-guiding members 258 of the proximal bending segment 254C, pass through wire conduits 484 of wire-guiding members 258 of the middle bending segment 254B, and pass through wire conduits 484 of wire-guiding members 258 of the distal bending segment 254A. Each bending segment 254 of the steerable section 253 is actuated by a set of antagonistic driving wires 257, which operate by a pulling or pushing force (an actuating force) to bend each bending segment 254 independently of each other. Forces F1 and F2 of different magnitude can be applied in the lengthwise direction to cause separate driving wires 257 to bend the various bending segments 254 in desired directions. A combination of forces F1 and F2 can also be applied to bend a given bending segment 254 in additional directions. To that end, a first set of driving wires 257 may be anchored at an anchor ring 259A at the distal end of the distal bending segment 254A, a second set of driving wires 257 may be anchored at an anchor ring 259B of the middle bending segment 254B, and at a third set of driving wires 257 may be anchored at an anchor ring 259C of the proximal bending segment 254C.

In some embodiments, three respective driving wires 257 may be used to actuate each bending segment 254. In such embodiments, the distal ends 487 of the three driving wires 257 in the first set of driving wires can be anchored to the anchor ring 259A at the distal end of the distal bending segment 254A, the distal ends 487 of the three driving wires 257 in the second set of driving wires can be anchored to the anchor ring 259B of the middle bending segment 254B, and the distal ends 487 of the three driving wires 257 in the third set of driving wires can be anchored to the anchor ring 259C of the proximal bending segment 254C. In such embodiments, nine driving wires 257 will pass through the proximal-end section 246 of the tubular flexible body 250. At each anchor ring 259, it may be advantageous to arrange (to anchor) the driving wires 257 equidistantly around the circumference of the anchor ring 259 at strategic locations so as to actuate each bending segment 254 independently in a desired direction. For example, the driving wires 257 can be anchored at equal intervals on the anchor ring 259 such that the driving wires 257 are anchored at 120-degree intervals and, when each bending segment 254 is actuated by three driving wires 257, the driving wires 257 would be able to actuate each bending segment 254 in substantially any direction (any angle with respect to lumen axis Ax).

Additionally, the proximal-end section 246 includes a plurality of wire conduits extending through the wall (or on the outer surface of the wall) of the proximal-end section 246. Also, the wire conduits are not limited to conduits within the wall itself. In some embodiments, the wire conduits of the proximal-end section 246 are formed on the outer surface or the inner surface of the proximal-end section 246.

Figure 25C:
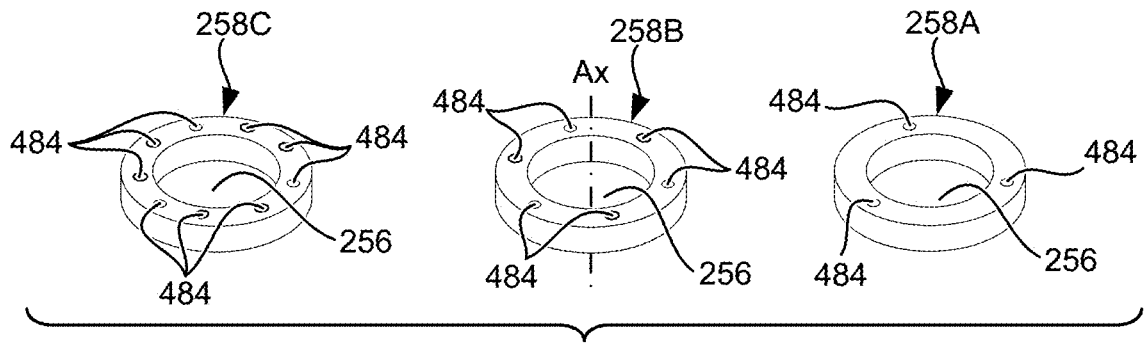
FIG. 25C illustrates one wire-guiding member from a distal bending segment, one wire-guiding member from a middle bending segment, and one wire-guiding member from a proximal bending segment.

FIG. 25C shows example embodiments of annular-shaped wire-guiding members 258 (wire-guiding rings) having a central opening or tool channel 256 and having secondary lumens or wire conduits 484 formed in the wall that surrounds the tool channel 256. The outer surface and the inner surface of each wire-guiding member 258 are shown as circular for ease of illustration, but some embodiments are not limited thereto. For example, the outer surface and the inner surface of each wire-guiding member 258 may have a substantially symmetric and closed polygonal shape, such as a hexagon, an octagon, etc.

FIG. 25C shows one wire-guiding member 258A from the distal bending segment 254A, one wire-guiding member 258B from the middle bending segment 254B, and one wire-guiding member 258C from the proximal bending segment 254C. The wire-guiding member 258A from the distal bending segment 254A includes three wire-guiding conduits 484; the wire-guiding member 258B from the middle bending segment 254B includes six wire-guiding conduits 484; and the wire-guiding member 258C from the proximal bending segment 254C includes nine wire-guiding conduits 484. In this embodiment, nine driving wires 257 can be arranged through the tubular wall in the proximal-end section 246. Then, the driving wires 257 continue through the wire conduits 484 of the wire-guiding member 258C from the proximal bending segment 254C, and are anchored to an anchor ring 259 for each bending segment 254. The anchor rings 259 are of substantially similar structure as the corresponding wire-guiding members 258. All wire-guiding members 258 and anchor rings 259 include a central opening or tool channel 256, and have a predetermined number of wire conduits 484 (thru-holes, secondary lumens) arranged around the tool channel 256 and substantially parallel to and equidistant from, the instrument axis Ax.

Furthermore, not all wire conduits 484 must be used for driving wires 257. At least some of the wire conduits 484 may be used to pass an electrical cable (e.g., wiring for sensors 170), some wire conduits 484 may be empty, and some wire conduits 484 may have support wires that are not driving wires 257. That is according to some embodiments, the wire conduits 484 of each wire-guiding member 258 can have several uses. For example, some wire conduits 484 may contain a control wire (driving wire 257), some may contain a support wire 283 that transmits no force, some are left empty, some may pass an optical fiber, some may have an electrical cable, and some may have an electronic component, such as a load cell or sensor. The wire-guiding members 258 and anchor rings 259 for the steerable section 253 can be made of biocompatible thermoplastic polymer similar to that used for the central lumen extrusion 255 or the proximal-end section 246.

Referring back to FIG. 24, the handle or connector assembly 242 provides an electromechanical interface between the proximal-end section 246 and the actuating motors 439 (or other actuators) in the actuation unit 243. For example, the connector assembly 242 may provide mechanical, electrical, or optical connections and may provide other data or digital connections for interfacing the bendable medical device 24 with the bendable-device controller 21 and the system controller 11. The handle or connector assembly 242 may also provide an access port 244, which can be used by a surgeon or other operator to insert instruments, imaging devices, or other end effectors through the central lumen or tool channel 256. For example, the access port 244 can be used to insert small instruments, such as small forceps, needles, or electrocautery instruments and the like. In addition, the connector assembly 242 may include one or more dials or control wheels 247 for manual control (bending or steering) of at least one segment of the steerable section 253. In some embodiments, the steerable section 253 may include more than one central lumen or tool channel 256, where at least one of those channels can be used for passing liquid or gaseous fluids, and another channel can be used for passing tools or imaging devices.

In operation, the system controller 11 and the bendable-device controller 21 are communicatively-coupled via the cable bundle 213 to transmit data to and obtain data from each other. The system controller 11 is also connected to and communicates with, the C-arm controller 32 and other external equipment, such as an image server (not shown in FIG. 24), etc., which are external of the medical system 10. The image server may include, but is not limited to a DICOM™ server connected to a PACS (Picture Archiving and Communication System) or medical imaging system, which may include, but is not limited to one or more of a CT scanner, a magnetic resonance imaging (MRI) scanner, or a fluoroscope, etc. The system controller 11 processes data provided by the bendable-device controller 21, data provided the C-arm scanner 31, or data provided by an image server. The system controller 11 controls the display of images and other medical information on an display device 15 to aid a user in performing a medical procedure.

For a medical procedure where the steerable instrument 24 will be used, medical images (e.g., from the CT scanner) may be pre-operatively provided to the system controller 11. With the system controller 11, a user creates an anatomical computer model (e.g., a 3D model) of a branching structure from the images. In some embodiments, the branching structure is the lung airways of a patient. From chest images obtained from the C-arm scanner 31, another imaging device, or a PACS system, the user can segment the lung airways for clinical treatments, such as a biopsy. After the system controller 11 generates a map or 3D model of the lung airways, the user can also use the navigation software system to create a plan to access a target (e.g., a lesion for the biopsy). The plan includes the target and a route (navigation path) through the airways to insert the steerable section 253 of the steerable instrument 24 and guide the steerable section 253 to the target.

The bendable-device controller 21 includes firmware, control circuitry, and peripheral hardware to control the steerable instrument 24, the support platform 223, and the position-tracking device 27 (e.g., an electromagnetic (EM) field generator). The bendable-device controller 21 is communicatively coupled with the actuation unit 243, the support platform 223, the position-tracking device 27, and one or more input devices 29. In this manner, the bendable-device controller 21, in coordination with the system controller 11, controls the overall functions of the steerable instrument 24 and the support platform 223.

The actuation unit 243 is configured to bend one or more of the proximal bending segment 254C, the middle bending segment 254B, and the distal segment 254A via the connector assembly 242 according to commands from the bendable-device controller 21.

According to some embodiments, either during insertion or retraction of the steerable instrument 24, the bendable-device controller 21 may control the linear stage 224 of the support platform 223 to move the steerable section 253 along the center line of a lumen (e.g., an airway) in a desired trajectory followed by active control of the bending segments 254. This is similar to known shaft-guidance techniques used to control robotic guided catheters or endoscopes with the goal of forcing the flexible shaft of the sheath to keep to a desired trajectory. In one example, when using the system controller 11, the steerable instrument 24 is robotically controlled to advance the steerable instrument 24 through a lumen while the actuation-control sensors 437 measure the actuation force, insertion depth, the angulations of user-controlled steerable sections, etc., to obtain trajectory information. The trajectory information is stored in a memory of the system and is continuously updated. After a short advance in insertion or retraction distance, the shape of the steerable section 253 is changed (e.g., corrected) by adjusting (actuating) one or more of the bending segments 254 in such a way that the new shape closely matches the desired trajectory. This process is repeated until the target area is reached. The same process can be applied when the steerable instrument 24 is controlled to withdraw the steerable section 253 from the lumen.

Also, as shown in FIG. 25B, the steerable instrument 24 may also include one or more position sensors 245. In some embodiments, the one or more position sensors 245 are electromagnetic (EM) sensors. And, in some embodiments, the one or more position sensors 245 are five-degree-of-freedom or six-degree-of-freedom sensors. Also, in some embodiments, the one or more position sensors 245 are fixed relative to each other at or near the distal end 252 (e.g., tip) of the tubular flexible body 250 or at or near the distal end of the steerable section 253 (e.g., the distal end of the distal bending segment 254A), which may also be the distal end 252 of the tubular flexible body 250. The one or more position sensors 245 and the position-tracking device 27 may constitute a position-tracking system.

FIG. 26A illustrates an example embodiment of a steerable section 253 of a bendable medical device. Each of the bending segments 254 in the steerable section 253 includes a respective radiopaque marker 281. In this embodiment, the radiopaque markers 281 are the anchor rings 259—each anchor ring 259 includes (is at least in part, composed of) radiopaque material. Also, the anchor rings 259 may include different radiopaque materials. This may allow the radiopaque markers 281 (the radiopaque anchor rings 259 in this example) to be distinguished from each other in an image of the steerable section 253.

FIG. 26B illustrates an example embodiment of a steerable section 253 of a bendable medical device. Each of the bending segments 254 in the steerable section 253 includes a respective radiopaque marker 281. And in this embodiment, the radiopaque markers 281 are the anchor rings 259—each anchor ring 259 includes radiopaque material. Also, the anchor rings 259 may have identical compositions of radiopaque materials. However, the anchor rings 259 also have different openings that pass through the anchor rings 259 in directions that are perpendicular to the axis of the tool channel 256. The different openings may allow the radiopaque markers 281 (the radiopaque anchor rings 259 in this example) to be distinguished from each other in an image of the steerable section 253.

Figure 27:
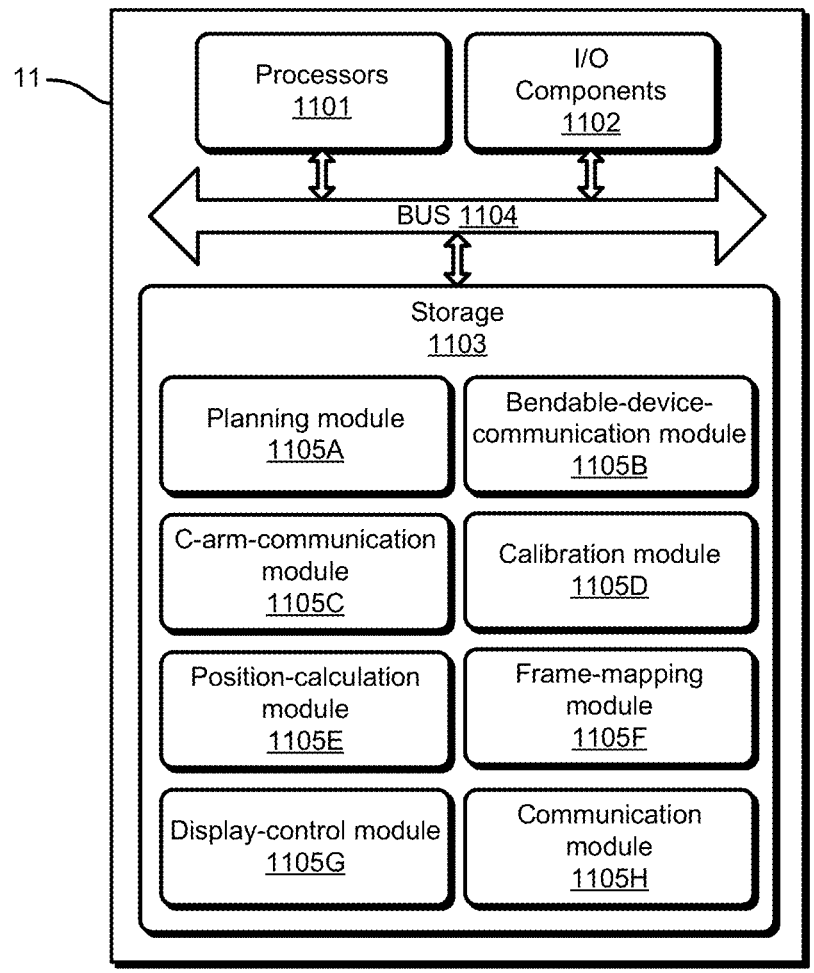
FIG. 27 illustrates an example embodiment of a system controller.

FIG. 27 illustrates an example embodiment of a system controller 11. The system controller 11 includes one or more processors 1101, one or more I/O components 1102, and storage 1103. Also, the hardware components of the system controller 11 communicate via one or more buses 1104 or other electrical connections. Examples of buses 1104 include a universal serial bus (USB), an IEEE 1394 bus, a PCI bus, an Accelerated Graphics Port (AGP) bus, a Serial AT Attachment (SATA) bus, and a Small Computer System Interface (SCSI) bus.

The one or more processors 1101 include one or more central processing units (CPUs), which may include one or more microprocessors (e.g., a single core microprocessor, a multi-core microprocessor); one or more graphics processing units (GPUs); one or more application-specific integrated circuits (ASICs); one or more field-programmable-gate arrays (FPGAs); one or more digital signal processors (DSPs); or other electronic circuitry (e.g., other integrated circuits). The I/O components 1102 include communication components (e.g., a GPU, a network-interface controller) that communicate with a display device 15, a bendable-device controller 21, a position-tracking device 27, a C-arm controller 32, a network (not shown), and other input or output devices 29 (not illustrated), which may include a keyboard, a mouse, a printing device, a touch screen, a light pen, an optical-storage device, a scanner, a microphone, a drive, a joystick, and a control pad.

The storage 1103 includes one or more computer-readable storage media. As used herein, a computer-readable storage medium includes an article of manufacture, for example a magnetic disk (e.g., a floppy disk, a hard disk), an optical disc (e.g., a CD, a DVD, a Blu-ray), a magneto-optical disk, magnetic tape, and semiconductor memory (e.g., a non-volatile memory card, flash memory, a solid-state drive, SRAM, DRAM, EPROM, EEPROM). The storage 1103, which may include both ROM and RAM, can store computer-readable data or computer-executable instructions.

The system controller 11 additionally includes a planning module 1105A, a bendable-device-communication module 1105B, a C-arm-communication module 1105C, a calibration module 1105D, a position-calculation module 1105E, a frame-mapping module 1105F, a display-control module 1105G, and a communication module 1105H. A module includes logic, computer-readable data, or computer-executable instructions. In the embodiment shown in FIG. 27, the modules are implemented in software (e.g., Assembly, C, C++, C#, Java, BASIC, Perl, Visual Basic, Python). However, in some embodiments, the modules are implemented in hardware (e.g., customized circuitry) or, alternatively, a combination of software and hardware. When the modules are implemented, at least in part, in software, then the software can be stored in the storage 1103. Also, in some embodiments, the system controller 11 includes additional or fewer modules, the modules are combined into fewer modules, or the modules are divided into more modules.

The planning module 1105A includes instructions that cause the system controller 11 to generate a 3D model of a branching structure from images of the branching structure, specify a target in the 3D model, and determine a route (navigation path) through the branching structure to the target. For example, some embodiments of the planning module 1105A include instructions that cause the applicable components (e.g., the processors 1101, the I/O components 1102, the storage 1103) of the system controller 11 to perform at least some of the operations that are described in blocks B2205-B2230 in FIG. 22. Also, the applicable components of the system controller 11 operating according to the planning module 1105A realize an example of a planning unit.

The bendable-device-communication module 1105B includes instructions that cause the system controller 11 to communicate with a bendable medical device, for example by communicating with a bendable-device controller. The communication may include sending control signals to the bendable medical device and receiving signals (e.g., sensor signals, endoscopic images) from the bendable medical device. For example, some embodiments of the bendable-device-communication module 1105B include instructions that cause the applicable components (e.g., the processors 1101, the I/O components 1102, the storage 1103) of the system controller 11 to communicate with the bendable-device controller to perform at least some of the operations that are described in blocks B525 and B545 in FIG. 5; in blocks B805 and B835 in FIG. 8; in block B1130 in FIG. 11; in blocks B1205, B1235, and B1240 in FIG. 12; in blocks B1405, B1435, and B1440 in FIG. 14; in block B1640 in FIG. 16; in block B1845 in FIG. 18; in block B2035 in FIG. 20; and in blocks B2305, B2310, B2315, B2330 and B2335 in FIG. 23. Also, the applicable components of the system controller 11 operating according to the bendable-device-communication module 1105B realize an example of a bendable-device-communication unit.

The C-arm-communication module 1105C includes instructions that cause the system controller 11 to communicate with a C-arm scanner 31, for example by communicating with a C-arm controller 32. The communication may include sending control signals to the C-arm scanner 31 and receiving data (e.g., C-arm positional information, X-ray images (such as fluoroscopic images)) from the C-arm scanner 31. For example, some embodiments of the C-arm-communication module 1105C include instructions that cause the applicable components (e.g., the processors 1101, the I/O components 1102, the storage 1103) of the system controller 11 to perform at least some of the operations that are described in blocks B510, B515, B530, and B535 in FIG. 5; in block B810 in FIG. 8; in blocks B1105, B1135, and B1150 in FIG. 11; in blocks B1205, B1240, and B1255 in FIG. 12; in blocks B1405, B1440, and B1470 in FIG. 14; in blocks B1610, B1650, and B1675 in FIG. 16; in blocks B1805, B1810, B1850, and B1855 in FIG. 18; in blocks B2005, B2040, and B2055 in FIG. 20; and in block B2205 in FIG. 22. Also, the applicable components of the system controller 11 operating according to the C-arm-communication module 1105C realize an example of a C-arm-communication unit.

The calibration module 1105D includes instructions that cause the system controller 11 to perform a calibration procedure. For example, some embodiments of the calibration module 1105D include instructions that cause the applicable components (e.g., the processors 1101, the I/O components 1102, the storage 1103) of the system controller 11 to perform at least some of the operations that are described in blocks B505-B550 in FIG. 5. Also, the applicable components of the system controller 11 operating according to the calibration module 1105D realize an example of a calibration unit.

The position-calculation module 1105E includes instructions that cause the system controller 11 to obtain distal-end positional information, for example from a bendable-medical device or from a position-tracking system (which includes a position-tracking device 27 and one or more position sensors 245). For example, some embodiments of the position-calculation module 1105E include instructions that cause the applicable components (e.g., the processors 1101, the I/O components 1102, the storage 1103) of the system controller 11 to perform at least some of the operations that are described in block B820 in FIG. 8, in block B1115 in FIG. 11, in block B1220 in FIG. 12, in blocks B1410 and B1445 in FIG. 14, in blocks B1615 and B1645 in FIG. 16, in block B1830 in FIG. 18; and in block B2020 in FIG. 20. Also, the applicable components of the system controller 11 operating according to the position-calculation module 1105E realize an example of a position-calculation unit.

The frame-mapping module 1105F includes instructions that cause the system controller 11 to generate reference-frame mappings and to map instructed directions that are obtained in one reference frame (e.g., a reference frame of a fluoroscopic viewpoint) to movement directions in another reference frame (e.g., a reference frame of a distal end). For example, some embodiments of the frame-mapping module 1105F include instructions that cause the applicable components (e.g., the processors 1101, the I/O components 1102, the storage 1103) of the system controller 11 to perform at least some of the operations that are described in blocks B825 and B830 (including B832 and B834) in FIG. 8, in blocks B1120 and B1125 in FIG. 11, in blocks B1225 and B1230 in FIG. 12, in blocks B1415 and B1450 in FIG. 14, in blocks B1620 and B1655 in FIG. 16, in blocks B1835 and B1840 in FIG. 18, and in blocks B2025 and B2030 in FIG. 20. Also, the applicable components of the system controller 11 operating according to the frame-mapping module 1105F realize an example of a frame-mapping unit.

The display-control module 1105G includes instructions that cause the system controller 11 to control the display on a display device 15, such as the display of fluoroscopic images, endoscopic images, views (e.g., first-person views) of 3D models, and inter-view-relationship indicators. And the display-control module 1105G may include instructions that cause the system controller 11 to generate inter-view-relationship indicators. For example, some embodiments of the display-control module 1105G include instructions that cause the applicable components (e.g., the processors 1101, the I/O components 1102, the storage 1103) of the system controller 11 to perform at least some of the operations that are described in block B810 in FIG. 8; in blocks B1105 and B1140 in FIG. 11; in blocks B1210 and B1245 in FIG. 12; in blocks B1420, B1425, B1455, and B1460 in FIG. 14; in blocks B1625, B1630, B1660, and B1665 in FIG. 16; in blocks B1815 and B1860 in FIG. 18; and in blocks B2010 and B2045 in FIG. 20. Also, the applicable components of the system controller 11 operating according to the display-control module 1105G realize an example of a display-control unit.

The communication module 1105H includes instructions that cause the system controller 11 to communicate with input devices (e.g., obtain instructed directions from an input device 29) and with other devices (e.g., a PACs system). For example, some embodiments of the communication module 1105H include instructions that cause the applicable components (e.g., the processors 1101, the I/O components 1102, the storage 1103) of the system controller 11 to perform at least some of the operations that are described in blocks B815 and B840 in FIG. 8; in blocks B1110, B1155, and B1160 in FIG. 11; in blocks B1215, B1260, and B1265 in FIG. 12; in blocks B1430, B1475, and B1480 in FIG. 14; in blocks B1635, B1680, and B1685 in FIG. 16; in blocks B1820, B1825, B1865, and B1870 in FIG. 18; and in blocks B2015, B2060, and B2065 in FIG. 20. Also, the applicable components of the system controller 11 operating according to the communication module 1105H realize an example of a communication unit.

Figure 28:
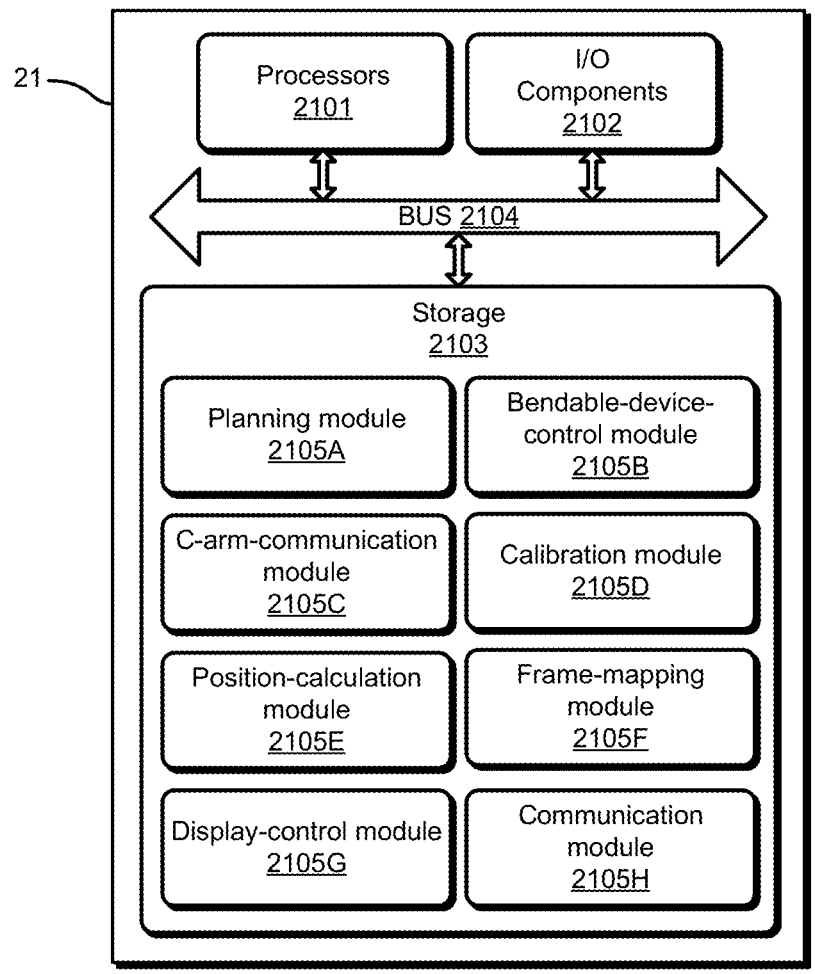
FIG. 28 illustrates an example embodiment of a bendable-device controller.

FIG. 28 illustrates an example embodiment of a bendable-device controller. The bendable-device controller 21 includes one or more processors 2101, one or more I/O components 2102, storage 2103, and one or more busses 2104.

The bendable-device controller 21 additionally includes a planning module 2105A, a bendable-device-control module 2105B, a C-arm-communication module 2105C, a calibration module 2105D, a position-calculation module 2105E, a frame-mapping module 2105F, a display-control module 2105G, and a communication module 2105H.

The planning module 2105A, the C-arm-communication module 2105C, the calibration module 2105D, the position-calculation module 2105E, the frame-mapping module 2105F, the display-control module 2105G, and the communication module 2105H are similar to the modules in FIG. 27. However, in FIG. 28, the planning module 2105A, the C-arm-communication module 2105C, the calibration module 2105D, the position-calculation module 2105E, the frame-mapping module 2105F, the display-control module 2105G, and the communication module 2105H include instructions that cause the applicable components (e.g., the processors 2101, the I/O components 2102, the storage 2103) of the bendable-device controller 21 to perform the operations.

The bendable-device-control module 2105B includes instructions that cause the bendable-device controller 21 to control a bendable medical device. For example, some embodiments of the bendable-device-control module 2105B include instructions that cause the applicable components (e.g., the processors 2101, the I/O components 2102, the storage 2103) of the bendable-device controller 21 to control a bendable medical device to perform at least some of the operations that are described in blocks B525 and B545 in FIG. 5; in blocks B805 and B835 in FIG. 8; in block B1130 in FIG. 11; in blocks B1205, B1235, and B1240 in FIG. 12; in blocks B1405, B1435, and B1440 in FIG. 14; in block B1640 in FIG. 16; in block B1845 in FIG. 18; in block B2035 in FIG. 20; and in blocks B2305, B2310, B2315, B2330 and B2335 in FIG. 23. Also, the applicable components of the bendable-device controller 21 operating according to the bendable-device-control module 2105B realize an example of a bendable-device-control unit.

Also, some embodiments of the bendable-device controller 21 omit one or more of the following: the planning module 2105A, the C-arm-communication module 2105C, the calibration module 2105D, the position-calculation module 2105E, the frame-mapping module 2105F, the display-control module 2105G, and the communication module 2105H.

The scope of the claims is not limited to the above-described embodiments and includes various modifications and equivalent arrangements.

The invention claimed is:

1. A system comprising:
one or more computer-readable media; and
one or more processors in communication with the one or more computer-readable media, wherein the one or more processors and the one or more computer-readable media are configured to cooperate to perform operations that comprise:
obtaining a fluoroscopic image that was generated by a C-arm scanner and corresponding C-arm positional information for the fluoroscopic image, wherein the fluoroscopic image depicts a distal end of a bendable medical device, and wherein the C-arm positional information indicates a rotation angle of a C-arm of the C-arm scanner;
determining an orientation of the distal end in an image plane of the fluoroscopic image, wherein the image plane is defined in a detector reference frame of the C-arm scanner;
obtaining an instructed direction;
determining, in the image plane, a movement direction of the distal end that corresponds to the instructed direction, wherein the determining is based on the orientation of the distal end in the image plane, and wherein the movement direction lies in the imaging plane;
mapping the movement direction from the image plane, which is defined in the detector reference frame, to a distal-end reference frame of the distal end, thereby generating a mapped movement direction, wherein the detector reference frame is different from the distal-end reference frame, wherein the mapping is based on an orientation of the distal end in an intermediate reference frame and on the C-arm positional information, and wherein the mapped movement direction, which is defined in the distal-end reference frame, lies in the image plane; and
controlling the distal end to move according to the mapped movement direction.

2. The system of claim 1, wherein the intermediate reference frame is a reference frame of a proximal end of the bendable medical device.

3. The system of claim 1, wherein the intermediate reference frame is a reference frame of a position-tracking system.

4. The system of claim 1, wherein the orientation of the distal end in the image plane is determined based on the orientation of the distal end in the intermediate reference frame and on the C-arm positional information.

5. The system of claim 1, wherein the orientation of the distal end in the image plane is determined based on a computer-vision analysis of the fluoroscopic image.

6. The system of claim 1, wherein the mapped movement direction lies entirely in the image plane.

7. The system of claim 1, wherein the instructed direction is right or, alternatively, left.

8. The system of claim 1, further comprising an input device,
wherein the input device includes a first button and a second button,
wherein the input device is configured to send a signal that indicates "right" as the instructed direction in response to activation of the first button, and
wherein the input device is configured to send a signal that indicates "left" as the instructed direction in response to activation of the second button.

9. The system of claim 1, wherein the distal end of the bendable medical device includes three bending segments, which are bendable independent from each other;
wherein the one or more processors and the one or more computer-readable media are further configured to cooperate to identify a bending segment, of the three bending segments, that corresponds to the instructed direction; and
wherein controlling the distal end to move according to the mapped movement direction includes controlling the bending segment that corresponds to the instructed direction to bend in the mapped movement direction.

10. The system of claim 9, wherein controlling the distal end to move according to the mapped movement direction includes controlling the two bending segments, of the three bending segments, that do not correspond to the instructed direction to retain their current poses.

11. The system of claim 9, further comprising an input device,
wherein the three bending segments include a first bending segment, a second bending segment, and a third bending segment,
wherein the input device includes a first button, a second button, a third button, a fourth button, a fifth button, and a sixth button,
wherein the input device is configured to send a signal that corresponds to the first bending segment and that indicates "right" as the instructed direction in response to activation of the first button,
wherein the input device is configured to send a signal that corresponds to the first bending segment and that indicates "left" as the instructed direction in response to activation of the second button,
wherein the input device is configured to send a signal that corresponds to the second bending segment and that indicates "right" as the instructed direction in response to activation of the third button,
wherein the input device is configured to send a signal that corresponds to the second bending segment and that indicates "left" as the instructed direction in response to activation of the fourth button, wherein the input device is configured to send a signal that corresponds to the third bending segment and that indicates "right" as the instructed direction in response to activation of the fifth button, and wherein the input device is configured to send a signal that corresponds to the third bending segment and that indicates "left" as the instructed direction in response to activation of the sixth button.

12. The system of claim 1, further comprising the bendable medical device, wherein the distal end of the bendable medical device includes three bending segments, which are bendable independent from each other, wherein the three bending segments include a first bending segment, a second bending segment, and a third bending segment, each of which includes a respective distal end, wherein the distal end of the first bending segment includes a first radiopaque marker, wherein the distal end of the second bending segment includes a second radiopaque marker, wherein the distal end of the third bending segment includes a third radiopaque marker, and wherein the first radiopaque marker, the second radiopaque marker, and the third radiopaque marker are composed of different radiopaque materials that cause the first radiopaque marker, the second radiopaque marker, and the third radiopaque marker to have different appearances in the fluoroscopic image.

13. The system of claim 1, further comprising the bendable medical device, wherein the distal end of the bendable medical device includes three bending segments, which are bendable independent from each other, wherein the three bending segments include a first bending segment, a second bending segment, and a third bending segment, each of which includes a respective distal end, wherein the distal end of the first bending segment includes a first radiopaque marker that includes one or more respective openings, wherein the distal end of the second bending segment includes a second radiopaque marker that includes one or more respective openings, wherein the distal end of the third bending segment includes a third radiopaque marker that includes one or more respective openings, and wherein the one or more respective openings of the first radiopaque marker, the second radiopaque marker, and the third radiopaque marker have different shapes.

14. A method for controlling a bendable medical device, the method comprising:

obtaining a fluoroscopic image that was generated by a C-arm scanner and corresponding C-arm positional information for the fluoroscopic image, wherein the fluoroscopic image depicts a distal end of a bendable medical device, and wherein the C-arm positional information indicates a rotation angle of a C-arm of the C-arm scanner;

obtaining an orientation of the distal end in an image plane of the fluoroscopic image, wherein the image plane is defined in a detector reference frame of the C-arm scanner;

obtaining an instructed direction;

determining, in the image plane, a movement direction of the distal end that corresponds to the instructed direction, wherein the determining is based on the orientation of the distal end in the image plane, and wherein the movement direction lies in the imaging plane;

mapping the movement direction from the image plane, which is defined in the detector reference frame, to a distal-end reference frame of the distal end, thereby generating a mapped movement direction, wherein the detector reference frame is different from the distal-end reference frame, wherein the mapping is based on an orientation of the distal end in an intermediate reference frame and on the C-arm positional information, and wherein the mapped movement direction, which is defined in the distal-end reference frame, lies in the image plane; and controlling the distal end to move according to the mapped movement direction.

15. The method of claim 14, wherein the intermediate reference frame is a reference frame of a proximal end of the bendable medical device or is a reference frame of a position-tracking system.

16. The method of claim 14, wherein the mapped movement direction lies entirely in the image plane.

17. The method of claim 14, wherein the mapping of the movement direction includes generating a rotation matrix that describes an orientation of the distal-end reference frame relative to the intermediate reference frame or generating a rotation matrix that describes an orientation of the detector reference frame relative to the intermediate reference frame.

18. The method of claim 17, wherein the mapping of the movement direction includes both generating the rotation matrix that describes the orientation of the distal-end reference frame relative to the intermediate reference frame and generating the rotation matrix that describes the orientation of the detector reference frame relative to the intermediate reference frame.

19. The method of claim 18, wherein the mapping of the movement direction includes generating a rotation matrix that describes an orientation of the distal-end reference frame relative to the detector reference frame based on the rotation matrix that describes the orientation of the distal-end reference frame relative to the intermediate reference frame and on the rotation matrix that describes the orientation of the detector reference frame relative to the intermediate reference frame.

20. A method for controlling a bendable medical device, the method comprising:

obtaining a fluoroscopic image that was generated by a C-arm scanner and corresponding C-arm positional information for the fluoroscopic image, wherein the fluoroscopic image depicts a distal end of a bendable medical device, and wherein the C-arm positional information indicates a rotation angle of a C-arm of the C-arm scanner;

obtaining distal-end positional information, which indicates an orientation of the distal end;

generating a reference-frame mapping between a detector reference frame of the C-arm scanner and a distal-end reference frame of the distal end, wherein the reference-frame mapping is generated based on an orientation of the distal end in an intermediate reference frame and on the C-arm positional information, wherein the detector reference frame is different from the distal-end reference frame, and wherein the intermediate reference frame is different from both the detector reference frame and the distal-end reference frame;

generating an inter-view-relationship indicator, which indicates a relationship between the detector reference frame and the distal-end reference frame, based on the reference-frame mapping; and displaying the fluoroscopic image and the inter-view-relationship indicator.

21. The method of claim 20, further comprising:

obtaining an endoscopic image that was captured from an imaging device at the distal end of the bendable medical device; and displaying the endoscopic image with the fluoroscopic image and the inter-view-relationship indicator.

22. The method of claim 21, wherein the inter-view-relationship indicator is superimposed on the endoscopic image.

23. The method of claim 20, wherein generating the reference-frame mapping between the detector reference frame and the distal-end reference frame includes generating a rotation matrix that describes an orientation of the distal-end reference frame relative to the intermediate reference frame or generating a rotation matrix that describes an orientation of the detector reference frame relative to the intermediate reference frame.

24. The method of claim 23, wherein generating the reference-frame mapping between the detector reference frame and the distal-end reference frame includes both generating the rotation matrix that describes the orientation of the distal-end reference frame relative to the intermediate reference frame and generating the rotation matrix that describes the orientation of the detector reference frame relative to the intermediate reference frame.

25. The method of claim 24, wherein the intermediate reference frame is a reference frame of a proximal end of the bendable medical device or is a reference frame of a position-tracking system.

* * * * *